US006281010B1

(12) United States Patent
Gao et al.

(10) Patent No.: US 6,281,010 B1
(45) Date of Patent: Aug. 28, 2001

(54) ADENOVIRUS GENE THERAPY VEHICLE AND CELL LINE

(75) Inventors: Guang-Ping Gao, Havertown; James M. Wilson, Gladwyne, both of PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 08/549,489

(22) Filed: Oct. 27, 1995

Related U.S. Application Data

(63) Continuation-in-part of application No. 08/462,014, filed on Jun. 5, 1995, now Pat. No. 5,756,283.

(51) Int. Cl.[7] ........................... C12N 15/00; C12N 15/88

(52) U.S. Cl. ....................... 435/325; 435/320.1; 435/455; 435/91.4

(58) Field of Search .......................... 514/44; 435/173.3, 435/320.1, 69.1, 325, 62, 455, 91.4; 424/93.2, 93.21

(56) References Cited

U.S. PATENT DOCUMENTS

| | | | |
|---|---|---|---|
| 5,173,414 | 12/1992 | Lebkowski et al. | 435/455 |
| 5,252,479 | 10/1993 | Srivasta | 435/235.1 |
| 5,354,678 | 10/1994 | Lebkowski | 435/455 |
| 5,543,328 | 8/1996 | McClelland | 435/320.1 |
| 5,707,798 * | 1/1998 | Brann | 435/6 |
| 5,756,283 * | 5/1998 | Wilson et al. | 435/5 |
| 5,776,502 * | 7/1998 | Foulkes et al. | 424/617 |
| 5,851,806 * | 12/1998 | Kovesdi et al. | 435/91.4 |
| 5,872,005 * | 2/1999 | Wang et al. | 435/320.1 |
| 5,928,944 * | 7/1999 | Seth et al. | 435/375 |
| 5,932,210 * | 8/1999 | Gregory et al. | 424/93.2 |
| 5,994,106 * | 11/1999 | Kovesdi et al. | 435/91.4 |
| 5,994,128 * | 11/1999 | Fallaux et al. | 435/325 |

FOREIGN PATENT DOCUMENTS

| | | |
|---|---|---|
| 2790292 * | 4/1993 | (AU) . |
| WO93/19191 | 9/1993 | (WO) . |
| WO94/12649 | 6/1994 | (WO) . |
| WO94/26914 | 11/1994 | (WO) . |
| WO94/28152 | 12/1994 | (WO) . |
| WO94/28938 | 12/1994 | (WO) . |
| WO95/00655 | 1/1995 | (WO) . |
| WO95/02697 | 1/1995 | (WO) . |
| WO95/06743 | 3/1995 | (WO) . |
| WO95/10623 | 4/1995 | (WO) . |
| WO95/20671 | 8/1995 | (WO) . |
| WO95/27071 | 10/1995 | (WO) . |
| WO95/34671 | 12/1995 | (WO) . |
| WO96/12030 | 4/1996 | (WO) . |
| WO96/13596 | 5/1996 | (WO) . |
| WO96/13597 | 5/1996 | (WO) . |
| WO96/13598 | 5/1996 | (WO) . |
| WO96/14061 | 5/1996 | (WO) . |
| WO96/18418 | 6/1996 | (WO) . |
| WO96/22378 | 7/1996 | (WO) . |

OTHER PUBLICATIONS

Stefan Kafsson (1994) Blood, vol. 78, No. 10: pp. 2481–2492.*

Dong et al. (1996) Human Gene Therapy 7: 319–331.*

Scaria et al. (Jun. 28, 1995) Gene Therapy 2; 295–298.*

Ronald Crystal (1995) Science, vol. 270; pp. 404–409.*

Coghlan (Nov. 25, 1995) New Scientist pp:15–16.*

Marshall (Aug. 1995) Science, vol. 269, pp:1050–1055.*

Marshall (Dec. 1995) Science, vol. 270, pp: 1751.*

Onlzin & Motulsky (Dec. 7, 1995) NIH Report on Gene Therapy.*

Ohman et al. (1993) Virology 194, pp. 50–58.*

Wilson et al. (1994) Hum. Gene. Ther. 5: 501–519.*

Armentano et al. (Oct. 9, 1995) Hum. Gene. Ther. 6: 1343–1353.*

Bridge et al (1993) Virology 193: pp 794–801.*

Bakner (1992) Current Topics in Microbiology and Immunology, vol. 158 pp. 39–66.*

Weinberg et al (1983) Proc. Natl. Acad. Sci. USA, vol. 80, pp: 5383–5386.*

Hirt et al., Methods in Cell Biology, 1994, vol. 43:247–262, 1994.*

Defective Adenovirus Vectors and their Use In Gene Therapy ,WO 95102697, translated by Schreiber Translation Inc., Oct. 1995.*

Glick et al., *Molecular Biotechnology,* ASM Press, pp. 29–30, 1994.*

R. Boucher et al, "Clinical Protocol—Gene Therapy for Cystic Fibrosis Using E1–Deleted Adenovirus: A Phase I Trial in the Nasal Cavity The University of North Carolina at Chapel Hill", *Human Gene Ther.,* 5:615–639 (May, 1994).

J. Engelhardt et al, "Direct Gene Transfer of Human CFTR into Human Bronchial Epithelia of Xenografts with E1–deleted Adenoviruses", *Nat. Genet.,* 4:27–34 (May, 1993).

K. Fisher et al, "Biochemical and Functional Analysis of an Adenovirus–Based Ligand Complex for Gene Transfer", *Biochem. J.,* 299:49–58 (Apr. 1, 1994).

J. Goldstein et al, "Defective Lipoprotein Receptors and Atheroschlerosis", *New Engl. J. Med.,* 309 (11983):288–296 (Aug., 1983).

(List continued on next page.)

*Primary Examiner*—Dave Trong Nguyen
(74) *Attorney, Agent, or Firm*—Howson and Howson

(57) ABSTRACT

A novel adenovirus E1/E4 expressing packaging cell line is provided, which permits the generation of recombinant adenoviruses deleted in both gene regions. The E1/E4 deleted recombinant adenovirus is capable of expressing a selected transgene product in cells in vivo or in vitro. This recombinant virus is useful in the treatment of genetic disorders.

8 Claims, 39 Drawing Sheets

OTHER PUBLICATIONS

M. Goldman et al, "Expression of Integrin is Necessary for Efficient Adenovirus–Mediated Gene Transfer in the Human Airway", *J. Virol., 69:*5951–5958 (Oct., 1995) [Goldman I].

M. Goldman et al, "Transfer of the CFTR Gene to the Lung of Nonhuman Primates with E1–Deleted, E2a–Defective Recombinant Adenoviruses: A Preclinical Toxicology Study", *Human Gene Therapy, 6:*839–851 (Jul., 1995) [Goldman II].

M. Goldman et al, "Gene Therapy in a Xenograft Model of Cystic Fibrosis Lung Corrects Chloride Transport more Effectively that the Sodium Defect", *Nature Genetics, 9:*126–131 (Feb., 1995) [Goldman III].

M. Grable et al, "Adenovirus Type 5 Packaging Domain is Composed of a Repeated Element that is Functionally Redundant", *J. Virol., 64*(5):2047–2056 (May, 1990).

M. Grossman et al, "Towards Liver–Directed Gene Therapy: Retrovirus–mediated Gene Transfer into Human Hepatocytes", *Somatic Cell and Molec. Genet., 17*(6):601–607 (Nov., 1991).

B. Grubb et al, "Inefficient Gene Transfer by Adenovirus Vector to Cystic Fibrosis Airway Epithelia of Mice and Humans", *Nature, 371:*802–806 (Oct. 27, 1994).

M. Horwitz, "Adenoviridae and Their Replication", *Virology,* 2d edition, ed. B. N. Fields, Raven Press, Ltd., New York, Chapter 60, pp 1679–1721 (1990).

S. Ishibashi et al, "Massive Xanthomatosis and Atherosclerosis in Cholesterol–fed Low Density Lipoprotein Receptor–negative Mice", *J. Clin. Invest., 93:*1885–1893 (May, 1994) [Ishibashi I].

S. Ishibashi et al, "Hypercholesterolemia in Low Density Lipoprotein Receptor Knockout Mice and its Reversal by Adenovirus–mediated Gene Delivery", *J. Clin. Invest., 92:*883–893 (Aug., 1993) [Ishibashi II].

M. Knowles et al, "A Controlled Study of Adenoviral–Vector–Mediated Gene Transfer in the Nasal Epithelium of Patients with Cystic Fibrosis", *N. Engl. J. Med., 333*(13):823–831 (Sep., 1995).

K. Kozarsky et al, "In Vivo Correction of Low Density Lipoprotein Receptor Deficiency in the Watanabe Heritable Hyperlipidemic Rabbit with Recombinant Adenoviruses", *J. Biol. Chem., 269*(18):13695–13702 (May 6, 1994) [Kozarsky I].

K. Kozarsky et al, "Adenovirus–Mediated Correction of the Genetic Defect in Hepatocytes from Patients with Familial Hypercholesterolemia", *Somatic Cell and Molecular Genetics, 19*(5):449–458 (Sep., 1993) [Kozarsky II].

K. Kozarsky et al, "Gene Therapy: Adenovirus Vectors", *Curr. Opin. Genet. Devel., 3:*499–503 (Mar., 1993) [Kozarsky III].

J. Pilewski et al, "Adenovirus–mediated Gene Transfer to Human Bronchial Submucosal Glands Using Xenografts", *Amer. J. Physiol: Lung, Cell and Mole Physiol., 268:*L657–L665 (Apr., 1995) [Pilewski I].

J. Pilewski et al, "ICAM–1 Expression on Bronchial Epithelium after Recombinant Adenovirus Infection", *Am. J. Respir. Cell Mol. Biol., 12:*142–148 (Feb., 1995) [Pilewski II].

B. Roessler et al, "Adenoviral–mediated Gene Transfer to Rabbit Synovium in Vivo", *J. Clin. Invest., 92:*1085–1092 (Aug., 1993).

T. Shenk et al, "Genetic Analysis of Adenoviruses", *Current Topics in Microbiol. and Immunol., 111:*1–39 (1984).

T. Smith et al, "Adenovirus Mediated Expression of Therapeutic Plasma Levels of Human Factor IX in Mice", *Nature Genetics, 5:*397–402 (Dec., 1993).

K. Tanzawa et al, "WHHL–Rabbit: A Low Density Lipoprotein Receptor–Deficient Animal Model for Familial Hypercholesterolemia", *FEBS Letters, 118*(1):81–84 (Aug., 1980).

Y. Watanabe et al, "Serial Inbreeding of Rabbits with Hereditary Hyperlipidemia (WHHL–Rabbit)", *Atherosclerosis, 36:*261–268 (1980).

J. Wilson et al, "Correction of the Genetic Defect in Hepatocytes from the Watanabe Heritable Hyperlipidemic Rabbit", *Proc. Natl. Acad. Sci. USA, 85:*4421–4425 (Jun., 1988) [Wilson I].

J. Wilson et al, "Research Article—Transplantation of Allogeneic Hepatocytes into LDL Receptor Deficient Rabbits Leads to Transient Improvement in Hypercholesterolemia", *Clin. Biotechnology, 3:*21–26 (Spring, 1991) [Wilson II].

J. Wilson et al, "A Novel Mechanism for Achieving Transgene Persistence in Vivo After Somatic Gene Transfer into Hepatocytes", *J. Biol. Chem., 267*(16):11483–11489 (Jun., 1992) [Wilson III].

J. Wilson et al, "Vehicles for Gene Therapy", *Nature,* 365:691–692 (Oct. 21, 1993) [Wilson IV].

C. Wu et al, "Targeting Genes: Delivery and Persistent Expression of a Foreign Gene Driven by Mammalian Regulatory Elements in Vivo", *J. Biol. Chem., 264*(29):16985–16987 (Oct. 15, 1989).

Y. Yang et al, "MHC Class I–Restricted Cytotoxic T Lymphocytes to Viral Antigens Destroy Hepatocytes in Mice Infected with E1–Deleted Recombinant Adenoviruses", *Immunity, 1:*433–442 (Aug., 1994) [Yang I].

Y. Yang et al, "Cellular Immunity to Viral Antigens Limits E1–Deleted Adenoviruses for Gene Therapy", *Proc. Natl. Acad. Sci. USA, 91:*4407–4411 (May, 1994) [Yang II].

Y. Yang et al, "Inactivation of E2a in Recombinant Adenoviruses Improves the Prospect for Gene Therapy in Cystic Fibrosis", *Nature Genetics, 7:*362–369 (Jul., 1994) [Yang III].

Y. Yang et al, "Recombinant IL–12 Prevents Formation of Blocking IgA Antibodies to Recombinant Adenovirus and Allows Repeated Gene Therapy to Mouse Lung", *Nat. Med., 1*(9):890–893 (Sep., 1995) [Yang IV].

Y. Yang et al, "Upregulation of Class I MHC Antigens by Interferon– is Necessary for the T Cell–Mediated Elimination of Recombinant Adenovirus Infected Hepatocytes in Vivo", *Proc. Natl. Acad. Sci. USA, 92:*7257–7261 (Aug., 1995) [Yang V].

Y. Yang et al, "Cellular and Humoral Immune Responses to Viral Antigens Create Barriers to Lung–Directed Gene Therapy with Recombinant Adenoviruses", *J. Virol., 69*(4):2004–2015 (Apr., 1995) [Yang VI].

Y. Yang et al, "Clearance of Adenovirus–Infected Hepatocytes by MHC Class I–Restricted CD4+ CTLs in Vivo", *J. Immunol., 155:*2564–2570 (Jun., 1995) [Yang VII].

J. Engelhardt et al, "Prolonged Transgene Expression in Cotton Rat Lung with Recombinant Adenoviruses Defective in E2a", Human Gene Therapy, 5:1217–1229 (Oct., 1994) [Engelhardt III].

Q. Wang et al, "A Packaging Cell Line for Propagation of Recombinant Adenovirus Vectors Containing Two Lethal Gene–Region Deletions", Gene Therapy, 2:775–783 (Dec. 19, 1995).

K. Berkner, "Development of Adenovirus Vectors for the Expression of Heterologous Genes", BioTechniques, 6(7):616–629 (1988).

E. Bridge et al, "Redundant Control of Adenovirus Late Gene Expression by Early Region 4", J. Virol., 63(2):631–638 (Feb., 1989).

Y. Dai et al, "Cellular and Humoral Immune Responses to Adenoviral Vectors Containing Factor IX Gene: Tolerization of Factor IX and Vector Antigens Allows for Long–Term Expression", Proc. Natl. Acad. Sci. USA, 92:1401–1405 (Feb., 1995).

J. Engelhardt et al, "Ablation of E2A in Recombinant Adenoviruses Improves Transgene Persistence and Decreases Inflammatory Response in Mouse Liver", Proc. Natl. Acad. Sci. USA, 91:6196–6200 (Jun., 1994). [Engelhardt II].

K Fisher et al, "Transduction with Recombinant Adeno–Associated Virus for Gene Therapy is Limited by Leading–Strand Synthesis", *J. Virol., 70*(1):520–532 (Jan., 1996).

M. Weitzman et al, "Recruitment of Wild–Type and Recombinant Adeno–Associated Virus into Adenovirus Replication Centers", *J. Virol., 70*(3):1845–1854 (Mar., 1996).

P. Nahreini et al, "Cloning and Integration of DNA Fragments in Human Cells via the Inverted Terminal Repeats of the Adeno–Associated Virus 2 Genome", *Gene, 119:*265–272 (1992).

B. Carter, "The Growth Cycle of Adeno–Associated Virus", in *CRC Handbook of Parvoviruses,* ed. P. Tijssen, vol. I, pp. 155–168 (1990).

* cited by examiner

FIG. 2A

MMTV-ORF6 Minigene

```
                                                           50
CTGCATGTGT CAGAGGTTTT CACCGTCATC ACCGAAACGC GCGAGGCAGC

                                                          100
AAGCTTGGCA GAAATGGTTG AACTCCCGAG AGTGTCCTAC ACCTAGGGGA

                                                          150
GAAGCAGCCA AGGGGTTGTT TCCCACCAAG GACGACCCGT CTGCGCACAA

                                                          200
ACGGATGAGC CCATCAGACA AAGACATATT CATTCTCTGC TGCAAACTTG

                                                          250
GCATAGCTCT GCTTTGCCTG GGGCTATTGG GGGAAGTTGC GGTTCGTGCT

                                                          300
CGCAGGGCTC TCACCCTTGA CTCTTTCAAT AATAACTCTT CTGTGCAAGA

                                                          350
TTACAATCTA AACAATTCGG AGAACTCGAC CTTCCTCCTG AGGCAAGGAC

                                                          400
CACAGCCAAC TTCCTCTTAC AAGCCGCATC GATTTTGTCC TTCAGAAATA

                                                          450
GAAATAAGAA TGCTTGCTAA AAATTATATT TTTACCAATA AGACCAATCC

                                                          500
AATAGGTAGA TTATTAGTTA CTATGTTAAG AAATGAATCA TTATCTTTTA

                                                          550
GTACTATTTT TACTCAAATT CAGAAGTTAG AAATGGGAAT AGAAAATAGA

                                                          600
AAGAGACGCT CAACCTCAAT TGAAGAACAG GTGCAAGGAC TATTGACCAC

                                                          650
AGGCCTAGAA GTAAAAAAGG GAAAAAAGAG TGTTTTTGTC AAAATAGGAG

                                                          700
ACAGGTGGTG GCAACCAGGG ACTTATAGGG GACCTTACAT CTACAGACCA

                                                          750
ACAGATGCCC CCTTACCATA TACAGGAAGA TATGACTTAA ATTGGGATAG

                                                          800
GTGGGTTACA GTCAATGGCT ATAAAGTGTT ATATAGATCC CTCCCCTTTC

                                                          850
GTGAAAGACT CGCCAGAGCT AGACCTCCTT GGTGTATGTT GTCTCAAGAA
```

Fig. 2B

```
                                                        900
AAGAAAGACG ACATGAAACA ACAGGTACAT GATTATATTT ATCTAGGAAC

                                                        950
AGGAATGCAC TTTTGGGGAA AGATTTTCCA TACCAAGGAG GGGACAGTGG

                                                       1000
CTGGACTAAT AGAACATTAT TCTGCAAAAA CTTATGGCAT GAGTTATTAT

                                                       1050
GATTAGCCTT GATTTGCCCA ACCTTGCGGT TCCCAAGGCT TAAGTAAGTT

                                                       1100
TTTGGTTACA AACTGTTCTT AAAACAAGGA TGTGAGACAA GTGGTTTCCT

                                                       1150
GACTTGGTTT GGTATCAAAG GTTCTGATCT GAGCTCTGAG TGTTCTATTT

                                                       1200
TCCTATGTTC TTTTGGAATT TATCCAAATC TTATGTAAAT GCTTATGTAA

                                                       1250
ACCAAGATAT AAAAGAGTGC TGATTTTTTG AGTAAACTTG CAACAGTCCT

                                                       1300
AACATTCACC TCTTGTGTGT TTGTGTCTGT TCGCCATCCC GTCTCCGCTC

                                                       1350
GTCACTTATC CTTCACTTTC CAGAGGGTCC CCCCGCAGAC CCCGGCGACC

                                                       1400
CTCAGGTCGG CCGACTGCGG CAGCTGGCGC CCGAACAGGG ACCCTCGGAT

                                                       1450
AAGTGACCCT TGTCTTTATT TCTACTATTT TGTGTTCGTC TTGTTTTGTC

                                                       1500
TCTATCTTGT CTGGCTATCA TCACAAGAGC GGAACGGACT CACCTCAGGG

                                                     1544
AACCAAGCTA GCCCAATTCG ATG ACT ACG TCC GGC GTT CCA TTT
                      M   T   T   S   G   V   P   F

                                                         1586
GGC ATG ACA CTA CGA CCA ACA CGA TCT CGG TTG TCT CGG CGC
G   M   T   L   R   P   T   R   S   R   L   S   R   R

                                                         1628
ACT CCG TAC AGT AGG GAT CGT CTA CCT CCT TTT GAG ACA GAA
T   P   Y   S   R   D   R   L   P   P   F   E   T   E
```

Fig. 2C

```
                                                           1670
ACC CGC GCT ACC ATA CTG GAG GAT CAT CCG CTG CTG CCC GAA
T   R   A   T   I   L   E   D   H   P   L   L   P   E

                                                           1712
TGT AAC ACT TTG ACA ATG CAC AAC GTG AGT TAC GTG CGA GGT
C   N   T   L   T   M   H   N   V   S   Y   V   R   G

                                                           1754
CTT CCC TGC AGT GTG GGA TTT ACG CTG ATT CAG GAA TGG GTT
L   P   C   S   V   G   F   T   L   I   Q   E   W   V

                                                           1796
GTT CCC TGG GAT ATG GTT CTA ACG CGG GAG GAG CTT GTA ATC
V   P   W   D   M   V   L   T   R   E   E   L   V   I

                                                           1838
CTG AGG AAG TGT ATG CAC GTG TGC CTG TGT TGT GCC AAC ATT
L   R   K   C   M   H   V   C   L   C   C   A   N   I

                                                           1880
GAT ATC ATG ACG AGC ATG ATG ATC CAT GGT TAC GAG TCC TGG
D   I   M   T   S   M   M   I   Y   G   Y   E   S   W

                                                           1922
GCT CTC CAC TGT CAT TGT TCC AGT CCC GGT TCC CTG CAG TGT
A   L   H   C   H   C   S   S   P   G   S   L   Q   C

                                                           1964
ATA GCC GGC GGG CAG GTT TTG GCC AGC TGG TTT AGG ATG GTG
I   A   G   G   Q   V   L   A   S   W   F   R   M   V

                                                           2006
GTG GAT GGC GCC ATG TTT AAT CAG AGG TTT ATA TGG TAC CGG
V   D   G   A   M   F   N   Q   R   F   I   W   Y   R

                                                           2048
GAG GTG GTG AAT TAC AAC ATG CCA AAA GAG GTA ATG TTT ATG
E   V   V   N   Y   N   M   P   K   E   V   M   F   M
```

Fig. 2D

```
                                                     2090
TCC AGC GTG TTT ATG AGG GGT CGC CAC TTA ATC TAC CTG CGC
S   S   V   F   M   R   G   R   H   L   I   Y   L   R

                                                     2132
TTG TGG TAT GAT GGC CAC GTG GGT TCT GTG GTC CCC GCC ATG
Y   W   Y   D   G   H   V   G   S   V   V   P   A   M

                                                     2174
AGC TTT GGA TAC AGC GCC TTG CAC TGT GGG ATT TTG AAC AAT
S   F   G   Y   S   A   L   H   C   G   I   L   N   N

                                                     2216
ATT GTG GTG CTG TGC TGC AGT TAC TGT GCT GAT TTA AGT GAG
I   V   V   L   C   C   S   Y   C   A   D   L   S   E

                                                     2258
ATC AGG GTG CGC TGC TGT GCC CGG AGG ACA AGG CGC CTT ATG
I   R   V   R   C   C   A   R   R   T   R   R   L   M

                                                     2300
CTG CGG GCG GTG CGA ATC ATC GCT GAG GAG ACC ACT GCC ATG
L   R   A   V   R   I   I   A   E   E   T   T   A   M

                                                     2342
TTG TAT TCC TGC AGG ACG GAG CGG CGG CGG CAG CAG TTT ATT
L   Y   S   C   R   T   E   R   R   R   Q   Q   F   I

                                                     2384
CGC GCG CTG CTG CAG CAC CAC CGC CCT ATC CTG ATG CAC GAT
R   A   L   L   Q   H   H   R   P   I   L   M   H   D

                             2410
TAT GAC TCT ACC CCC ATG TAGGGATC
Y   D   S   T   P   M

                                        2450
CAAGCTTGCG GGCGCATCGA TGATATCAAG CTTGCATGCC

                                                   2500
TGCAGGTCGA CTCTAGAGGA TCCCGGGTGG NATCCCTGTG ACCCCTCCCC

                                                   2550
AGTGCCTCTC CTGGCCCTGG AAGTTGGCAC TCCAGTGCCC ACCAGCCTTG
```

Fig. 2E

```
                                                        2600
TCCTAATAAA ATTAAGTTGN ATCATTTTGT CTGACTAGGT GTCCTTCTAT

                                                        2650
AATATTATGG GGTGGAGGGG GGTGGTATGG AGCAANGGGN AANTTGGNAA

                                                        2700
GACAANCTGT AGGGCCTGCG GGGTCTATTG GGAACAAGCT GGAGTGCAGT

                                                        2750
GGCACAATCT TGGCTCACTG CAATCTCCGC CTCCTGGGTT CAAGCGATTC

                                                        2800
TCCTGCCTCA GACTCCCGAG TTGTTGGGAT TCCAGGCATG CATGACCAGG

                                                        2850
CTCAGATAAT TTTTGTTTTT TTGGTAGAGA CGGGGTTTCA CCATATTGGN

                                                        2900
CAGGCTGGTC TCCAACTCCT AATCTCAGGT GATCTNCCCA CCTTGGCCTC

                                                        2950
CCAAATTGCT GGGATTACAG GNGTGAACCA CTGNTCCCTT CCCTGTCCTT

                                                        3000
CTGATTTTAA AATAACTATA CCAGCAGGAG GACGTCCAGA CACAGCATAG

                                                        3050
GCTACCTGGC CATGCCCAAC CGGTGGGACA TTTGAGTTGC TTGCTTGGCA

                                                        3100
CTGTCCTCTC ATGCGTTGGG TCCACTCAGT AGATGCCTGT TGAATTGGGT

                                                        3150
ACGCGGCCAG CTTGGCTGTG GAATGTGTGT CAGTTAGGGT GTGGAAAGTC

                                                        3200
CCCAGGCTCC CCAGCAGGCA GAAGTATGCA AAGCATGCAT CTCAATTAGT

                                                        3250
CAGCAACCAG GTGTGGAAAG TCCCCAGGCT CCCCAGCAGG CAGAAGTATG

                                                        3300
CAAAGCATGC ATCTCAATTA GTCAGNAACC ATAGNCCCGC CCCTAACTCC

                                                        3350
GTCCATCCCG GCCCTAACTC NGGCCAGTTC CGACCNTNCT CCGGCNNATG

                                                        3400
GNTGAGTAAT TTGCNNGATT TATGCAGNGG GCGAGGNCGC CTCGGGCTCT
```

Fig. 2F

```
                                                             3450
GAGNTNTTCC AGAAGTAGTG AGGAGGCTTT NNTGGTGGAA TTGATCAGCT

                                                             3500
TGGGATCTGA TCAAGAGACA GGATGAGGAT CGNNNCGNAT GATTGAACAA

                                                             3550
GATGGGTTGC ACGGAGGTTC TCCGGNCGCT TGGGTGGGGA GGNTATTCGG

                                                             3600
NTATTNTTGG TGNACAACAG NNAAACGGNT GTTCTGATGC CGCCGCGTTC

                                                             3650
NCGCTTTCAG NGCAGGGGGG CCCCCCTTCT NTTGAGANNA GCNCCCCTTN

TTG
```

FIG. 4A

CATCATCAAT AATATACCTT ATTTTGGATT GAAGCCAATA TGATAATGAG 50

GGGGTGGAGT TTGTGACGTG GCGCGGGGCG TGGGAACGGG GCGGGTGACG 100

TAGTAGTGTG GCGGAAGTGT GATGTTGCAA GTGTGGCGGA ACACATGTAA 150

GCGACGGATG TGGCAAAAGT GACGTTTTTG GTGTGCGCCG GTGTACACAG 200

GAAGTGACAA TTTTCGCGCG GTTTTAGGCG GATGTTGTAG TAAATTTGGG 250

CGTAACCGAG TAAGATTTGG CCATTTTCGC GGGAAAACTG AATAAGAGGA 300

AGTGAAATCT GAATAATTTT GTGTTACTCA TAGCGCGTAA TATTTGTCTA 350

GGGAGATCAG CCTGCAGGTC GTTACATAAC TTACGGTAAA TGGCCCGCCT 400

GGCTGACCGC CCAACGACCC CCGCCCATTG ACGTCAATAA TGACGTATGT 450

TCCCATAGTA ACGCCAATAG GGACTTTCCA TTGACGTCAA TGGGTGGAGT 500

ATTTACGGTA AACTGCCCAC TTGGCAGTAC ATCAAGTGTA TCATATGCCA 550

AGTACGCCCC CTATTGACGT CAATGACGGT AAATGGCCCG CCTGGCATTA 600

TGCCCAGTAC ATGACCTTAT GGGACTTTCC TACTTGGCAG TACATCTACT 650

CGAGGCCACG TTCTGCTTCA CTCTCCCCAT CTCCCCCCCC TCCCCACCCC 700

CAATTTTGTA TTTATTTATT TTTTAATTAT TTTGTGCAGC GATGGGGGCG 750

GGGGGGGGGG GGGGGCGCGC GCCAGGCGGG GCGGGGCGGG GCGAGGGGCG 800

GGGCGGGGCG AGGCGGAGAG GTGCGGCGGC AGCCAATCAG AGCGGCGCGC 850

TCCGAAAGTT TCCTTTTATG GCGAGGCGGC GGCGGCGGCG GCCCTATAAA 900

AAGCGAAGCG CGCGGCGGGC GGGAGCGGGA TCAGCCACCG CGGTGGCGGC 950

CGCAATTCCC GGGGATCGAA AGAGCCTGCT AAAGCAAAAA AGAAGTCACC 1000

ATGTCGTTTA CTTTGACCAA CAAGAACGTG ATTTTCGTTG CCGGTCTGGG 1050

AGGCATTGGT CTGGACACCA GCAAGGAGCT GCTCAAGCGC GATCCCGTCG 1100

TTTTACAACG TCGTGACTGG GAAAACCCTG GCGTTACCCA ACTTAATCGC 1150

CTTGCAGCAC ATCCCCCTTT CGCCAGCTGG CGTAATAGCG AAGAGGCCCG 1200

FIG. 4B

```
CACCGATCGC CCTTCCCAAC AGTTGCGCAG CCTGAATGGC GAATGGCGCT  1250
TTGCCTGGTT TCCGGCACCA GAAGCGGTGC CGGAAAGCTG GCTGGAGTGC  1300
GATCTTCCTG AGGCCGATAC TGTCGTCGTC CCCTCAAACT GGCAGATGCA  1350
CGGTTACGAT GCGCCCATCT ACACCAACGT AACCTATCCC ATTACGGTCA  1400
ATCCGCCGTT TGTTCCCACG GAGAATCCGA CGGGTTGTTA CTCGCTCACA  1450
TTTAATGTTG ATGAAAGCTG GCTACAGGAA GGCCAGACGC GAATTATTTT  1500
TGATGGCGTT AACTCGGCGT TTCATCTGTG GTGCAACGGG CGCTGGGTCG  1550
GTTACGGCCA GGACAGTCGT TTGCCGTCTG AATTTGACCT GAGCGCATTT  1600
TTACGCGCCG GAGAAAACCG CCTCGCGGTG ATGGTGCTGC GTTGGAGTGA  1650
CGGCAGTTAT CTGGAAGATC AGGATATGTG GCGGATGAGC GGCATTTTCC  1700
GTGACGTCTC GTTGCTGCAT AAACCGACTA CACAAATCAG CGATTTCCAT  1750
GTTGCCACTC GCTTTAATGA TGATTTCAGC CGCGCTGTAC TGGAGGCTGA  1800
AGTTCAGATG TGCGGCGAGT TGCGTGACTA CCTACGGGTA ACAGTTTCTT  1850
TATGGCAGGG TGAAACGCAG GTCGCCAGCG GCACCGCGCC TTTCGGCGGT  1900
      Cla I (1907)
GAAATTATCG ATGAGCGTGG TGGTTATGCC GATCGCGTCA CACTACGTCT  1950
GAACGTCGAA AACCCGAAAC TGTGGAGCGC CGAAATCCCG AATCTCTATC  2000
GTGCGGTGGT TGAACTGCAC ACCGCCGACG GCACGCTGAT TGAAGCAGAA  2050
GCCTGCGATG TCGGTTTCCG CGAGGTGCGG ATTGAAAATG GTCTGCTGCT  2100
GCTGAACGGC AAGCCGTTGC TGATTCGAGG CGTTAACCGT CACGAGCATC  2150
ATCCTCTGCA TGGTCAGGTC ATGGATGAGC AGACGATGGT GCAGGATATC  2200
CTGCTGATGA AGCAGAACAA CTTTAACGCC GTGCGCTGTT CGCATTATCC  2250
GAACCATCCG CTGTGGTACA CGCTGTGCGA CCGCTACGGC CTGTATGTGG  2300
TGGATGAAGC CAATATTGAA ACCCACGGCA TGGTGCCAAT GAATCGTCTG  2350
ACCGATGATC CGCGCTGGCT ACCGGCGATG AGCGAACGCG TAACGCGAAT  2400
```

FIG. 4C

```
GGTGCAGCGC GATCGTAATC ACCCGAGTGT GATCATCTGG TCGCTGGGGA  2450
ATGAATCAGG CCACGGCGCT AATCACGACG CGCTGTATCG CTGGATCAAA  2500
TCTGTCGATC CTTCCCGCCC GGTGCAGTAT GAAGGCGGCG GAGCCGACAC  2550
CACGGCCACC GATATTATTT GCCCGATGTA CGCGCGCGTG GATGAAGACC  2600
AGCCCTTCCC GGCTGTGCCG AAATGGTCCA TCAAAAAATG GCTTTCGCTA  2650
CCTGGAGAGA CGCGCCCGCT GATCCTTTGC GAATACGCCC ACGCGATGGG  2700
TAACAGTCTT GGCGGTTTCG CTAAATACTG GCAGGCGTTT CGTCAGTATC  2750
CCCGTTTACA GGGCGGCTTC GTCTGGGACT GGGTGGATCA GTCGCTGATT  2800
AAATATGATG AAAACGGCAA CCCGTGGTCG GCTTACGGCG GTGATTTTGG  2850
CGATACGCCG AACGATCGCC AGTTCTGTAT GAACGGTCTG GTCTTTGCCG  2900
ACCGCACGCC GCATCCAGCG CTGACGGAAG CAAAACACCA GCAGCAGTTT  2950
TTCCAGTTCC GTTTATCCGG GCAAACCATC GAAGTGACCA GCGAATACCT  3000
GTTCCGTCAT AGCGATAACG AGCTCCTGCA CTGGATGGTG GCGCTGGATG  3050
GTAAGCCGCT GGCAAGCGGT GAAGTGCCTC TGGATGTCGC TCCACAAGGT  3100
AAACAGTTGA TTGAACTGCC TGAACTACCG CAGCCGGAGA GCGCCGGGCA  3150
ACTCTGGCTC ACAGTACGCG TAGTGCAACC GAACGCGACC GCATGGTCAG  3200
AAGCCGGGCA CATCAGCGCC TGGCAGCAGT GGCGTCTGGC GGAAAACCTC  3250
AGTGTGACGC TCCCCGCCGC GTCCCACGCC ATCCCGCATC TGACCACCAG  3300
CGAAATGGAT TTTTGCATCG AGCTGGGTAA TAAGCGTTGG CAATTTAACC  3350
GCCAGTCAGG CTTTCTTTCA CAGATGTGGA TTGGCGATAA AAAACAACTG  3400
CTGACGCCGC TGCGCGATCA GTTCACCCGT GCACCGCTGG ATAACGACAT  3450
TGGCGTAAGT GAAGCGACCC GCATTGACCC TAACGCCTGG GTCGAACGCT  3500
GGAAGGCGGC GGGCCATTAC CAGGCCGAAG CAGCGTTGTT GCAGTGCACG  3550
GCAGATACAC TTGCTGATGC GGTGCTGATT ACGACCGCTC ACGCGTGGCA  3600
GCATCAGGGG AAAACCTTAT TTATCAGCCG GAAAACCTAC CGGATTGATG  3650
```

FIG. 4D

```
GTAGTGGTCA AATGGCGATT ACCGTTGATG TTGAAGTGGC GAGCGATACA  3700
CCGCATCCGG CGCGGATTGG CCTGAACTGC CAGCTGGCGC AGGTAGCAGA  3750
GCGGGTAAAC TGGCTCGGAT TAGGGCCGCA AGAAAACTAT CCCGACCGCC  3800
TTACTGCCGC CTGTTTTGAC CGCTGGGATC TGCCATTGTC AGACATGTAT  3850
ACCCCGTACG TCTTCCCGAG CGAAAACGGT CTGCGCTGCG GGACGCGCGA  3900
ATTGAATTAT GGCCCACACC AGTGGCGCGG CGACTTCCAG TTCAACATCA  3950
GCCGCTACAG TCAACAGCAA CTGATGGAAA CCAGCCATCG CCATCTGCTG  4000
CACGCGGAAG AAGGCACATG GCTGAATATC GACGGTTTCC ATATGGGGAT  4050
TGGTGGCGAC GACTCCTGGA GCCCGTCAGT ATCGGCGGAA TTACAGCTGA  4100
GCGCCGGTCG CTACCATTAC CAGTTGGTCT GGTGTCAAAA ATAATAATAA  4150
CCGGGCAGGC CATGTCTGCC CGTATTTCGC GTAAGGAAAT CCATTATGTA  4200
CTATTTAAAA AACACAAACT TTTGGATGTT CGGTTTATTC TTTTTCTTTT  4250
ACTTTTTTAT CATGGGAGCC TACTTCCCGT TTTTCCCGAT TTGGCTACAT  4300
GACATCAACC ATATCAGCAA AAGTGATACG GGTATTATTT TTGCCGCTAT  4350
TTCTCTGTTC TCGCTATTAT TCCAACCGCT GTTTGGTCTG CTTTCTGACA  4400

                                   BamHI (4430)
AACTCGGCCT CGACTCTAGG CGGCCGCGGG GATCCAGACA TGATAAGATA  4450
CATTGATGAG TTTGGACAAA CCACAACTAG AATGCAGTGA AAAAAATGCT  4500
TTATTTGTGA AATTTGTGAT GCTATTGCTT TATTTGTAAC CATTATAAGC  4550
TGCAATAAAC AAGTTAACAA CAACAATTGC ATTCATTTTA TGTTTCAGGT  4600

                                BamHI (4628) SalI (4640)
TCAGGGGGAG GTGTGGGAGG TTTTTTCGGA TCCTCTAGAG TCGACCTGCA  4650
                                      XbaI (4634)
GGCTGATCAG TGGAAGGTGC TGAGGTACGA TGAGACCCGC ACCAGGTGCA  4700
GACCCTGCGA GTGTGGCGGT AAACATATTA GGAACCAGCC TGTGATGCTG  4750
GATGTGACCG AGGAGCTGAG GCCCGATCAC TTGGTGCTGG CCTGCACCCG  4800
```

FIG. 4E

```
CGCTGAGTTT GGCTCTAGCG ATGAAGATAC AGATTGAGGT ACTGAAATGT  4850
GTGGGCGTGG CTTAAGGGTG GGAAAGAATA TATAAGGTGG GGGTCTTATG  4900
TAGTTTTGTA TCTGTTTTGC AGCAGCCGCC GCCGCCATGA GCACCAACTC  4950
GTTTGATGGA AGCATTGTGA GCTCATATTT GACAACGCGC ATGCCCCCAT  5000
GGGCCGGGGT GCGTCAGAAT GTGATGGGCT CCAGCATTGA TGGTCGCCCC  5050
GTCCTGCCCG CAAACTCTAC TACCTTGACC TACGAGACCG TGTCTGGAAC  5100
GCCGTTGGAG ACTGCAGCCT CCGCCGCCGC TTCAGCCGCT GCAGCCACCG  5150
CCCGCGGGAT TGTGACTGAC TTTGCTTTCC TGAGCCCGCT TGCAAGCAGT  5200
GCAGCTTCCC GTTCATCCGC CCGCGATGAC AAGTTGACGG CTCTTTTGGC  5250
ACAATTGGAT TCTTTGACCC GGGAACTTAA TGTCGTTTCT CAGCAGCTGT  5300
TGGATCTGCG CCAGCAGGTT TCTGCCCTGA AGGCTTCCTC CCCTCCCAAT  5350
GCGGTTTAAA ACATAAATAA AAAACCAGAC TCTGTTTGGA TTTGGATCAA  5400
GCAAGTGTCT TGCTGTCTTT ATTTAGGGGT TTTGCGCGCG CGGTAGGCCC  5450
GGGACCAGCG GTCTCGGTCG TTGAGGGTCC TGTGTATTTT TTCCAGGACG  5500
TGGTAAAGGT GACTCTGGAT GTTCAGATAC ATGGGCATAA GCCCGTCTCT  5550
GGGGTGGAGG TAGCACCACT GCAGAGCTTC ATGCTGCGGG GTGGTGTTGT  5600
AGATGATCCA GTCGTAGCAG GAGCGCTGGG CGTGGTGCCT AAAAATGTCT  5650
TTCAGTAGCA AGCTGATTGC CAGGGGCAGG CCCTTGGTGT AAGTGTTTAC  5700
AAAGCGGTTA AGCTGGGATG GGTGCATACG TGGGGATATG AGATGCATCT  5750
TGGACTGTAT TTTTAGGTTG GCTATGTTCC CAGCCATATC CCTCCGGGGA  5800
TTCATGTTGT GCAGAACCAC CAGCACAGTG TATCCGGTGC ACTTGGGAAA  5850
TTTGTCATGT AGCTTAGAAG GAAATGCGTG GAAGAACTTG GAGACGCCCT  5900
TGTGACCTCC AAGATTTTCC ATGCATTCGT CCATAATGAT GGCAATGGGC  5950
CCACGGGCGG CGGCCTGGGC GAAGATATTT CTGGGATCAC TAACGTCATA  6000
GTTGTGTTCC AGGATGAGAT CGTCATAGGC CATTTTTACA AAGCGCGGGC  6050
```

FIG. 4F

```
GGAGGGTGCC AGACTGCGGT ATAATGGTTC CATCCGGCCC AGGGGCGTAG   6100
TTACCCTCAC AGATTTGCAT TTCCCACGCT TTGAGTTCAG ATGGGGGGAT   6150
CATGTCTACC TGCGGGGCGA TGAAGAAAAC GGTTTCCGGG GTAGGGGAGA   6200
TCAGCTGGGA AGAAAGCAGG TTCCTGAGCA GCTGCGACTT ACCGCAGCCG   6250
GTGGGCCCGT AAATCACACC TATTACCGGG TGCAACTGGT AGTTAAGAGA   6300
GCTGCAGCTG CCGTCATCCC TGAGCAGGGG GGCCACTTCG TTAAGCATGT   6350
CCCTGACTCG CATGTTTTCC CTGACCAAAT CCGCCAGAAG GCGCTCGCCG   6400
CCCAGCGATA GCAGTTCTTG CAAGGAAGCA AAGTTTTTCA ACGGTTTGAG   6450
ACCGTCCGCC GTAGGCATGC TTTTGAGCGT TTGACCAAGC AGTTCCAGGC   6500
GGTCCCACAG CTCGGTCACC TGCTCTACGG CATCTCGATC CAGCATATCT   6550
CCTCGTTTCG CGGGTTGGGG CGGCTTTCGC TGTACGGCAG TAGTCGGTGC   6600
TCGTCCAGAC GGGCCAGGGT CATGTCTTTC CACGGGCGCA GGGTCCTCGT   6650
CAGCGTAGTC TGGGTCACGG TGAAGGGGTG CGCTCCGGGC TGCGCGCTGG   6700
CCAGGGTGCG CTTGAGGCTG GTCCTGCTGG TGCTGAAGCG CTGCCGGTCT   6750
TCGCCCTGCG CGTCGGCCAG GTAGCATTTG ACCATGGTGT CATAGTCCAG   6800
CCCCTCCGCG GCGTGGCCCT TGGCGCGCAG CTTGCCCTTG GAGGAGGCGC   6850
CGCACGAGGG GCAGTGCAGA CTTTTGAGGG CGTAGAGCTT GGGCGCGAGA   6900
AATACCGATT CCGGGGAGTA GGCATCCGCG CCGCAGGCCC CGCAGACGGT   6950
CTCGCATTCC ACGAGCCAGG TGAGCTCTGG CCGTTCGGGG TCAAAAACCA   7000
GGTTTCCCCC ATGCTTTTTG ATGCGTTTCT TACCTCTGGT TTCCATGAGC   7050
CGGTGTCCAC GCTCGGTGAC GAAAAGGCTG TCCGTGTCCC CGTATACAGA   7100
CTTGAGAGGC CTGTCCTCGA GCGGTGTTCC GCGGTCCTCC TCGTATAGAA   7150
ACTCGGACCA CTCTGAGACA AAGGCTCGCG TCCAGGCCAG CACGAAGGAG   7200
GCTAAGTGGG AGGGGTAGCG GTCGTTGTCC ACTAGGGGGT CCACTCGCTC   7250
CAGGGTGTGA AGACACATGT CGCCCTCTTC GGCATCAAGG AAGGTGATTG   7300
```

FIG. 4G

```
GTTTGTAGGT GTAGGCCACG TGACCGGGTG TTCCTGAAGG GGGGCTATAA  7350
AAGGGGGTGG GGGCGCGTTC GTCCTCACTC TCTTCCGCAT CGCTGTCTGC  7400
GAGGGCCAGC TGTTGGGGTG AGTACTCCCT CTGAAAAGCG GGCATGACTT  7450
CTGCGCTAAG ATTGTCAGTT TCCAAAAACG AGGAGGATTT GATATTCACC  7500
TGGCCCGCGG TGATGCCTTT GAGGGTGGCC GCATCCATCT GGTCAGAAAA  7550
GACAATCTTT TTGTTGTCAA GCTTGGTGGC AAACGACCCG TAGAGGGCGT  7600
TGGACAGCAA CTTGGCGATG GAGCGCAGGG TTTGGTTTTT GTCGCGATCG  7650
GCGCGCTCCT TGGCCGCGAT GTTTAGCTGC ACGTATTCGC GCGCAACGCA  7700
CCGCCATTCG GGAAAGACGG TGGTGCGCTC GTCGGGCACC AGGTGCACGC  7750
GCCAACCGCG GTTGTGCAGG GTGACAAGGT CAACGCTGGT GGCTACCTCT  7800
CCGCGTAGGC GCTCGTTGGT CCAGCAGAGG CGGCCGCCCT TGCGCGAGCA  7850
GAATGGCGGT AGGGGGTCTA GCTGCGTCTC GTCCGGGGGG TCTGCGTCCA  7900
CGGTAAAGAC CCCGGGCAGC AGGCGCGCGT CGAAGTAGTC TATCTTGCAT  7950
CCTTGCAAGT CTAGCGCCTG CTGCCATGCG CGGGCGGCAA GCGCGCGCTC  8000
GTATGGGTTG AGTGGGGGAC CCCATGGCAT GGGGTGGGTG AGCGCGGAGG  8050
CGTACATGCC GCAAATGTCG TAAACGTAGA GGGGCTCTCT GAGTATTCCA  8100
AGATATGTAG GGTAGCATCT TCCACCGCGG ATGCTGGCGC GCACGTAATC  8150
GTATAGTTCG TGCGAGGGAG CGAGGAGGTC GGGACCGAGG TTGCTACGGG  8200
CGGGCTGCTC TGCTCGGAAG ACTATCTGCC TGAAGATGGC ATGTGAGTTG  8250
GATGATATGG TTGGACGCTG GAAGACGTTG AAGCTGGCGT CTGTGAGACC  8300
TACCGCGTCA CGCACGAAGG AGGCGTAGGA GTCGCGCAGC TTGTTGACCA  8350
GCTCGGCGGT GACCTGCACG TCTAGGGCGC AGTAGTCCAG GGTTTCCTTG  8400
ATGATGTCAT ACTTATCCTG TCCCTTTTTT TTCCACAGCT CGCGGTTGAG  8450
GACAAACTCT TCGCGGTCTT TCCAGTACTC TTGGATCGGA AACCCGTCGG  8500
CCTCCGAACG GTAAGAGCCT AGCATGTAGA ACTGGTTGAC GGCCTGGTAG  8550
```

FIG. 4H

```
GCGCAGCATC CCTTTTCTAC GGGTAGCGCG TATGCCTGCG CGGCCTTCCG  8600
GAGCGAGGTG TGGGTGAGCG CAAAGGTGTC CCTGACCATG ACTTTGAGGT  8650
ACTGGTATTT GAAGTCAGTG TCGTCGCATC CGCCCTGCTC CCAGAGCAAA  8700
AAGTCCGTGC GCTTTTTGGA ACGCGGATTT GGCAGGGCGA AGGTGACATC  8750
GTTGAAGAGT ATCTTTCCCG CGCGAGGCAT AAAGTTGCGT GTGATGCGGA  8800
AGGGTCCCGG CACCTCGGAA CGGTTGTTAA TTACCTGGGC GGCGAGCACG  8850
ATCTCGTCAA AGCCGTTGAT GTTGTGGCCC ACAATGTAAA GTTCCAAGAA  8900
GCGCGGGATG CCCTTGATGG AAGGCAATTT TTTAAGTTCC TCGTAGGTGA  8950
GCTCTTCAGG GGAGCTGAGC CCGTGCTCTG AAAGGGCCCA GTCTGCAAGA  9000
TGAGGGTTGG AAGCGACGAA TGAGCTCCAC AGGTCACGGG CCATTAGCAT  9050
TTGCAGGTGG TCGCGAAAGG TCCTAAACTG GCGACCTATG GCCATTTTTT  9100
CTGGGGTGAT GCAGTAGAAG GTAAGCGGGT CTTGTTCCCA GCGGTCCCAT  9150
CCAAGGTTCG CGGCTAGGTC TCGCGCGGCA GTCACTAGAG GCTCATCTCC  9200
GCCGAACTTC ATGACCAGCA TGAAGGGCAC GAGCTGCTTC CCAAAGGCCC  9250
CCATCCAAGT ATAGGTCTCT ACATCGTAGG TGACAAAGAG ACGCTCGGTG  9300
CGAGGATGCG AGCCGATCGG GAAGAACTGG ATCTCCCGCC ACCAATTGGA  9350
GGAGTGGCTA TTGATGTGGT GAAAGTAGAA GTCCCTGCGA CGGGCCGAAC  9400
ACTCGTGCTG GCTTTTGTAA AAACGTGCGC AGTACTGGCA GCGGTGCACG  9450
GGCTGTACAT CCTGCACGAG GTTGACCTGA CGACCGCGCA CAAGGAAGCA  9500
GAGTGGGAAT TTGAGCCCCT CGCCTGGCGG GTTTGGCTGG TGGTCTTCTA  9550
CTTCGGCTGC TTGTCCTTGA CCGTCTGGCT GCTCGAGGGG AGTTACGGTG  9600
GATCGGACCA CCACGCCGCG CGAGCCCAAA GTCCAGATGT CCGCGCGCGG  9650
CGGTCGGAGC TTGATGACAA CATCGCGCAG ATGGGAGCTG TCCATGGTCT  9700
GGAGCTCCCG CGGCGTCAGG TCAGGCGGGA GCTCCTGCAG GTTTACCTCG  9750
CATAGACGGG TCAGGGCGCG GGCTAGATCC AGGTGATACC TAATTTCCAG  9800
```

FIG. 4I

```
GGGCTGGTTG GTGGCGGCGT CGATGGCTTG CAAGAGGCCG CATCCCCGCG  9850
GCGCGACTAC GGTACCGCGC GGCGGGCGGT GGGCCGCGGG GGTGTCCTTG  9900
GATGATGCAT CTAAAAGCGG TGACGCGGGC GAGCCCCCGG AGGTAGGGGG  9950
GGCTCCGGAC CCGCCGGGAG AGGGGGCAGG GGCACGTCGG CGCCGCGCGC 10000
GGGCAGGAGC TGGTGCTGCG CGCGTAGGTT GCTGGCGAAC GCGACGACGC 10050
GGCGGTTGAT CTCCTGAATC TGGCGCCTCT GCGTGAAGAC GACGGGCCCG 10100
GTGAGCTTGA GCCTGAAAGA GAGTTCGACA GAATCAATTT CGGTGTCGTT 10150
GACGGCGGCC TGGCGCAAAA TCTCCTGCAC GTCTCCTGAG TTGTCTTGAT 10200
AGGCGATCTC GGCCATGAAC TGCTCGATCT CTTCCTCCTG GAGATCTCCG 10250
CGTCCGGCTC GCTCCACGGT GGCGGCGAGG TCGTTGGAAA TGCGGGCCAT 10300
GAGCTGCGAG AAGGCGTTGA GGCCTCCCTC GTTCCAGACG CGGCTGTAGA 10350
CCACGCCCCC TTCGGCATCG CGGGCGCGCA TGACCACCTG CGCGAGATTG 10400
AGCTCCACGT GCCGGGCGAA GACGGCGTAG TTTCGCAGGC GCTGAAAGAG 10450
GTAGTTGAGG GTGGTGGCGG TGTGTTCTGC CACGAAGAAG TACATAACCC 10500
AGCGTCGCAA CGTGGATTCG TTGATATCCC CCAAGGCCTC AAGGCGCTCC 10550
ATGGCCTCGT AGAAGTCCAC GGCGAAGTTG AAAAACTGGG AGTTGCGCGC 10600
CGACACGGTT AACTCCTCCT CCAGAAGACG GATGAGCTCG GCGACAGTGT 10650
CGCGCACCTC GCGCTCAAAG GCTACAGGGG CCTCTTCTTC TTCTTCAATC 10700
TCCTCTTCCA TAAGGGCCTC CCCTTCTTCT TCTTCTGGCG GCGGTGGGGG 10750
                                          SalI (10790)
AGGGGGGACA CGGCGGCGAC GACGGCGCAC CGGGAGGCGG TCGACAAAGC 10800
GCTCGATCAT CTCCCCGCGG CGACGGCGCA TGGTCTCGGT GACGGCGCGG 10850
CCGTTCTCGC GGGGGCGCAG TTGGAAGACG CCGCCCGTCA TGTCCCGGTT 10900
ATGGGTTGGC GGGGGGCTGC CATGCGGCAG GGATACGGCG CTAACGATGC 10950
ATCTCAACAA TTGTTGTGTA GGTACTCCGC CGCCGAGGGA CCTGAGCGAG 11000
```

FIG. 4J

TCCGCATCGA CCGGATCGGA AAACCTCTCG AGAAAGGCGT CTAACCAGTC 11050

ACAGTCGCAA GGTAGGCTGA GCACCGTGGC GGGCGGCAGC GGGCGGCGGT 11100

CGGGGTTGTT TCTGGCGGAG GTGCTGCTGA TGATGTAATT AAAGTAGGCG 11150

SalI (11169)
GTCTTGAGAC GGCGGATGGT CGACAGAAGC ACCATGTCCT TGGGTCCGGC 11200

CTGCTGAATG CGCAGGCGGT CGGCCATGCC CCAGGCTTCG TTTTGACATC 11250

GGCGCAGGTC TTTGTAGTAG TCTTGCATGA GCCTTTCTAC CGGCACTTCT 11300

TCTTCTCCTT CCTCTTGTCC TGCATCTCTT GCATCTATCG CTGCGGCGGC 11350

GGCGGAGTTT GGCCGTAGGT GGCGCCCTCT TCCTCCCATG CGTGTGACCC 11400

CGAAGCCCCT CATCGGCTGA AGCAGGGCTA GGTCGGCGAC AACGCGCTCG 11450

GCTAATATGG CCTGCTGCAC CTGCGTGAGG GTAGACTGGA AGTCATCCAT 11500

GTCCACAAAG CGGTGGTATG CGCCCGTGTT GATGGTGTAA GTGCAGTTGG 11550

CCATAACGGA CCAGTTAACG GTCTGGTGAC CCGGCTGCGA GAGCTCGGTG 11600

TACCTGAGAC GCGAGTAAGC CCTCGAGTCA AATACGTAGT CGTTGCAAGT 11650

CCGCACCAGG TACTGGTATC CCACCAAAAA GTGCGGCGGC GGCTGGCGGT 11700

AGAGGGGCCA GCGTAGGGTG GCCGGGGCTC CGGGGGCGAG ATCTTCCAAC 11750

ATAAGGCGAT GATATCCGTA GATGTACCTG GACATCCAGG TGATGCCGGC 11800

GGCGGTGGTG GAGGCGCGCG GAAAGTCGCG GACGCGGTTC CAGATGTTGC 11850

GCAGCGGCAA AAAGTGCTCC ATGGTCGGGA CGCTCTGGCC GGTCAGGCGC 11900

XbaI (11917)
GCGCAATCGT TGACGCTCTA GACCGTGCAA AAGGAGAGCC TGTAAGCGGG 11950

CACTCTTCCG TGGTCTGGTG GATAAATTCG CAAGGGTATC ATGGCGGACG 12000

ACCGGGGTTC GAGCCCCGTA TCCGGCCGTC CGCCGTGATC CATGCGGTTA 12050

CCGCCCGCGT GTCGAACCCA GGTGTGCGAC GTCAGACAAC GGGGGAGTGC 12100

TCCTTTTGGC TTCCTTCCAG GCGCGGCGGC TGCTGCGCTA GCTTTTTTGG 12150

CCACTGGCCG CGCGCAGCGT AAGCGGTTAG GCTGGAAAGC GAAAGCATTA 12200

FIG. 4K

```
AGTGGCTCGC TCCCTGTAGC CGGAGGGTTA TTTTCCAAGG GTTGAGTCGC 12250
GGGACCCCCG GTTCGAGTCT CGGACCGGCC GGACTGCGGC GAACGGGGGT 12300
TTGCCTCCCC GTCATGCAAG ACCCCGCTTG CAAATTCCTC CGGAAACAGG 12350
GACGAGCCCC TTTTTTGCTT TTCCCAGATG CATCCGGTGC TGCGGCAGAT 12400
GCGCCCCCCT CCTCAGCAGC GGCAAGAGCA AGAGCAGCGG CAGACATGCA 12450
GGGCACCCTC CCCTCCTCCT ACCGCGTCAG GAGGGGCGAC ATCCGCGGTT 12500
GACGCGGCAG CAGATGGTGA TTACGAACCC CCGCGGCGCC GGGCCCGGCA 12550
CTACCTGGAC TTGGAGGAGG GCGAGGGCCT GGCGCGGCTA GGAGCGCCCT 12600
CTCCTGAGCG GTACCCAAGG GTGCAGCTGA AGCGTGATAC GCGTGAGGCG 12650
TACGTGCCGC GGCAGAACCT GTTTCGCGAC CGCGAGGGAG AGGAGCCCGA 12700
GGAGATGCGG GATCGAAAGT TCCACGCAGG GCGCGAGCTG CGGCATGGCC 12750
TGAATCGCGA GCGGTTGCTG CGCGAGGAGG ACTTTGAGCC CGACGCGCGA 12800
ACCGGGATTA GTCCCGCGCG CGCACACGTG GCGGCCGCCG ACCTGGTAAC 12850
CGCATACGAG CAGACGGTGA ACCAGGAGAT TAACTTTCAA AAAAGCTTTA 12900
ACAACCACGT GCGTACGCTT GTGGCGCGCG AGGAGGTGGC TATAGGACTG 12950
ATGCATCTGT GGGACTTTGT AAGCGCGCTG GAGCAAAACC CAAATAGCAA 13000
GCCGCTCATG GCGCAGCTGT TCCTTATAGT GCAGCACAGC AGGGACAACG 13050
AGGCATTCAG GGATGCGCTG CTAAACATAG TAGAGCCCGA GGGCCGCTGG 13100
CTGCTCGATT TGATAAACAT CCTGCAGAGC ATAGTGGTGC AGGAGCGCAG 13150
CTTGAGCCTG GCTGACAAGG TGGCCGCCAT CAACTATTCC ATGCTTAGCC 13200
TGGGCAAGTT TTACGCCCGC AAGATATACC ATACCCCTTA CGTTCCCATA 13250
GACAAGGAGG TAAAGATCGA GGGGTTCTAC ATGCGCATGG CGCTGAAGGT 13300
GCTTACCTTG AGCGACGACC TGGGCGTTTA TCGCAACGAG CGCATCCACA 13350
AGGCCGTGAG CGTGAGCCGG CGGCGCGAGC TCAGCGACCG CGAGCTGATG 13400
CACAGCCTGC AAAGGGCCCT GGCTGGCACG GGCAGCGGCG ATAGAGAGGC 13450
```

FIG. 4L

```
CGAGTCCTAC TTTGACGCGG GCGCTGACCT GCGCTGGGCC CCAAGCCGAC 13500
GCGCCCTGGA GGCAGCTGGG GCCGGACCTG GGCTGGCGGT GGCACCCGCG 13550
CGCGCTGGCA ACGTCGGCGG CGTGGAGGAA TATGACGAGG ACGATGAGTA 13600
CGAGCCAGAG GACGGCGAGT ACTAAGCGGT GATGTTTCTG ATCAGATGAT 13650
GCAAGACGCA ACGGACCCGG CGGTGCGGGC GGCGCTGCAG AGCCAGCCGT 13700
CCGGCCTTAA CTCCACGGAC GACTGGCGCC AGGTCATGGA CCGCATCATG 13750
TCGCTGACTG CGCGCAATCC TGACGCGTTC CGGCAGCAGC CGCAGGCCAA 13800
CCGGCTCTCC GCAATTCTGG AAGCGGTGGT CCCGGCGCGC GCAAACCCCA 13850
CGCACGAGAA GGTGCTGGCG ATCGTAAACG CGCTGGCCGA AAACAGGGCC 13900
ATCCGGCCCG ACGAGGCCGG CCTGGTCTAC GACGCGCTGC TTCAGCGCGT 13950
GGCTCGTTAC AACAGCGGCA ACGTGCAGAC CAACCTGGAC CGGCTGGTGG 14000
GGGATGTGCG CGAGGCCGTG GCGCAGCGTG AGCGCGCGCA GCAGCAGGGC 14050
AACCTGGGCT CCATGGTTGC ACTAAACGCC TTCCTGAGTA CACAGCCCGC 14100
CAACGTGCCG CGGGGACAGG AGGACTACAC CAACTTTGTG AGCGCACTGC 14150
GGCTAATGGT GACTGAGACA CCGCAAAGTG AGGTGTACCA GTCTGGGCCA 14200
GACTATTTTT TCCAGACCAG TAGACAAGGC CTGCAGACCG TAAACCTGAG 14250
CCAGGCTTTC AAAAACTTGC AGGGGCTGTG GGGGGTGCGG GCTCCCACAG 14300
GCGACCGCGC GACCGTGTCT AGCTTGCTGA CGCCCAACTC GCGCCTGTTG 14350
CTGCTGCTAA TAGCGCCCTT CACGGACAGT GGCAGCGTGT CCCGGGACAC 14400
ATACCTAGGT CACTTGCTGA CACTGTACCG CGAGGCCATA GGTCAGGCGC 14450
ATGTGGACGA GCATACTTTC CAGGAGATTA CAAGTGTCAG CCGCGCGCTG 14500
GGGCAGGAGG ACACGGGCAG CCTGGAGGCA ACCCTAAACT ACCTGCTGAC 14550
CAACCGGCGG CAGAAGATCC CCTCGTTGCA CAGTTTAAAC AGCGAGGAGG 14600
AGCGCATTTT GCGCTACGTG CAGCAGAGCG TGAGCCTTAA CCTGATGCGC 14650
GACGGGGTAA CGCCCAGCGT GGCGCTGGAC ATGACCGCGC GCAACATGGA 14700
```

FIG. 4M

```
ACCGGGCATG TATGCCTCAA ACCGGCCGTT TATCAACCGC CTAATGGACT 14750
ACTTGCATCG CGCGGCCGCC GTGAACCCCG AGTATTTCAC CAATGCCATC 14800
TTGAACCCGC ACTGGCTACC GCCCCCTGGT TTCTACACCG GGGGATTCGA 14850
GGTGCCCGAG GGTAACGATG GATTCCTCTG GGACGACATA GACGACAGCG 14900
TGTTTTCCCC GCAACCGCAG ACCCTGCTAG AGTTGCAACA GCGCGAGCAG 14950
GCAGAGGCGG CGCTGCGAAA GGAAAGCTTC CGCAGGCCAA GCAGCTTGTC 15000
CGATCTAGGC GCTGCGGCCC CGCGGTCAGA TGCTAGTAGC CCATTTCCAA 15050
GCTTGATAGG GTCTCTTACC AGCACTCGCA CCACCCGCCC GCGCCTGCTG 15100
GGCGAGGAGG AGTACCTAAA CAACTCGCTG CTGCAGCCGC AGCGCGAAAA 15150
AAACCTGCCT CCGGCATTTC CCAACAACGG GATAGAGAGC CTAGTGGACA 15200
AGATGAGTAG ATGGAAGACG TACGCGCAGG AGCACAGGGA CGTGCCAGGC 15250
CCGCGCCCGC CCACCCGTCG TCAAAGGCAC GACCGTCAGC GGGGTCTGGT 15300
GTGGGAGGAC GATGACTCGG CAGACGACAG CAGCGTCCTG GATTTGGGAG 15350
GGAGTGGCAA CCCGTTTGCG CACCTTCGCC CCAGGCTGGG GAGAATGTTT 15400
TAAAAAAAAA AAAGCATGAT GCAAAATAAA AAACTCACCA AGGCCATGGC 15450
ACCGAGCGTT GGTTTTCTTG TATTCCCCTT AGTATGCGGC GCGCGGCGAT 15500
GTATGAGGAA GGTCCTCCTC CCTCCTACGA GAGTGTGGTG AGCGCGGCGC 15550
CAGTGGCGGC GGCGCTGGGT TCTCCCTTCG ATGCTCCCCT GGACCCGCCG 15600
TTTGTGCCTC CGCGGTACCT GCGGCCTACC GGGGGGAGAA ACAGCATCCG 15650
TTACTCTGAG TTGGCACCCC TATTCGACAC CACCCGTGTG TACCTGGTGG 15700
ACAACAAGTC AACGGATGTG GCATCCCTGA ACTACCAGAA CGACCACAGC 15750
AACTTTCTGA CCACGGTCAT TCAAAACAAT GACTACAGCC CGGGGGAGGC 15800
AAGCACACAG ACCATCAATC TTGACGACCG GTCGCACTGG GGCGGCGACC 15850
TGAAAACCAT CCTGCATACC AACATGCCAA ATGTGAACGA GTTCATGTTT 15900
ACCAATAAGT TTAAGGCGCG GGTGATGGTG TCGCGCTTGC CTACTAAGGA 15950
```

FIG. 4N

```
CAATCAGGTG GAGCTGAAAT ACGAGTGGGT GGAGTTCACG CTGCCCGAGG 16000
GCAACTACTC CGAGACCATG ACCATAGACC TTATGAACAA CGCGATCGTG 16050
GAGCACTACT TGAAAGTGGG CAGACAGAAC GGGGTTCTGG AAAGCGACAT 16100
CGGGGTAAAG TTTGACACCC GCAACTTCAG ACTGGGGTTT GACCCCGTCA 16150
CTGGTCTTGT CATGCCTGGG GTATATACAA ACGAAGCCTT CCATCCAGAC 16200
ATCATTTTGC TGCCAGGATG CGGGGTGGAC TTCACCCACA GCCGCCTGAG 16250
CAACTTGTTG GGCATCCGCA AGCGGCAACC CTTCCAGGAG GGCTTTAGGA 16300
TCACCTACGA TGATCTGGAG GGTGGTAACA TTCCCGCACT GTTGGATGTG 16350
GACGCCTACC AGGCGAGCTT GAAAGATGAC ACCGAACAGG GCGGGGGTGG 16400
CGCAGGCGGC AGCAACAGCA GTGGCAGCGG CGCGGAAGAG AACTCCAACG 16450
CGGCAGCCGC GGCAATGCAG CCGGTGGAGG ACATGAACGA TCATGCCATT 16500
CGCGGCGACA CCTTTGCCAC ACGGGCTGAG GAGAAGCGCG CTGAGGCCGA 16550
AGCAGCGGCC GAAGCTGCCG CCCCCGCTGC GCAACCCGAG GTCGAGAAGC 16600
CTCAGAAGAA ACCGGTGATC AAACCCCTGA CAGAGGACAG CAAGAAACGC 16650
AGTTACAACC TAATAAGCAA TGACAGCACC TTCACCCAGT ACCGCAGCTG 16700
GTACCTTGCA TACAACTACG GCGACCCTCA GACCGGAATC CGCTCATGGA 16750
CCCTGCTTTG CACTCCTGAC GTAACCTGCG GCTCGGAGCA GGTCTACTGG 16800
TCGTTGCCAG ACATGATGCA AGACCCCGTG ACCTTCCGCT CCACGCGCCA 16850
GATCAGCAAC TTTCCGGTGG TGGGCGCCGA GCTGTTGCCC GTGCACTCCA 16900
AGAGCTTCTA CAACGACCAG GCCGTCTACT CCCAACTCAT CCGCCAGTTT 16950
ACCTCTCTGA CCCACGTGTT CAATCGCTTT CCCGAGAACC AGATTTTGGC 17000
GCGCCCGCCA GCCCCCACCA TCACCACCGT CAGTGAAAAC GTTCCTGCTC 17050
TCACAGATCA CGGGACGCTA CCGCTGCGCA ACAGCATCGG AGGAGTCCAG 17100
CGAGTGACCA TTACTGACGC CAGACGCCGC ACCTGCCCCT ACGTTTACAA 17150
GGCCCTGGGC ATAGTCTCGC CGCGCGTCCT ATCGAGCCGC ACTTTTTGAG 17200
```

FIG. 40

CAAGCATGTC CATCCTTATA TCGCCCAGCA ATAACACAGG CTGGGGCCTG 17250

CGCTTCCCAA GCAAGATGTT TGGCGGGGCC AAGAAGCGCT CCGACCAACA 17300

CCCAGTGCGC GTGCGCGGGC ACTACCGCGC GCCCTGGGGC GCGCACAAAC 17350

GCGGCCGCAC TGGGCGCACC ACCGTCGATG ACGCCATCGA CGCGGTGGTG 17400

GAGGAGGCGC GCAACTACAC GCCCACGCCG CCACCAGTGT CCACAGTGGA 17450

CGCGGCCATT CAGACCGTGG TGCGCGGAGC CCGGCGCTAT GCTAAAATGA 17500

AGAGACGGCG GAGGCGCGTA GCACGTCGCC ACCGCCGCCG ACCCGGCACT 17550

GCCGCCCAAC GCGCGGCGGC GGCCCTGCTT AACCGCGCAC GTCGCACCGG 17600

CCGACGGGCG GCCATGCGGG CCGCTCGAAG GCTGGCCGCG GGTATTGTCA 17650

CTGTGCCCCC CAGGTCCAGG CGACGAGCGG CCGCCGCAGC AGCCGCGGCC 17700

ATTAGTGCTA TGACTCAGGG TCGCAGGGGC AACGTGTATT GGGTGCGCGA 17750

CTCGGTTAGC GGCCTGCGCG TGCCCGTGCG CACCCGCCCC CCGCGCAACT 17800

AGATTGCAAG AAAAAACTAC TTAGACTCGT ACTGTTGTAT GTATCCAGCG 17850

GCGGCGGCGC GCAACGAAGC TATGTCCAAG CGCAAAATCA AAGAAGAGAT 17900

GCTCCAGGTC ATCGCGCCGG AGATCTATGG CCCCCCGAAG AAGGAAGAGC 17950

AGGATTACAA GCCCCGAAAG CTAAAGCGGG TCAAAAAGAA AAAGAAAGAT 18000

GATGATGATG AACTTGACGA CGAGGTGGAA CTGCTGCACG CTACCGCGCC 18050

SalI (18074)

CAGGCGACGG GTACAGTGGA AAGGTCGACG CGTAAAACGT GTTTTGCGAC 18100

CCGGCACCAC CGTAGTCTTT ACGCCCGGTG AGCGCTCCAC CCGCACCTAC 18150

AAGCGCGTGT ATGATGAGGT GTACGGCGAC GAGGACCTGC TTGAGCAGGC 18200

CAACGAGCGC CTCGGGGAGT TTGCCTACGG AAAGCGGCAT AAGGACATGC 18250

TGGCGTTGCC GCTGGACGAG GGCAACCCAA CACCTAGCCT AAAGCCCGTA 18300

ACACTGCAGC AGGTGCTGCC CGCGCTTGCA CCGTCCGAAG AAAAGCGCGG 18350

CCTAAAGCGC GAGTCTGGTG ACTTGGCACC CACCGTGCAG CTGATGGTAC 18400

FIG. 4P

```
CCAAGCGCCA GCGACTGGAA GATGTCTTGG AAAAAATGAC CGTGGAACCT 18450
GGGCTGGAGC CCGAGGTCCG CGTGCGGCCA ATCAAGCAGG TGGCGCCGGG 18500
ACTGGGCGTG CAGACCGTGG ACGTTCAGAT ACCCACTACC AGTAGCACCA 18550
GTATTGCCAC CGCCACAGAG GGCATGGAGA CACAAACGTC CCCGGTTGCC 18600
TCAGCGGTGG CGGATGCCGC GGTGCAGGCG GTCGCTGCGG CCGCGTCCAA 18650
GACCTCTACG GAGGTGCAAA CGGACCCGTG GATGTTTCGC GTTTCAGCCC 18700
CCCGGCGCCC GCGCGGTTCG AGGAAGTACG GCGCCGCCAG CGCGCTACTG 18750
CCCGAATATG CCCTACATCC TTCCATTGCG CCTACCCCCG GCTATCGTGG 18800
CTACACCTAC CGCCCCAGAA GACGAGCAAC TACCCGACGC CGAACCACCA 18850
CTGGAACCCG CCGCCGCCGT CGCCGTCGCC AGCCCGTGCT GGCCCCGATT 18900
TCCGTGCGCA GGGTGGCTCG CGAAGGAGGC AGGACCCTGG TGCTGCCAAC 18950
AGCGCGCTAC CACCCCAGCA TCGTTTAAAA GCCGGTCTTT GTGGTTCTTG 19000
CAGATATGGC CCTCACCTGC CGCCTCCGTT TCCCGGTGCC GGGATTCCGA 19050
GGAAGAATGC ACCGTAGGAG GGGCATGGCC GGCCACGGCC TGACGGGCGG 19100
CATGCGTCGT GCGCACCACC GGCGGCGGCG CGCGTCGCAC CGTCGCATGC 19150
GCGGCGGTAT CCTGCCCCTC CTTATTCCAC TGATCGCCGC GGCGATTGGC 19200
GCCGTGCCCG GAATTGCATC CGTGGCCTTG CAGGCGCAGA GACACTGATT 19250
AAAAACAAGT TGCATGTGGA AAAATCAAAA TAAAAAGTCT GGACTCTCAC 19300
GCTCGCTTGG TCCTGTAACT ATTTTGTAGA ATGGAAGACA TCAACTTTGC 19350
GTCTCTGGCC CCGCGACACG GCTCGCGCCC GTTCATGGGA AACTGGCAAG 19400
ATATCGGCAC CAGCAATATG AGCGGTGGCG CCTTCAGCTG GGGCTCGCTG 19450
TGGAGCGGCA TTAAAAATTT CGGTTCCACC GTTAAGAACT ATGGCAGCAA 19500
GGCCTGGAAC AGCAGCACAG GCCAGATGCT GAGGGATAAG TTGAAAGAGC 19550
AAAATTTCCA ACAAAAGGTG GTAGATGGCC TGGCCTCTGG CATTAGCGGG 19600
GTGGTGGACC TGGCCAACCA GGCAGTGCAA AATAAGATTA ACAGTAAGCT 19650
```

FIG. 4Q

```
TGATCCCCGC CCTCCCGTAG AGGAGCCTCC ACCGGCCGTG GAGACAGTGT 19700
CTCCAGAGGG GCGTGGCGAA AAGCGTCCGC GCCCCGACAG GGAAGAAACT 19750
CTGGTGACGC AAATAGACGA GCCTCCCTCG TACGAGGAGG CACTAAAGCA 19800
AGGCCTGCCC ACCACCCGTC CCATCGCGCC CATGGCTACC GGAGTGCTGG 19850
GCCAGCACAC ACCCGTAACG CTGGACCTGC CTCCCCCCGC CGACACCCAG 19900
CAGAAACCTG TGCTGCCAGG CCCGACCGCC GTTGTTGTAA CCCGTCCTAG 19950
CCGCGCGTCC CTGCGCCGCG CCGCCAGCGG TCCGCGATCG TTGCGGCCCG 20000
TAGCCAGTGG CAACTGGCAA AGCACACTGA ACAGCATCGT GGGTCTGGGG 20050
GTGCAATCCC TGAAGCGCCG ACGATGCTTC TGAATAGCTA ACGTGTCGTA 20100
TGTGTGTCAT GTATGCGTCC ATGTCGCCGC CAGAGGAGCT GCTGAGCCGC 20150
CGCGCGCCCG CTTTCCAAGA TGGCTACCCC TTCGATGATG CCGCAGTGGT 20200
CTTACATGCA CATCTCGGGC CAGGACGCCT CGGAGTACCT GAGCCCCGGG 20250
CTGGTGCAGT TTGCCCGCGC CACCGAGACG TACTTCAGCC TGAATAACAA 20300
GTTTAGAAAC CCCACGGTGG CGCCTACGCA CGACGTGACC ACAGACCGGT 20350
CCCAGCGTTT GACGCTGCGG TTCATCCCTG TGGACCGTGA GGATACTGCG 20400
TACTCGTACA AGGCGCGGTT CACCCTAGCT GTGGGTGATA ACCGTGTGCT 20450
GGACATGGCT TCCACGTACT TTGACATCCG CGGCGTGCTG GACAGGGGCC 20500
CTACTTTTAA GCCCTACTCT GGCACTGCCT ACAACGCCCT GGCTCCCAAG 20550
GGTGCCCCAA ATCCTTGCGA ATGGGATGAA GCTGCTACTG CTCTTGAAAT 20600
AAACCTAGAA GAAGAGGACG ATGACAACGA AGACGAAGTA GACGAGCAAG 20650
CTGAGCAGCA AAAAACTCAC GTATTTGGGC AGGCGCCTTA TTCTGGTATA 20700
AATATTACAA AGGAGGGTAT TCAAATAGGT GTCGAAGGTC AAACACCTAA 20750
ATATGCCGAT AAAACATTTC AACCTGAACC TCAAATAGGA GAATCTCAGT 20800
GGTACGAAAC TGAAATTAAT CATGCAGCTG GGAGAGTCCT TAAAAAGACT 20850
ACCCCAATGA AACCATGTTA CGGTTCATAT GCAAAACCCA CAAATGAAAA 20900
```

FIG. 4R

```
TGGAGGGCAA GGCATTCTTG TAAAGCAACA AAATGGAAAG CTAGAAAGTC 20950
AAGTGGAAAT GCAATTTTTC TCAACTACTG AGGCGACCGC AGGCAATGGT 21000
GATAACTTGA CTCCTAAAGT GGTATTGTAC AGTGAAGATG TAGATATAGA 21050
AACCCCAGAC ACTCATATTT CTTACATGCC CACTATTAAG GAAGGTAACT 21100
CACGAGAACT AATGGGCCAA CAATCTATGC CCAACAGGCC TAATTACATT 21150
GCTTTTAGGG ACAATTTTAT TGGTCTAATG TATTACAACA GCACGGGTAA 21200
TATGGGTGTT CTGGCGGGCC AAGCATCGCA GTTGAATGCT GTTGTAGATT 21250
TGCAAGACAG AAACACAGAG CTTTCATACC AGCTTTTGCT TGATTCCATT 21300
GGTGATAGAA CCAGGTACTT TTCTATGTGG AATCAGGCTG TTGACAGCTA 21350
TGATCCAGAT GTTAGAATTA TTGAAAATCA TGGAACTGAA GATGAACTTC 21400
CAAATTACTG CTTTCCACTG GGAGGTGTGA TTAATACAGA GACTCTTACC 21450
AAGGTAAAAC CTAAAACAGG TCAGGAAAAT GGATGGGAAA AAGATGCTAC 21500
AGAATTTTCA GATAAAAATG AAATAAGAGT TGGAAATAAT TTTGCCATGG 21550
AAATCAATCT AAATGCCAAC CTGTGGAGAA ATTTCCTGTA CTCCAACATA 21600
GCGCTGTATT TGCCCGACAA GCTAAAGTAC AGTCCTTCCA ACGTAAAAAT 21650
TTCTGATAAC CCAAACACCT ACGACTACAT GAACAAGCGA GTGGTGGCTC 21700
CCGGGTTAGT GGACTGCTAC ATTAACCTTG GAGCACGCTG GTCCCTTGAC 21750
TATATGGACA ACGTCAACCC ATTTAACCAC CACCGCAATG CTGGCCTGCG 21800
CTACCGCTCA ATGTTGCTGG GCAATGGTCG CTATGTGCCC TTCCACATCC 21850
AGGTGCCTCA GAAGTTCTTT GCCATTAAAA ACCTCCTTCT CCTGCCGGGC 21900
TCATACACCT ACGAGTGGAA CTTCAGGAAG GATGTTAACA TGGTTCTGCA 21950
GAGCTCCCTA GGAAATGACC TAAGGGTTGA CGGAGCCAGC ATTAAGTTTG 22000
ATAGCATTTG CCTTTACGCC ACCTTCTTCC CCATGGCCCA CAACACCGCC 22050
TCCACGCTTG AGGCCATGCT TAGAAACGAC ACCAACGACC AGTCCTTTAA 22100
CGACTATCTC TCCGCCGCCA ACATGCTCTA CCCTATACCC GCCAACGCTA 22150
```

FIG. 4S

```
CCAACGTGCC CATATCCATC CCCTCCCGCA ACTGGGCGGC TTTCCGCGGC 22200
TGGGCCTTCA CGCGCCTTAA GACTAAGGAA ACCCCATCAC TGGGCTCGGG 22250
CTACGACCCT TATTACACCT ACTCTGGCTC TATACCCTAC CTAGATGGAA 22300
CCTTTTACCT CAACCACACC TTTAAGAAGG TGGCCATTAC CTTTGACTCT 22350
TCTGTCAGCT GGCCTGGCAA TGACCGCCTG CTTACCCCCA ACGAGTTTGA 22400
AATTAAGCGC TCAGTTGACG GGGAGGGTTA CAACGTTGCC CAGTGTAACA 22450
TGACCAAAGA CTGGTTCCTG GTACAAATGC TAGCTAACTA CAACATTGGC 22500
TACCAGGGCT TCTATATCCC AGAGAGCTAC AAGGACCGCA TGTACTCCTT 22550
CTTTAGAAAC TTCCAGCCCA TGAGCCGTCA GGTGGTGGAT GATACTAAAT 22600
ACAAGGACTA CCAACAGGTG GGCATCCTAC ACCAACACAA CAACTCTGGA 22650
TTTGTTGGCT ACCTTGCCCC CACCATGCGC GAAGGACAGG CCTACCCTGC 22700
TAACTTCCCC TATCCGCTTA TAGGCAAGAC CGCAGTTGAC AGCATTACCC 22750
AGAAAAAGTT TCTTTGCGAT CGCACCCTTT GGCGCATCCC ATTCTCCAGT 22800
AACTTTATGT CCATGGGCGC ACTCACAGAC CTGGGCCAAA ACCTTCTCTA 22850
                                                 BamHI (22890)
CGCCAACTCC GCCCACGCGC TAGACATGAC TTTTGAGGTG GATCCCATGG 22900
ACGAGCCCAC CCTTCTTTAT GTTTTGTTTG AAGTCTTTGA CGTGGTCCGT 22950
GTGCACCGGC CGCACCGCGG CGTCATCGAA ACCGTGTACC TGCGCACGCC 23000
CTTCTCGGCC GGCAACGCCA CAACATAAAG AAGCAAGCAA CATCAACAAC 23050
AGCTGCCGCC ATGGGCTCCA GTGAGCAGGA ACTGAAAGCC ATTGTCAAAG 23100
ATCTTGGTTG TGGGCCATAT TTTTTGGGCA CCTATGACAA GCGCTTTCCA 23150
GGCTTTGTTT CTCCACACAA GCTCGCCTGC GCCATAGTCA ATACGGCCGG 23200
TCGCGAGACT GGGGGCGTAC ACTGGATGGC CTTTGCCTGG AACCCGCACT 23250
CAAAAACATG CTACCTCTTT GAGCCCTTTG GCTTTTCTGA CCAGCGACTC 23300
AAGCAGGTTT ACCAGTTTGA GTACGAGTCA CTCCTGCGCC GTAGCGCCAT 23350
```

FIG. 4T

```
TGCTTCTTCC CCCGACCGCT GTATAACGCT GGAAAAGTCC ACCCAAAGCG 23400
TACAGGGGCC CAACTCGGCC GCCTGTGGAC TATTCTGCTG CATGTTTCTC 23450
CACGCCTTTG CCAACTGGCC CCAAACTCCC ATGGATCACA ACCCCACCAT 23500
GAACCTTATT ACCGGGGTAC CCAACTCCAT GCTCAACAGT CCCCAGGTAC 23550
AGCCCACCCT GCGTCGCAAC CAGGAACAGC TCTACAGCTT CCTGGAGCGC 23600
CACTCGCCCT ACTTCCGCAG CCACAGTGCG CAGATTAGGA GCGCCACTTC 23650
TTTTTGTCAC TTGAAAAACA TGTAAAAATA ATGTACTAGA GACACTTTCA 23700
ATAAAGGCAA ATGCTTTTAT TTGTACACTC TCGGGTGATT ATTTACCCCC 23750
ACCCTTGCCG TCTGCGCCGT TTAAAAATCA AAGGGGTTCT GCCGCGCATC 23800
GCTATGCGCC ACTGGCAGGG ACACGTTGCG ATACTGGTGT TTAGTGCTCC 23850
ACTTAAACTC AGGCACAACC ATCCGCGGCA GCTCGGTGAA GTTTTCACTC 23900
CACAGGCTGC GCACCATCAC CAACGCGTTT AGCAGGTCGG GCGCCGATAT 23950
CTTGAAGTCG CAGTTGGGGC CTCCGCCCTG CGCGCGCGAG TTGCGATACA 24000
CAGGGTTGCA GCACTGGAAC ACTATCAGCG CCGGGTGGTG CACGCTGGCC 24050
AGCACGCTCT TGTCGGAGAT CAGATCCGCG TCCAGGTCCT CCGCGTTGCT 24100
CAGGGCGAAC GGAGTCAACT TTGGTAGCTG CCTTCCCAAA AAGGGCGCGT 24150
GCCCAGGCTT TGAGTTGCAC TCGCACCGTA GTGGCATCAA AAGGTGACCG 24200
TGCCCGGTCT GGGCGTTAGG ATACAGCGCC TGCATAAAAG CCTTGATCTG 24250
CTTAAAAGCC ACCTGAGCCT TTGCGCCTTC AGAGAAGAAC ATGCCGCAAG 24300
ACTTGCCGGA AAACTGATTG GCCGGACAGG CCGCGTCGTG CACGCAGCAC 24350
CTTGCGTCGG TGTTGGAGAT CTGCACCACA TTTCGGCCCC ACCGGTTCTT 24400
CACGATCTTG GCCTTGCTAG ACTGCTCCTT CAGCGCGCGC TGCCCGTTTT 24450
CGCTCGTCAC ATCCATTTCA ATCACGTGCT CCTTATTTAT CATAATGCTT 24500
CCGTGTAGAC ACTTAAGCTC GCCTTCGATC TCAGCGCAGC GGTGCAGCCA 24550
CAACGCGCAG CCCGTGGGCT CGTGATGCTT GTAGGTCACC TCTGCAAACG 24600
```

FIG. 4U

```
ACTGCAGGTA CGCCTGCAGG AATCGCCCCA TCATCGTCAC AAAGGTCTTG 24650
TTGCTGGTGA AGGTCAGCTG CAACCCGCGG TGCTCCTCGT TCAGCCAGGT 24700
CTTGCATACG GCCGCCAGAG CTTCCACTTG GTCAGGCAGT AGTTTGAAGT 24750
TCGCCTTTAG ATCGTTATCC ACGTGGTACT TGTCCATCAG CGCGCGCGCA 24800
GCCTCCATGC CCTTCTCCCA CGCAGACACG ATCGGCACAC TCAGCGGGTT 24850
CATCACCGTA ATTTCACTTT CCGCTTCGCT GGGCTCTTCC TCTTCCTCTT 24900
GCGTCCGCAT ACCACGCGCC ACTGGGTCGT CTTCATTCAG CCGCCGCACT 24950
GTGCGCTTAC CTCCTTTGCC ATGCTTGATT AGCACCGGTG GGTTGCTGAA 25000
ACCCACCATT TGTAGCGCCA CATCTTCTCT TTCTTCCTCG CTGTCCACGA 25050
TTACCTCTGG TGATGGCGGG CGCTCGGGCT TGGGAGAAGG GCGCTTCTTT 25100
TTCTTCTTGG GCGCAATGGC CAAATCCGCC GCCGAGGTCG ATGGCCGCGG 25150
GCTGGGTGTG CGCGGCACCA GCGCGTCTTG TGATGAGTCT TCCTCGTCCT 25200
CGGACTCGAT ACGCCGCCTC ATCCGCTTTT TTGGGGGCGC CCGGGGAGGC 25250
GGCGGCGACG GGGACGGGGA CGACACGTCC TCCATGGTTG GGGGACGTCG 25300
CGCCGCACCG CGTCCGCGCT CGGGGGTGGT TTCGCGCTGC TCCTCTTCCC 25350
GACTGGCCAT TTCCTTCTCC TATAGGCAGA AAAAGATCAT GGAGTCAGTC 25400
GAGAAGAAGG ACAGCCTAAC CGCCCCCTCT GAGTTCGCCA CCACCGCCTC 25450
CACCGATGCC GCCAACGCGC CTACCACCTT CCCCGTCGAG GCACCCCCGC 25500
TTGAGGAGGA GGAAGTGATT ATCGAGCAGG ACCCAGGTTT TGTAAGCGAA 25550
GACGACGAGG ACCGCTCAGT ACCAACAGAG GATAAAAAGC AAGACCAGGA 25600
CAACGCAGAG GCAAACGAGG AACAAGTCGG GCGGGGGGAC GAAAGGCATG 25650
GCGACTACCT AGATGTGGGA GACGACGTGC TGTTGAAGCA TCTGCAGCGC 25700
CAGTGCGCCA TTATCTGCGA CGCGTTGCAA GAGCGCAGCG ATGTGCCCCT 25750
CGCCATAGCG GATGTCAGCC TTGCCTACGA ACGCCACCTA TTCTCACCGC 25800
GCGTACCCCC CAAACGCCAA GAAAACGGCA CATGCGAGCC CAACCCGCGC 25850
```

FIG. 4V

CTCAACTTCT ACCCCGTATT TGCCGTGCCA GAGGTGCTTG CCACCTATCA 25900

CATCTTTTTC CAAAACTGCA AGATACCCCT ATCCTGCCGT GCCAACCGCA 25950

GCCGAGCGGA CAAGCAGCTG GCCTTGCGGC AGGGCGCTGT CATACCTGAT 26000

ATCGCCTCGC TCAACGAAGT GCCAAAAATC TTTGAGGGTC TTGGACGCGA 26050

CGAGAAGCGC GCGGCAAACG CTCTGCAACA GGAAAACAGC GAAAATGAAA 26100

GTCACTCTGG AGTGTTGGTG GAACTCGAGG GTGACAACGC GCGCCTAGCC 26150

GTACTAAAAC GCAGCATCGA GGTCACCCAC TTTGCCTACC CGGCACTTAA 26200

CCTACCCCCC AAGGTCATGA GCACAGTCAT GAGTGAGCTG ATCGTGCGCC 26250

GTGCGCAGCC CCTGGAGAGG GATGCAAATT TGCAAGAACA AACAGAGGAG 26300

GGCCTACCCG CAGTTGGCGA CGAGCAGCTA GCGCGCTGGC TTCAAACGCG 26350

CGAGCCTGCC GACTTGGAGG AGCGACGCAA ACTAATGATG GCCGCAGTGC 26400

TCGTTACCGT GGAGCTTGAG TGCATGCAGC GGTTCTTTGC TGACCCGGAG 26450

ATGCAGCGCA AGCTAGAGGA AACATTGCAC TACACCTTTC GACAGGGCTA 26500

CGTACGCCAG GCCTGCAAGA TCTCCAACGT GGAGCTCTGC AACCTGGTCT 26550

CCTACCTTGG AATTTTGCAC GAAAACCGCC TTGGGCAAAA CGTGCTTCAT 26600

TCCACGCTCA AGGGCGAGGC GCGCCGCGAC TACGTCCGCG ACTGCGTTTA 26650

CTTATTTCTA TGCTACACCT GGCAGACGGC CATGGGCGTT TGGCAGCAGT 26700

GCTTGGAGGA GTGCAACCTC AAGGAGCTGC AGAAACTGCT AAAGCAAAAC 26750

TTGAAGGACC TATGGACGGC CTTCAACGAG CGCTCCGTGG CCGCGCACCT 26800

GGCGGACATC ATTTTCCCCG AACGCCTGCT TAAAACCCTG CAACAGGGTC 26850

TGCCAGACTT CACCAGTCAA AGCATGTTGC AGAACTTTAG GAACTTTATC 26900

CTAGAGCGCT CAGGAATCTT GCCCGCCACC TGCTGTGCAC TTCCTAGCGA 26950

CTTTGTGCCC ATTAAGTACC GCGAATGCCC TCCGCCGCTT TGGGGCCACT 27000

GCTACCTTCT GCAGCTAGCC AACTACCTTG CCTACCACTC TGACATAATG 27050

GAAGACGTGA GCGGTGACGG TCTACTGGAG TGTCACTGTC GCTGCAACCT 27100

FIG. 4W

```
ATGCACCCCG CACCGCTCCC TGGTTTGCAA TTCGCAGCTG CTTAACGAAA 27150
GTCAAATTAT CGGTACCTTT GAGCTGCAGG GTCCCTCGCC TGACGAAAAG 27200
TCCGCGGCTC CGGGGTTGAA ACTCACTCCG GGGCTGTGGA CGTCGGCTTA 27250
CCTTCGCAAA TTTGTACCTG AGGACTACCA CGCCCACGAG ATTAGGTTCT 27300
ACGAAGACCA ATCCCGCCCG CCAAATGCGG AGCTTACCGC CTGCGTCATT 27350
ACCCAGGGCC ACATTCTTGG CCAATTGCAA GCCATCAACA AAGCCCGCCA 27400
AGAGTTTCTG CTACGAAAGG GACGGGGGGT TTACTTGGAC CCCCAGTCCG 27450
GCGAGGAGCT CAACCCAATC CCCCCGCCGC CGCAGCCCTA TCAGCAGCAG 27500
CCGCGGGCCC TTGCTTCCCA GGATGGCACC CAAAAAGAAG CTGCAGCTGC 27550
CGCCGCCACC CACGGACGAG GAGGAATACT GGGACAGTCA GGCAGAGGAG 27600
GTTTTGGACG AGGAGGAGGA GGACATGATG GAAGACTGGG AGAGCCTAGA 27650
CGAGGAAGCT TCCGAGGTCG AAGAGGTGTC AGACGAAACA CCGTCACCCT 27700
CGGTCGCATT CCCCTCGCCG GCGCCCCAGA AATCGGCAAC CGGTTCCAGC 27750
ATGGCTACAA CCTCCGCTCC TCAGGCGCCG CCGGCACTGC CCGTTCGCCG 27800
ACCCAACCGT AGATGGGACA CCACTGGAAC CAGGGCCGGT AAGTCCAAGC 27850
AGCCGCCGCC GTTAGCCCAA GAGCAACAAC AGCGCCAAGG CTACCGCTCA 27900
TGGCGCGGGC ACAAGAACGC CATAGTTGCT TGCTTGCAAG ACTGTGGGGG 27950
CAACATCTCC TTCGCCCGCC GCTTTCTTCT CTACCATCAC GGCGTGGCCT 28000
TCCCCCGTAA CATCCTGCAT TACTACCGTC ATCTCTACAG CCCATACTGC 28050
ACCGGCGGCA GCGGCAGCGG CAGCAACAGC AGCGGCCACA CAGAAGCAAA 28100
GGCGACCGGA TAGCAAGACT CTGACAAAGC CCAAGAAATC CACAGCGGCG 28150
GCAGCAGCAG GAGGAGGAGC GCTGCGTCTG GCGCCCAACG AACCCGTATC 28200
GACCCGCGAG CTTAGAAACA GGATTTTTCC CACTCTGTAT GCTATATTTC 28250
AACAGAGCAG GGGCCAAGAA CAAGAGCTGA AAATAAAAAA CAGGTCTCTG 28300
CGATCCCTCA CCCGCAGCTG CCTGTATCAC AAAAGCGAAG ATCAGCTTCG 28350
```

FIG. 4X

```
GCGCACGCTG GAAGACGCGG AGGCTCTCTT CAGTAAATAC TGCGCGCTGA 28400
CTCTTAAGGA CTAGTTTCGC GCCCTTTCTC AAATTTAAGC GCGAAAACTA 28450
CGTCATCTCC AGCGGCCACA CCCGGCGCCA GCACCTGTCG TCAGCGCCAT 28500
TATGAGCAAG GAAATTCCCA CGCCCTACAT GTGGAGTTAC CAGCCACAAA 28550
TGGGACTTGC GGCTGGAGCT GCCCAAGACT ACTCAACCCG AATAAACTAC 28600
ATGAGCGCGG GACCCCACAT GATATCCCGG GTCAACGGAA TCCGCGCCCA 28650
CCGAAACCGA ATTCTCTTGG AACAGGCGGC TATTACCACC ACACCTCGTA 28700
ATAACCTTAA TCCCCGTAGT TGGCCCGCTG CCCTGGTGTA CCAGGAAAGT 28750
CCCGCTCCCA CCACTGTGGT ACTTCCCAGA GACGCCCAGG CCGAAGTTCA 28800
GATGACTAAC TCAGGGGCGC AGCTTGCGGG CGGCTTTCGT CACAGGGTGC 28850
GGTCGCCCGG GCAGGGTATA ACTCACCTGA CAATCAGAGG GCGAGGTATT 28900
CAGCTCAACG ACGAGTCGGT GAGCTCCTCG CTTGGTCTCC GTCCGGACGG 28950
GACATTTCAG ATCGGCGGCG CCGGCCGTCC TTCATTCACG CCTCGTCAGG 29000
CAATCCTAAC TCTGCAGACC TCGTCCTCTG AGCCGCGCTC TGGAGGCATT 29050
GGAACTCTGC AATTTATTGA GGAGTTTGTG CCATCGGTCT ACTTTAACCC 29100
CTTCTCGGGA CCTCCCGGCC ACTATCCGGA TCAATTTATT CCTAACTTTG 29150
ACGCGGTAAA GGACTCGGCG GACGGCTACG ACTGAATGTT AAGTGGAGAG 29200
GCAGAGCAAC TGCGCCTGAA ACACCTGGTC CACTGTCGCC GCCACAAGTG 29250
CTTTGCCCGC GACTCCGGTG AGTTTTGCTA CTTTGAATTG CCCGAGGATC 29300
ATATCGAGGG CCCGGCGCAC GGCGTCCGGC TTACCGCCCA GGGAGAGCTT 29350
GCCCGTAGCC TGATTCGGGA GTTTACCCAG CGCCCCCTGC TAGTTGAGCG 29400
GGACAGGGGA CCCTGTGTTC TCACTGTGAT TTGCAACTGT CCTAACCTTG 29450
GATTACATCA AGATCTTTGT TGCCATCTCT GTGCTGAGTA TAATAAATAC 29500
AGAAATTAAA ATATACTGGG GCTCCTATCG CCATCCTGTA AACGCCACCG 29550
TCTTCACCCG CCCAAGCAAA CCAAGGCGAA CCTTACCTGG TACTTTTAAC 29600
```

FIG. 4Y

ATCTCTCCCT CTGTGATTTA CAACAGTTTC AACCCAGACG GAGTGAGTCT 29650

ACGAGAGAAC CTCTCCGAGC TCAGCTACTC CATCAGAAAA AACACCACCC 29700

TCCTTACCTG CCGGGAACGT ACGAGTGCGT CACCGGCCGC TGCACCACAC 29750

CTACCGCCTG ACCGTAAACC AGACTTTTTC CGGACAGACC TCAATAACTC 29800

TGTTTACCAG AACAGGAGGT GAGCTTAGAA AACCCTTAGG GTATTAGGCC 29850

AAAGGCGCAG CTACTGTGGG GTTTATGAAC AATTCAAGCA ACTCTACGGG 29900

CTATTCTAAT TCAGGTTTCT CTAGAATCGG GGTTGGGGTT ATTCTCTGTC 29950

TTGTGATTCT CTTTATTCTT ATACTAACGC TTCTCTGCCT AAGGCTCGCC 30000

GCCTGCTGTG TGCACATTTG CATTTATTGT CAGCTTTTTA AACGCTGGGG 30050

TCGCCACCCA AGATGATTAG GTACATAATC CTAGGTTTAC TCACCCTTGC 30100

GTCAGCCCAC GGTACCACCC AAAAGGTGGA TTTTAAGGAG CCAGCCTGTA 30150

ATGTTACATT CGCAGCTGAA GCTAATGAGT GCACCACTCT TATAAAATGC 30200

ACCACAGAAC ATGAAAAGCT GCTTATTCGC CACAAAAACA AAATTGGCAA 30250

GTATGCTGTT TATGCTATTT GGCAGCCAGG TGACACTACA GAGTATAATG 30300

TTACAGTTTT CCAGGGTAAA AGTCATAAAA CTTTTATGTA TACTTTTCCA 30350

TTTTATGAAA TGTGCGACAT TACCATGTAC ATGAGCAAAC AGTATAAGTT 30400

GTGGCCCCCA CAAAATTGTG TGGAAAACAC TGGCACTTTC TGCTGCACTG 30450

CTATGCTAAT TACAGTGCTC GCTTTGGTCT GTACCCTACT CTATATTAAA 30500

TACAAAAGCA GACGCAGCTT TATTGAGGAA AAGAAAATGC CTTAATTTAC 30550

TAAGTTACAA AGCTAATGTC ACCACTAACT GCTTTACTCG CTGCTTGCAA 30600

AACAAATTCA AAAAGTTAGC ATTATAATTA GAATAGGATT TAAACCCCCC 30650

GGTCATTTCC TGCTCAATAC CATTCCCCTG AACAATTGAC TCTATGTGGG 30700

ATATGCTCCA GCGCTACAAC CTTGAAGTCA GGCTTCCTGG ATGTCAGCAT 30750

CTGACTTTGG CCAGCACCTG TCCCGCGGAT TTGTTCCAGT CCAACTACAG 30800

CGACCCACCC TAACAGAGAT GACCAACACA ACCAACGCGG CCGCCGCTAC 30850

FIG. 4Z

CGGACTTACA TCTACCACAA ATACACCCCA AGTTTCTGCC TTTGTCAATA 30900

ACTGGGATAA CTTGGGCATG TGGTGGTTCT CCATAGCGCT TATGTTTGTA 30950

TGCCTTATTA TTATGTGGCT CATCTGCTGC CTAAAGCGCA AACGCGCCCG 31000

ACCACCCATC TATAGTCCCA TCATTGTGCT ACACCCAAAC AATGATGGAA 31050

TCCATAGATT GGACGGACTG AAACACATGT TCTTTTCTCT TACAGTATGA 30100

TTAAATGAGA CATGATTCCT CGAGTTTTTA TATTACTGAC CCTTGTTGCG 31150

CTTTTTTGTG CGTGCTCCAC ATTGGCTGCG GTTTCTCACA TCGAAGTAGA 31200

CTGCATTCCA GCCTTCACAG TCTATTTGCT TTACGGATTT GTCACCCTCA 31250

CGCTCATCTG CAGCCTCATC ACTGTGGTCA TCGCCTTTAT CCAGTGCATT 31300

GACTGGGTCT GTGTGCGCTT TGCATATCTC AGACACCATC CCCAGTACAG 31350

EcoRI (31377)

GGACAGGACT ATAGCTGAGC TTCTTAGAAT TCTTTAATTA TGAAATTTAC 31400

TGTGACTTTT CTGCTGATTA TTTGCACCCT ATCTGCGTTT TGTTCCCCGA 31450

CCTCCAAGCC TCAAAGACAT ATATCATGCA GATTCACTCG TATATGGAAT 31500

ATTCCAAGTT GCTACAATGA AAAAAGCGAT CTTTCCGAAG CCTGGTTATA 31550

TGCAATCATC TCTGTTATGG TGTTCTGCAG TACCATCTTA GCCCTAGCTA 31600

TATATCCCTA CCTTGACATT GGCTGGAAAC GAATAGATGC CATGAACCAC 31650

CCAACTTTCC CCGCGCCCGC TATGCTTCCA CTGCAACAAG TTGTTGCCGG 31700

CGGCTTTGTC CCAGCCAATC AGCCTCGCCC CACTTCTCCC ACCCCCACTG 31750

AAATCAGCTA CTTTAATCTA ACAGGAGGAG ATGACTGACA CCCTAGATCT 31800

AGAAATGGAC GGAATTATTA CAGAGCAGCG CCTGCTAGAA AGACGCAGGG 31850

CAGCGGCCGA GCAACAGCGC ATGAATCAAG AGCTCCAAGA CATGGTTAAC 31900

TTGCACCAGT GCAAAAGGGG TATCTTTTGT CTGGTAAAGC AGGCCAAAGT 31950

CACCTACGAC AGTAATACCA CCGGACACCG CCTTAGCTAC AAGTTGCCAA 32000

CCAAGCGTCA GAAATTGGTG GTCATGGTGG GAGAAAAGCC CATTACCATA 32050

FIG. 4AA

ACTCAGCACT CGGTAGAAAC CGAAGGCTGC ATTCACTCAC CTTGTCAAGG 32100

ACCTGAGGAT CTCTGCACCC TTATTAAGAC CCTGTGCGGT CTCAAAGATC 32150

TTATTCCCTT TAACTAATAA AAAAAAATAA TAAAGCATCA CTTACTTAAA 32200

ATCAGTTAGC AAATTTCTGT CCAGTTTATT CAGCAGCACC TCCTTGCCCT 32250

CCTCCCAGCT CTGGTATTGC AGCTTCCTCC TGGCTGCAAA CTTTCTCCAC 32300

AATCTAAATG GAATGTCAGT TTCCTCCTGT TCCTGTCCAT CCGCACCCAC 32350

TATCTTCATG TTGTTGCAGA TGAAGCGCGC AAGACCGTCT GAAGATACCT 32400

TCAACCCCGT GTATCCATAT GACACGGAAA CCGGTCCTCC AACTGTGCCT 32450

TTTCTTACTC CTCCCTTTGT ATCCCCCAAT GGGTTTCAAG AGAGTCCCCC 32500

TGGGGTACTC TCTTTGCGCC TATCCGAACC TCTAGTTACC TCCAATGGCA 32550

TGCTTGCGCT CAAAATGGGC AACGGCCTCT CTCTGGACGA GGCCGGCAAC 32600

CTTACCTCCC AAAATGTAAC CACTGTGAGC CCACCTCTCA AAAAAACCAA 32650

GTCAAACATA AACCTGGAAA TATCTGCACC CCTCACAGTT ACCTCAGAAG 32700

CCCTAACTGT GGCTGCCGCC GCACCTCTAA TGGTCGCGGG CAACACACTC 32750

ACCATGCAAT CACAGGCCCC GCTAACCGTG CACGACTCCA AACTTAGCAT 32800

TGCCACCCAA GGACCCCTCA CAGTGTCAGA AGGAAAGCTA GCCCTGCAAA 32850

CATCAGGCCC CCTCACCACC ACCGATAGCA GTACCCTTAC TATCACTGCC 32900

TCACCCCCTC TAACTACTGC CACTGGTAGC TTGGGCATTG ACTTGAAAGA 32950

GCCCATTTAT ACACAAAATG GAAAACTAGG ACTAAAGTAC GGGGCTCCTT 33000

TGCATGTAAC AGACGACCTA AACACTTTGA CCGTAGCAAC TGGTCCAGGT 33050

GTGACTATTA ATAATACTTC CTTGCAAACT AAAGTTACTG GAGCCTTGGG 33100

TTTTGATTCA CAAGGCAATA TGCAACTTAA TGTAGCAGGA GGACTAAGGA 33150

TTGATTCTCA AAACAGACGC CTTATACTTG ATGTTAGTTA TCCGTTTGAT 33200

GCTCAAAACC AACTAAATCT AAGACTAGGA CAGGGCCCTC TTTTTATAAA 33250

CTCAGCCCAC AACTTGGATA TTAACTACAA CAAAGGCCTT TACTTGTTTA 33300

FIG. 4BB

```
CAGCTTCAAA CAATTCCAAA AAGCTTGAGG TTAACCTAAG CACTGCCAAG 33350
GGGTTGATGT TTGACGCTAC AGCCATAGCC ATTAATGCAG GAGATGGGCT 33400
TGAATTTGGT TCACCTAATG CACCAAACAC AAATCCCCTC AAAACAAAAA 33450
TTGGCCATGG CCTAGAATTT GATTCAAACA AGGCTATGGT TCCTAAACTA 33500
GGAACTGGCC TTAGTTTTGA CAGCACAGGT GCCATTACAG TAGGAAACAA 33550
AAATAATGAT AAGCTAACTT TGTGGACCAC ACCAGCTCCA TCTCCTAACT 33600
GTAGACTAAA TGCAGAGAAA GATGCTAAAC TCACTTTGGT CTTAACAAAA 33650
TGTGGCAGTC AAATACTTGC TACAGTTTCA GTTTTGGCTG TTAAAGGCAG 33700
TTTGGCTCCA ATATCTGGAA CAGTTCAAAG TGCTCATCTT ATTATAAGAT 33750
TTGACGAAAA TGGAGTGCTA CTAAACAATT CCTTCCTGGA CCCAGAATAT 33800
TGGAACTTTA GAAATGGAGA TCTTACTGAA GGCACAGCCT ATACAAACGC 33850
TGTTGGATTT ATGCCTAACC TATCAGCTTA TCCAAAATCT CACGGTAAAA 33900
CTGCCAAAAG TAACATTGTC AGTCAAGTTT ACTTAAACGG AGACAAAACT 33950
AAACCTGTAA CACTAACCAT TACACTAAAC GGTACACAGG AAACAGGAGA 34000
CACAACTCCA AGTGCATACT CTATGTCATT TTCATGGGAC TGGTCTGGCC 34050
ACAACTACAT TAATGAAATA TTTGCCACAT CCTCTTACAC TTTTTCATAC 34100
ATTGCCCAAG AATAAAGAAT CGTTTGTGTT ATGTTTCAAC GTGTTTATTT 34150
TTCAATTGCA GAAAATTTCA AGTCATTTTT CATTCAGTAG TATAGCCCCA 34200
CCACCACATA GCTTATACAG ATCACCGTAC CTTAATCAAA CTCACAGAAC 34250
CCTAGTATTC AACCTGCCAC CTCCCTCCCA ACACACAGAG TACACAGTCC 34300
TTTCTCCCCG GCTGGCCTTA AAAAGCATCA TATCATGGGT AACAGACATA 34350
TTCTTAGGTG TTATATTCCA CACGGTTTCC TGTCGAGCCA AACGCTCATC 34400
AGTGATATTA ATAAACTGGC GGCGATATAA AATGCAAGGT GCTGCTCAAA 34450
AAATCAGGCA AAGCCTCGCG CAAAAAAGAA AGCACATCGT AGTCATGCTC 34500
ATGCAGATAA AGGCAGGTAA GCTCCGGAAC CACCACAGAA AAAGACACCA 34550
```

FIG. 4CC

TTTTTCTCTC AAACATGTCT GCGGGTTTCT GCATAAACAC AAAATAAAAT 34600

AACAAAAAAA CATTTAAACA TTAGAAGCCT GTCTTACAAC AGGAAAAACA 34650

ACCCTTATAA GCATAAGACG GACTACGGCC ATGCCGGCGT GACCGTAAAA 34700

AAACTGGTCA CCGTGATTAA AAAGCACCAC CGACAGCTCC TCGGTCATGT 34750

CCGGAGTCAT AATGTAAGAC TCGGTAAACA CATCAGGTTG ATTCATCGGT 34800

CAGTGCTAAA AAGCGACCGA AATAGCCCGG GGGAATACAT ACCCGCAGGC 34850

GTAGAGACAA CATTACAGCC CCCATAGGAG GTATAACAAA ATTAATAGGA 34900

GAGAAAAACA CATAAACACC TGAAAAACCC TCCTGCCTAG GCAAAATAGC 34950

ACCCTCCCGC TCCAGAACAA CATACAGCGC TTCACAGCGG CAGCCTAACA 35000

GTCAGCCTTA CCAGTAAAAA AGAAAACCTA TTAAAAAAAC ACCACTCGAC 35050

ACGGCACCAG CTCAATCAGT CACAGTGTAA AAAAGGGCCA AGTGCAGAGC 35100

GAGTATATAT AGGACTAAAA AATGACGTAA CGGTTAAAGT CCACAAAAAA 35150

CACCCAGAAA ACCGCACGCG AACCTACGCC CAGAAACGAA AGCCAAAAAA 35200

CCCACAACTT CCTCAAATCG TCACTTCCGT TTTCCCACGT TACGTAACTT 35250

CCCATTTTAA GAAAACTACA ATTCCCAACA CATACAAGTT ACTCCGCCCT 35300

AAAACCTACG TCACCCGCCC CGTTCCCACG CCCCGCGCCA CGTCACAAAC 35350

TCCACCCCCT CATTATCATA TTGGCTTCAA TCCAAAATAA GGTATATTAT 35400

TGATGATG 35408

```
                                SEQUENCE LISTING


(1) GENERAL INFORMATION:

   (iii) NUMBER OF SEQUENCES: 3


(2) INFORMATION FOR SEQ ID NO:1:

     (i) SEQUENCE CHARACTERISTICS:
          (A) LENGTH: 3653 base pairs
          (B) TYPE: nucleic acid
          (C) STRANDEDNESS: double
          (D) TOPOLOGY: Not Relevant

    (ii) MOLECULE TYPE: cDNA

    (ix) FEATURE:
          (A) NAME/KEY: CDS
          (B) LOCATION: 1521..2405

    (xi) SEQUENCE DESCRIPTION: SEQ ID NO:1:

CTGCATGTGT CAGAGGTTTT CACCGTCATC ACCGAAACGC GCGAGGCAGC AAGCTTGGCA      60

GAAATGGTTG AACTCCCGAG AGTGTCCTAC ACCTAGGGGA GAAGCAGCCA AGGGGTTGTT     120
```

-continued

```
TCCCACCAAG GACGACCCGT CTGCGCACAA ACGGATGAGC CCATCAGACA AAGACATATT    180
CATTCTCTGC TGCAAACTTG GCATAGCTCT GCTTTGCCTG GGGCTATTGG GGGAAGTTGC    240
GGTTCGTGCT CGCAGGGCTC TCACCCTTGA CTCTTTCAAT AATAACTCTT CTGTGCAAGA    300
TTACAATCTA AACAATTCGG AGAACTCGAC CTTCCTCCTG AGGCAAGGAC CACAGCCAAC    360
TTCCTCTTAC AAGCCGCATC GATTTTGTCC TTCAGAAATA GAAATAAGAA TGCTTGCTAA    420
AAATTATATT TTTACCAATA AGACCAATCC AATAGGTAGA TTATTAGTTA CTATGTTAAG    480
AAATGAATCA TTATCTTTTA GTACTATTTT TACTCAAATT CAGAAGTTAG AAATGGGAAT    540
AGAAAATAGA AAGAGACGCT CAACCTCAAT TGAAGAACAG GTGCAAGGAC TATTGACCAC    600
AGGCCTAGAA GTAAAAAAGG GAAAAAAGAG TGTTTTTGTC AAAATAGGAG ACAGGTGGTG    660
GCAACCAGGG ACTTATAGGG GACCTTACAT CTACAGACCA ACAGATGCCC CCTTACCATA    720
TACAGGAAGA TATGACTTAA ATTGGGATAG GTGGGTTACA GTCAATGGCT ATAAAGTGTT    780
ATATAGATCC CTCCCCTTTC GTGAAAGACT CGCCAGAGCT AGACCTCCTT GGTGTATGTT    840
GTCTCAAGAA AAGAAAGACG ACATGAAACA ACAGGTACAT GATTATATTT ATCTAGGAAC    900
AGGAATGCAC TTTTGGGGAA AGATTTTCCA TACCAAGGAG GGGACAGTGG CTGGACTAAT    960
AGAACATTAT TCTGCAAAAA CTTATGGCAT GAGTTATTAT GATTAGCCTT GATTTGCCCA   1020
ACCTTGCGGT TCCCAAGGCT TAAGTAAGTT TTTGGTTACA AACTGTTCTT AAAACAAGGA   1080
TGTGAGACAA GTGGTTTCCT GACTTGGTTT GGTATCAAAG GTTCTGATCT GAGCTCTGAG   1140
TGTTCTATTT TCCTATGTTC TTTTGGAATT TATCCAAATC TTATGTAAAT GCTTATGTAA   1200
ACCAAGATAT AAAAGAGTGC TGATTTTTTG AGTAAACTTG CAACAGTCCT AACATTCACC   1260
TCTTGTGTGT TTGTGTCTGT TCGCCATCCC GTCTCCGCTC GTCACTTATC CTTCACTTTC   1320
CAGAGGGTCC CCCCGCAGAC CCCGGCGACC CTCAGGTCGG CCGACTGCGG CAGCTGGCGC   1380
CCGAACAGGG ACCCTCGGAT AAGTGACCCT TGTCTTTATT TCTACTATTT TGTGTTCGTC   1440
TTGTTTTGTC TCTATCTTGT CTGGCTATCA TCACAAGAGC GGAACGGACT CACCTCAGGG   1500
AACCAAGCTA GCCCAATTCG ATGACTACGT CCGGCGTTCC ATTTGGCATG ACACTACGAC   1560
CAACACGATC TCGGTTGTCT CGGCGCACTC CGTACAGTAG GGATCGTCTA CCTCCTTTTG   1620
AGACAGAAAC CCGCGCTACC ATACTGGAGG ATCATCCGCT GCTGCCCGAA TGTAACACTT   1680
TGACAATGCA CAACGTGAGT TACGTGCGAG GTCTTCCCTG CAGTGTGGGA TTTACGCTGA   1740
TTCAGGAATG GGTTGTTCCC TGGGATATGG TTCTAACGCG GGAGGAGCTT GTAATCCTGA   1800
GGAAGTGTAT GCACGTGTGC CTGTGTTGTG CCAACATTGA TATCATGACG AGCATGATGA   1860
TCCATGGTTA CGAGTCCTGG GCTCTCCACT GTCATTGTTC CAGTCCCGGT TCCCTGCAGT   1920
GTATAGCCGG CGGGCAGGTT TTGGCCAGCT GGTTTAGGAT GGTGGTGGAT GGCGCCATGT   1980
TTAATCAGAG GTTTATATGG TACCGGGAGG TGGTGAATTA CAACATGCCA AAAGAGGTAA   2040
TGTTTATGTC CAGCGTGTTT ATGAGGGGTC GCCACTTAAT CTACCTGCGC TTGTGGTATG   2100
ATGGCCACGT GGGTTCTGTG GTCCCCGCCA TGAGCTTTGG ATACAGCGCC TTGCACTGTG   2160
GGATTTTGAA CAATATTGTG GTGCTGTGCT GCAGTTACTG TGCTGATTTA AGTGAGATCA   2220
GGGTGCGCTG CTGTGCCCGG AGGACAAGGC GCCTTATGCT GCGGGCGGTG CGAATCATCG   2280
CTGAGGAGAC CACTGCCATG TTGTATTCCT GCAGGACGGA GCGGCGGCGG CAGCAGTTTA   2340
TTCGCGCGCT GCTGCAGCAC CACCGCCCTA TCCTGATGCA CGATTATGAC TCTACCCCCA   2400
TGTAGGGATC CAAGCTTGCG GGCGCATCGA TGATATCAAG CTTGCATGCC TGCAGGTCGA   2460
CTCTAGAGGA TCCCGGGTGG NATCCCTGTG ACCCCTCCCC AGTGCCTCTC CTGGCCCTGG   2520
```

-continued

```
AAGTTGGCAC TCCAGTGCCC ACCAGCCTTG TCCTAATAAA ATTAAGTTGN ATCATTTTGT   2580
CTGACTAGGT GTCCTTCTAT AATATTATGG GGTGGAGGGG GGTGGTATGG AGCAANGGGN   2640
AANTTGGNAA GACAANCTGT AGGGCCTGCG GGGTCTATTG GGAACAAGCT GGAGTGCAGT   2700
GGCACAATCT TGGCTCACTG CAATCTCCGC CTCCTGGGTT CAAGCGATTC TCCTGCCTCA   2760
GACTCCCGAG TTGTTGGGAT TCCAGGCATG CATGACCAGG CTCAGATAAT TTTTGTTTTT   2820
TTGGTAGAGA CGGGGTTTCA CCATATTGGN CAGGCTGGTC TCCAACTCCT AATCTCAGGT   2880
GATCTNCCCA CCTTGGCCTC CCAAATTGCT GGGATTACAG GNGTGAACCA CTGNTCCCTT   2940
CCCTGTCCTT CTGATTTTAA AATAACTATA CCAGCAGGAG GACGTCCAGA CACAGCATAG   3000
GCTACCTGGC CATGCCCAAC CGGTGGGACA TTTGAGTTGC TTGCTTGGCA CTGTCCTCTC   3060
ATGCGTTGGG TCCACTCAGT AGATGCCTGT TGAATTGGGT ACGCGGCCAG CTTGGCTGTG   3120
GAATGTGTGT CAGTTAGGGT GTGGAAAGTC CCCAGGCTCC CCAGCAGGCA GAAGTATGCA   3180
AAGCATGCAT CTCAATTAGT CAGCAACCAG GTGTGGAAAG TCCCCAGGCT CCCCAGCAGG   3240
CAGAAGTATG CAAAGCATGC ATCTCAATTA GTCAGNAACC ATAGNCCCGC CCCTAACTCC   3300
GTCCATCCCG GCCCTAACTC NGGCCAGTTC CGACCNTNCT CCGGCNNATG GNTGAGTAAT   3360
TTGCNNGATT TATGCAGNGG GCGAGGNCGC CTCGGGCTCT GAGNTNTTCC AGAAGTAGTG   3420
AGGAGGCTTT NNTGGTGGAA TTGATCAGCT TGGGATCTGA TCAAGAGACA GGATGAGGAT   3480
CGNNNCGNAT GATTGAACAA GATGGGTTGC ACGGAGGTTC TCCGGNCGCT TGGGTGGGGA   3540
GGNTATTCGG NTATTNTTGG TGNACAACAG NNAAACGGNT GTTCTGATGC CGCCGCGTTC   3600
NCGCTTTCAG NGCAGGGGGG CCCCCCTTCT NTTGAGANNA GCNCCCCTTN TTG          3653
```

(2) INFORMATION FOR SEQ ID NO:2:

(i) SEQUENCE CHARACTERISTICS:
(A) LENGTH: 294 amino acids
(B) TYPE: amino acid
(C) STRANDEDNESS:
(D) TOPOLOGY: Not Relevant (ii) MOLECULE TYPE: protein (xi) SEQUENCE DESCRIPTION: SEQ ID NO:2:

```
Met Thr Thr Ser Gly Val Pro Phe Gly Met Thr Leu Arg Pro Thr Arg
1               5                   10                  15

Ser Arg Leu Ser Arg Arg Thr Pro Tyr Ser Arg Asp Arg Leu Pro Pro
            20                  25                  30

Phe Glu Thr Glu Thr Arg Ala Thr Ile Leu Glu Asp His Pro Leu Leu
        35                  40                  45

Pro Glu Cys Asn Thr Leu Thr Met His Asn Val Ser Tyr Val Arg Gly
    50                  55                  60

Leu Pro Cys Ser Val Gly Phe Thr Leu Ile Gln Glu Trp Val Val Pro
65                  70                  75                  80

Trp Asp Met Val Leu Thr Arg Glu Glu Leu Val Ile Leu Arg Lys Cys
                85                  90                  95

Met His Val Cys Leu Cys Cys Ala Asn Ile Asp Ile Met Thr Ser Met
            100                 105                 110

Met Ile Tyr Gly Tyr Glu Ser Trp Ala Leu His Cys His Cys Ser Ser
        115                 120                 125

Pro Gly Ser Leu Gln Cys Ile Ala Gly Gly Gln Val Leu Ala Ser Trp
    130                 135                 140
```

-continued

```
Phe Arg Met Val Val Asp Gly Ala Met Phe Asn Gln Arg Phe Ile Trp
145                 150                 155                 160

Tyr Arg Glu Val Val Asn Tyr Asn Met Pro Lys Glu Val Met Phe Met
                165                 170                 175

Ser Ser Val Phe Met Arg Gly Arg His Leu Ile Tyr Leu Arg Tyr Trp
            180                 185                 190

Tyr Asp Gly His Val Gly Ser Val Val Pro Ala Met Ser Phe Gly Tyr
        195                 200                 205

Ser Ala Leu His Cys Gly Ile Leu Asn Asn Ile Val Val Leu Cys Cys
    210                 215                 220

Ser Tyr Cys Ala Asp Leu Ser Glu Ile Arg Val Arg Cys Cys Ala Arg
225                 230                 235                 240

Arg Thr Arg Arg Leu Met Leu Arg Ala Val Arg Ile Ile Ala Glu Glu
                245                 250                 255

Thr Thr Ala Met Leu Tyr Ser Cys Arg Thr Glu Arg Arg Arg Gln Gln
            260                 265                 270

Phe Ile Arg Ala Leu Leu Gln His His Arg Pro Ile Leu Met His Asp
        275                 280                 285

Tyr Asp Ser Thr Pro Met
    290
```

(2) INFORMATION FOR SEQ ID NO:3:

(i) SEQUENCE CHARACTERISTICS:
(A) LENGTH: 35408 base pairs
(B) TYPE: nucleic acid
(C) STRANDEDNESS: Not Relevant
(D) TOPOLOGY: Not Relevant (ii) MOLECULE TYPE: other nucleic acid (xi) SEQUENCE DESCRIPTION: SEQ ID NO:3:

```
CATCATCAAT AATATACCTT ATTTTGGATT GAAGCCAATA TGATAATGAG GGGGTGGAGT     60

TTGTGACGTG GCGCGGGGCG TGGGAACGGG GCGGGTGACG TAGTAGTGTG GCGGAAGTGT    120

GATGTTGCAA GTGTGGCGGA ACACATGTAA GCGACGGATG TGGCAAAAGT GACGTTTTTG    180

GTGTGCGCCG GTGTACACAG GAAGTGACAA TTTTCGCGCG GTTTTAGGCG GATGTTGTAG    240

TAAATTTGGG CGTAACCGAG TAAGATTTGG CCATTTTCGC GGGAAAACTG AATAAGAGGA    300

AGTGAAATCT GAATAATTTT GTGTTACTCA TAGCGCGTAA TATTTGTCTA GGGAGATCAG    360

CCTGCAGGTC GTTACATAAC TTACGGTAAA TGGCCCGCCT GGCTGACCGC CCAACGACCC    420

CCGCCCATTG ACGTCAATAA TGACGTATGT TCCCATAGTA ACGCCAATAG GGACTTTCCA    480

TTGACGTCAA TGGGTGGAGT ATTTACGGTA AACTGCCCAC TTGGCAGTAC ATCAAGTGTA    540

TCATATGCCA AGTACGCCCC CTATTGACGT CAATGACGGT AAATGGCCCG CCTGGCATTA    600

TGCCCAGTAC ATGACCTTAT GGGACTTTCC TACTTGGCAG TACATCTACT CGAGGCCACG    660

TTCTGCTTCA CTCTCCCCAT CTCCCCCCCC TCCCCACCCC CAATTTTGTA TTTATTTATT    720

TTTTAATTAT TTTGTGCAGC GATGGGGGCG GGGGGGGGGG GGGGGCGCGC GCCAGGCGGG    780

GCGGGGCGGG GCGAGGGGCG GGGCGGGGCG AGGCGGAGAG GTGCGGCGGC AGCCAATCAG    840

AGCGGCGCGC TCCGAAAGTT TCCTTTTATG GCGAGGCGGC GGCGGCGGCG GCCCTATAAA    900

AAGCGAAGCG CGCGGCGGGC GGGAGCGGGA TCAGCCACCG CGGTGGCGGC CGCAATTCCC    960

GGGGATCGAA AGAGCCTGCT AAAGCAAAAA AGAAGTCACC ATGTCGTTTA CTTTGACCAA   1020

CAAGAACGTG ATTTTCGTTG CCGGTCTGGG AGGCATTGGT CTGGACACCA GCAAGGAGCT   1080
```

-continued

```
GCTCAAGCGC GATCCCGTCG TTTTACAACG TCGTGACTGG GAAAACCCTG GCGTTACCCA   1140
ACTTAATCGC CTTGCAGCAC ATCCCCCTTT CGCCAGCTGG CGTAATAGCG AAGAGGCCCG   1200
CACCGATCGC CCTTCCCAAC AGTTGCGCAG CCTGAATGGC GAATGGCGCT TTGCCTGGTT   1260
TCCGGCACCA GAAGCGGTGC CGGAAAGCTG GCTGGAGTGC GATCTTCCTG AGGCCGATAC   1320
TGTCGTCGTC CCCTCAAACT GGCAGATGCA CGGTTACGAT GCGCCCATCT ACACCAACGT   1380
AACCTATCCC ATTACGGTCA ATCCGCCGTT TGTTCCCACG GAGAATCCGA CGGGTTGTTA   1440
CTCGCTCACA TTTAATGTTG ATGAAAGCTG GCTACAGGAA GGCCAGACGC GAATTATTTT   1500
TGATGGCGTT AACTCGGCGT TTCATCTGTG GTGCAACGGG CGCTGGGTCG GTTACGGCCA   1560
GGACAGTCGT TTGCCGTCTG AATTTGACCT GAGCGCATTT TTACGCGCCG GAGAAAACCG   1620
CCTCGCGGTG ATGGTGCTGC GTTGGAGTGA CGGCAGTTAT CTGGAAGATC AGGATATGTG   1680
GCGGATGAGC GGCATTTTCC GTGACGTCTC GTTGCTGCAT AAACCGACTA CACAAATCAG   1740
CGATTTCCAT GTTGCCACTC GCTTTAATGA TGATTTCAGC CGCGCTGTAC TGGAGGCTGA   1800
AGTTCAGATG TGCGGCGAGT TGCGTGACTA CCTACGGGTA ACAGTTTCTT TATGGCAGGG   1860
TGAAACGCAG GTCGCCAGCG GCACCGCGCC TTTCGGCGGT GAAATTATCG ATGAGCGTGG   1920
TGGTTATGCC GATCGCGTCA CACTACGTCT GAACGTCGAA AACCCGAAAC TGTGGAGCGC   1980
CGAAATCCCG AATCTCTATC GTGCGGTGGT TGAACTGCAC ACCGCCGACG GCACGCTGAT   2040
TGAAGCAGAA GCCTGCGATG TCGGTTTCCG CGAGGTGCGG ATTGAAAATG GTCTGCTGCT   2100
GCTGAACGGC AAGCCGTTGC TGATTCGAGG CGTTAACCGT CACGAGCATC ATCCTCTGCA   2160
TGGTCAGGTC ATGGATGAGC AGACGATGGT GCAGGATATC CTGCTGATGA AGCAGAACAA   2220
CTTTAACGCC GTGCGCTGTT CGCATTATCC GAACCATCCG CTGTGGTACA CGCTGTGCGA   2280
CCGCTACGGC CTGTATGTGG TGGATGAAGC CAATATTGAA ACCCACGGCA TGGTGCCAAT   2340
GAATCGTCTG ACCGATGATC CGCGCTGGCT ACCGGCGATG AGCGAACGCG TAACGCGAAT   2400
GGTGCAGCGC GATCGTAATC ACCCGAGTGT GATCATCTGG TCGCTGGGGA ATGAATCAGG   2460
CCACGGCGCT AATCACGACG CGCTGTATCG CTGGATCAAA TCTGTCGATC CTTCCCGCCC   2520
GGTGCAGTAT GAAGGCGGCG GAGCCGACAC CACGGCCACC GATATTATTT GCCCGATGTA   2580
CGCGCGCGTG GATGAAGACC AGCCCTTCCC GGCTGTGCCG AAATGGTCCA TCAAAAAATG   2640
GCTTTCGCTA CCTGGAGAGA CGCGCCCGCT GATCCTTTGC GAATACGCCC ACGCGATGGG   2700
TAACAGTCTT GGCGGTTTCG CTAAATACTG GCAGGCGTTT CGTCAGTATC CCCGTTTACA   2760
GGGCGGCTTC GTCTGGGACT GGGTGGATCA GTCGCTGATT AAATATGATG AAAACGGCAA   2820
CCCGTGGTCG GCTTACGGCG GTGATTTTGG CGATACGCCG AACGATCGCC AGTTCTGTAT   2880
GAACGGTCTG GTCTTTGCCG ACCGCACGCC GCATCCAGCG CTGACGGAAG CAAAACACCA   2940
GCAGCAGTTT TTCCAGTTCC GTTTATCCGG GCAAACCATC GAAGTGACCA GCGAATACCT   3000
GTTCCGTCAT AGCGATAACG AGCTCCTGCA CTGGATGGTG GCGCTGGATG GTAAGCCGCT   3060
GGCAAGCGGT GAAGTGCCTC TGGATGTCGC TCCACAAGGT AAACAGTTGA TTGAACTGCC   3120
TGAACTACCG CAGCCGGAGA GCGCCGGGCA ACTCTGGCTC ACAGTACGCG TAGTGCAACC   3180
GAACGCGACC GCATGGTCAG AAGCCGGGCA CATCAGCGCC TGGCAGCAGT GGCGTCTGGC   3240
GGAAAACCTC AGTGTGACGC TCCCCGCCGC GTCCCACGCC ATCCCGCATC TGACCACCAG   3300
CGAAATGGAT TTTTGCATCG AGCTGGGTAA TAAGCGTTGG CAATTTAACC GCCAGTCAGG   3360
CTTTCTTTCA CAGATGTGGA TTGGCGATAA AAAACAACTG CTGACGCCGC TGCGCGATCA   3420
GTTCACCCGT GCACCGCTGG ATAACGACAT TGGCGTAAGT GAAGCGACCC GCATTGACCC   3480
```

-continued

```
TAACGCCTGG GTCGAACGCT GGAAGGCGGC GGGCCATTAC CAGGCCGAAG CAGCGTTGTT   3540
GCAGTGCACG GCAGATACAC TTGCTGATGC GGTGCTGATT ACGACCGCTC ACGCGTGGCA   3600
GCATCAGGGG AAAACCTTAT TTATCAGCCG GAAAACCTAC CGGATTGATG GTAGTGGTCA   3660
AATGGCGATT ACCGTTGATG TTGAAGTGGC GAGCGATACA CCGCATCCGG CGCGGATTGG   3720
CCTGAACTGC CAGCTGGCGC AGGTAGCAGA GCGGGTAAAC TGGCTCGGAT TAGGGCCGCA   3780
AGAAAACTAT CCCGACCGCC TTACTGCCGC CTGTTTTGAC CGCTGGGATC TGCCATTGTC   3840
AGACATGTAT ACCCCGTACG TCTTCCCGAG CGAAAACGGT CTGCGCTGCG GGACGCGCGA   3900
ATTGAATTAT GGCCCACACC AGTGGCGCGG CGACTTCCAG TTCAACATCA GCCGCTACAG   3960
TCAACAGCAA CTGATGGAAA CCAGCCATCG CCATCTGCTG CACGCGGAAG AAGGCACATG   4020
GCTGAATATC GACGGTTTCC ATATGGGGAT TGGTGGCGAC GACTCCTGGA GCCCGTCAGT   4080
ATCGGCGGAA TTACAGCTGA GCGCCGGTCG CTACCATTAC CAGTTGGTCT GGTGTCAAAA   4140
ATAATAATAA CCGGGCAGGC CATGTCTGCC CGTATTTCGC GTAAGGAAAT CCATTATGTA   4200
CTATTTAAAA AACACAAACT TTTGGATGTT CGGTTTATTC TTTTTCTTTT ACTTTTTTAT   4260
CATGGGAGCC TACTTCCCGT TTTTCCCGAT TTGGCTACAT GACATCAACC ATATCAGCAA   4320
AAGTGATACG GGTATTATTT TTGCCGCTAT TTCTCTGTTC TCGCTATTAT TCCAACCGCT   4380
GTTTGGTCTG CTTTCTGACA AACTCGGCCT CGACTCTAGG CGGCCGCGGG GATCCAGACA   4440
TGATAAGATA CATTGATGAG TTTGGACAAA CCACAACTAG AATGCAGTGA AAAAAATGCT   4500
TTATTTGTGA AATTTGTGAT GCTATTGCTT TATTTGTAAC CATTATAAGC TGCAATAAAC   4560
AAGTTAACAA CAACAATTGC ATTCATTTTA TGTTTCAGGT TCAGGGGGAG GTGTGGGAGG   4620
TTTTTTCGGA TCCTCTAGAG TCGACCTGCA GGCTGATCAG TGGAAGGTGC TGAGGTACGA   4680
TGAGACCCGC ACCAGGTGCA GACCCTGCGA GTGTGGCGGT AAACATATTA GGAACCAGCC   4740
TGTGATGCTG GATGTGACCG AGGAGCTGAG GCCCGATCAC TTGGTGCTGG CCTGCACCCG   4800
CGCTGAGTTT GGCTCTAGCG ATGAAGATAC AGATTGAGGT ACTGAAATGT GTGGGCGTGG   4860
CTTAAGGGTG GGAAAGAATA TATAAGGTGG GGGTCTTATG TAGTTTTGTA TCTGTTTTGC   4920
AGCAGCCGCC GCCGCCATGA GCACCAACTC GTTTGATGGA AGCATTGTGA GCTCATATTT   4980
GACAACGCGC ATGCCCCCAT GGGCCGGGGT GCGTCAGAAT GTGATGGGCT CCAGCATTGA   5040
TGGTCGCCCC GTCCTGCCCG CAAACTCTAC TACCTTGACC TACGAGACCG TGTCTGGAAC   5100
GCCGTTGGAG ACTGCAGCCT CCGCCGCCGC TTCAGCCGCT GCAGCCACCG CCCGCGGGAT   5160
TGTGACTGAC TTTGCTTTCC TGAGCCCGCT TGCAAGCAGT GCAGCTTCCC GTTCATCCGC   5220
CCGCGATGAC AAGTTGACGG CTCTTTTGGC ACAATTGGAT TCTTTGACCC GGGAACTTAA   5280
TGTCGTTTCT CAGCAGCTGT TGGATCTGCG CCAGCAGGTT TCTGCCCTGA AGGCTTCCTC   5340
CCCTCCCAAT GCGGTTTAAA ACATAAATAA AAAACCAGAC TCTGTTTGGA TTTGGATCAA   5400
GCAAGTGTCT TGCTGTCTTT ATTTAGGGGT TTTGCGCGCG CGGTAGGCCC GGGACCAGCG   5460
GTCTCGGTCG TTGAGGGTCC TGTGTATTTT TTCCAGGACG TGGTAAAGGT GACTCTGGAT   5520
GTTCAGATAC ATGGGCATAA GCCCGTCTCT GGGGTGGAGG TAGCACCACT GCAGAGCTTC   5580
ATGCTGCGGG GTGGTGTTGT AGATGATCCA GTCGTAGCAG GAGCGCTGGG CGTGGTGCCT   5640
AAAAATGTCT TTCAGTAGCA AGCTGATTGC CAGGGGCAGG CCCTTGGTGT AAGTGTTTAC   5700
AAAGCGGTTA AGCTGGGATG GGTGCATACG TGGGGATATG AGATGCATCT TGGACTGTAT   5760
TTTTAGGTTG GCTATGTTCC CAGCCATATC CCTCCGGGGA TTCATGTTGT GCAGAACCAC   5820
```

-continued

```
CAGCACAGTG TATCCGGTGC ACTTGGGAAA TTTGTCATGT AGCTTAGAAG GAAATGCGTG   5880
GAAGAACTTG GAGACGCCCT TGTGACCTCC AAGATTTTCC ATGCATTCGT CCATAATGAT   5940
GGCAATGGGC CCACGGGCGG CGGCCTGGGC GAAGATATTT CTGGGATCAC TAACGTCATA   6000
GTTGTGTTCC AGGATGAGAT CGTCATAGGC CATTTTTACA AAGCGCGGGC GGAGGGTGCC   6060
AGACTGCGGT ATAATGGTTC CATCCGGCCC AGGGGCGTAG TTACCCTCAC AGATTTGCAT   6120
TTCCCACGCT TTGAGTTCAG ATGGGGGGAT CATGTCTACC TGCGGGGCGA TGAAGAAAAC   6180
GGTTTCCGGG GTAGGGGAGA TCAGCTGGGA AGAAAGCAGG TTCCTGAGCA GCTGCGACTT   6240
ACCGCAGCCG GTGGGCCCGT AAATCACACC TATTACCGGG TGCAACTGGT AGTTAAGAGA   6300
GCTGCAGCTG CCGTCATCCC TGAGCAGGGG GGCCACTTCG TTAAGCATGT CCCTGACTCG   6360
CATGTTTTCC CTGACCAAAT CCGCCAGAAG GCGCTCGCCG CCCAGCGATA GCAGTTCTTG   6420
CAAGGAAGCA AAGTTTTTCA ACGGTTTGAG ACCGTCCGCC GTAGGCATGC TTTTGAGCGT   6480
TTGACCAAGC AGTTCCAGGC GGTCCCACAG CTCGGTCACC TGCTCTACGG CATCTCGATC   6540
CAGCATATCT CCTCGTTTCG CGGGTTGGGG CGGCTTTCGC TGTACGGCAG TAGTCGGTGC   6600
TCGTCCAGAC GGGCCAGGGT CATGTCTTTC CACGGGCGCA GGGTCCTCGT CAGCGTAGTC   6660
TGGGTCACGG TGAAGGGGTG CGCTCCGGGC TGCGCGCTGG CCAGGGTGCG CTTGAGGCTG   6720
GTCCTGCTGG TGCTGAAGCG CTGCCGGTCT TCGCCCTGCG CGTCGGCCAG GTAGCATTTG   6780
ACCATGGTGT CATAGTCCAG CCCCTCCGCG GCGTGGCCCT TGGCGCGCAG CTTGCCCTTG   6840
GAGGAGGCGC CGCACGAGGG GCAGTGCAGA CTTTTGAGGG CGTAGAGCTT GGGCGCGAGA   6900
AATACCGATT CCGGGGAGTA GGCATCCGCG CCGCAGGCCC CGCAGACGGT CTCGCATTCC   6960
ACGAGCCAGG TGAGCTCTGG CCGTTCGGGG TCAAAAACCA GGTTTCCCCC ATGCTTTTTG   7020
ATGCGTTTCT TACCTCTGGT TTCCATGAGC CGGTGTCCAC GCTCGGTGAC GAAAAGGCTG   7080
TCCGTGTCCC CGTATACAGA CTTGAGAGGC CTGTCCTCGA GCGGTGTTCC GCGGTCCTCC   7140
TCGTATAGAA ACTCGGACCA CTCTGAGACA AAGGCTCGCG TCCAGGCCAG CACGAAGGAG   7200
GCTAAGTGGG AGGGGTAGCG GTCGTTGTCC ACTAGGGGGT CCACTCGCTC CAGGGTGTGA   7260
AGACACATGT CGCCCTCTTC GGCATCAAGG AAGGTGATTG GTTTGTAGGT GTAGGCCACG   7320
TGACCGGGTG TTCCTGAAGG GGGGCTATAA AAGGGGGTGG GGGCGCGTTC GTCCTCACTC   7380
TCTTCCGCAT CGCTGTCTGC GAGGGCCAGC TGTTGGGGTG AGTACTCCCT CTGAAAAGCG   7440
GGCATGACTT CTGCGCTAAG ATTGTCAGTT TCCAAAAACG AGGAGGATTT GATATTCACC   7500
TGGCCCGCGG TGATGCCTTT GAGGGTGGCC GCATCCATCT GGTCAGAAAA GACAATCTTT   7560
TTGTTGTCAA GCTTGGTGGC AAACGACCCG TAGAGGGCGT TGGACAGCAA CTTGGCGATG   7620
GAGCGCAGGG TTTGGTTTTT GTCGCGATCG GCGCGCTCCT TGGCCGCGAT GTTTAGCTGC   7680
ACGTATTCGC GCGCAACGCA CCGCCATTCG GGAAAGACGG TGGTGCGCTC GTCGGGCACC   7740
AGGTGCACGC GCCAACCGCG GTTGTGCAGG GTGACAAGGT CAACGCTGGT GGCTACCTCT   7800
CCGCGTAGGC GCTCGTTGGT CCAGCAGAGG CGGCCGCCCT TGCGCGAGCA GAATGGCGGT   7860
AGGGGGTCTA GCTGCGTCTC GTCCGGGGGG TCTGCGTCCA CGGTAAAGAC CCCGGGCAGC   7920
AGGCGCGCGT CGAAGTAGTC TATCTTGCAT CCTTGCAAGT CTAGCGCCTG CTGCCATGCG   7980
CGGGCGGCAA GCGCGCGCTC GTATGGGTTG AGTGGGGGAC CCCATGGCAT GGGGTGGGTG   8040
AGCGCGGAGG CGTACATGCC GCAAATGTCG TAAACGTAGA GGGGCTCTCT GAGTATTCCA   8100
AGATATGTAG GGTAGCATCT TCCACCGCGG ATGCTGGCGC GCACGTAATC GTATAGTTCG   8160
TGCGAGGGAG CGAGGAGGTC GGGACCGAGG TTGCTACGGG CGGGCTGCTC TGCTCGGAAG   8220
```

-continued

```
ACTATCTGCC TGAAGATGGC ATGTGAGTTG GATGATATGG TTGGACGCTG GAAGACGTTG   8280
AAGCTGGCGT CTGTGAGACC TACCGCGTCA CGCACGAAGG AGGCGTAGGA GTCGCGCAGC   8340
TTGTTGACCA GCTCGGCGGT GACCTGCACG TCTAGGGCGC AGTAGTCCAG GGTTTCCTTG   8400
ATGATGTCAT ACTTATCCTG TCCCTTTTTT TTCCACAGCT CGCGGTTGAG GACAAACTCT   8460
TCGCGGTCTT TCCAGTACTC TTGGATCGGA AACCCGTCGG CCTCCGAACG GTAAGAGCCT   8520
AGCATGTAGA ACTGGTTGAC GGCCTGGTAG GCGCAGCATC CCTTTTCTAC GGGTAGCGCG   8580
TATGCCTGCG CGGCCTTCCG GAGCGAGGTG TGGGTGAGCG CAAAGGTGTC CCTGACCATG   8640
ACTTTGAGGT ACTGGTATTT GAAGTCAGTG TCGTCGCATC CGCCCTGCTC CCAGAGCAAA   8700
AAGTCCGTGC GCTTTTTGGA ACGCGGATTT GGCAGGGCGA AGGTGACATC GTTGAAGAGT   8760
ATCTTTCCCG CGCGAGGCAT AAAGTTGCGT GTGATGCGGA AGGGTCCCGG CACCTCGGAA   8820
CGGTTGTTAA TTACCTGGGC GGCGAGCACG ATCTCGTCAA AGCCGTTGAT GTTGTGGCCC   8880
ACAATGTAAA GTTCCAAGAA GCGCGGGATG CCCTTGATGG AAGGCAATTT TTTAAGTTCC   8940
TCGTAGGTGA GCTCTTCAGG GGAGCTGAGC CCGTGCTCTG AAAGGGCCCA GTCTGCAAGA   9000
TGAGGGTTGG AAGCGACGAA TGAGCTCCAC AGGTCACGGG CCATTAGCAT TTGCAGGTGG   9060
TCGCGAAAGG TCCTAAACTG GCGACCTATG GCCATTTTTT CTGGGGTGAT GCAGTAGAAG   9120
GTAAGCGGGT CTTGTTCCCA GCGGTCCCAT CCAAGGTTCG CGGCTAGGTC TCGCGCGGCA   9180
GTCACTAGAG GCTCATCTCC GCCGAACTTC ATGACCAGCA TGAAGGGCAC GAGCTGCTTC   9240
CCAAAGGCCC CCATCCAAGT ATAGGTCTCT ACATCGTAGG TGACAAAGAG ACGCTCGGTG   9300
CGAGGATGCG AGCCGATCGG GAAGAACTGG ATCTCCCGCC ACCAATTGGA GGAGTGGCTA   9360
TTGATGTGGT GAAAGTAGAA GTCCCTGCGA CGGGCCGAAC ACTCGTGCTG GCTTTTGTAA   9420
AAACGTGCGC AGTACTGGCA GCGGTGCACG GGCTGTACAT CCTGCACGAG GTTGACCTGA   9480
CGACCGCGCA CAAGGAAGCA GAGTGGGAAT TTGAGCCCCT CGCCTGGCGG GTTTGGCTGG   9540
TGGTCTTCTA CTTCGGCTGC TTGTCCTTGA CCGTCTGGCT GCTCGAGGGG AGTTACGGTG   9600
GATCGGACCA CCACGCCGCG CGAGCCCAAA GTCCAGATGT CCGCGCGCGG CGGTCGGAGC   9660
TTGATGACAA CATCGCGCAG ATGGGAGCTG TCCATGGTCT GGAGCTCCCG CGGCGTCAGG   9720
TCAGGCGGGA GCTCCTGCAG GTTTACCTCG CATAGACGGG TCAGGGCGCG GGCTAGATCC   9780
AGGTGATACC TAATTTCCAG GGGCTGGTTG GTGGCGGCGT CGATGGCTTG CAAGAGGCCG   9840
CATCCCCGCG GCGCGACTAC GGTACCGCGC GGCGGGCGGT GGGCCGCGGG GGTGTCCTTG   9900
GATGATGCAT CTAAAAGCGG TGACGCGGGC GAGCCCCCGG AGGTAGGGGG GGCTCCGGAC   9960
CCGCCGGGAG AGGGGGCAGG GGCACGTCGG CGCCGCGCGC GGGCAGGAGC TGGTGCTGCG  10020
CGCGTAGGTT GCTGGCGAAC GCGACGACGC GGCGGTTGAT CTCCTGAATC TGGCGCCTCT  10080
GCGTGAAGAC GACGGGCCCG GTGAGCTTGA GCCTGAAAGA GAGTTCGACA GAATCAATTT  10140
CGGTGTCGTT GACGGCGGCC TGGCGCAAAA TCTCCTGCAC GTCTCCTGAG TTGTCTTGAT  10200
AGGCGATCTC GGCCATGAAC TGCTCGATCT CTTCCTCCTG GAGATCTCCG CGTCCGGCTC  10260
GCTCCACGGT GGCGGCGAGG TCGTTGGAAA TGCGGGCCAT GAGCTGCGAG AAGGCGTTGA  10320
GGCCTCCCTC GTTCCAGACG CGGCTGTAGA CCACGCCCCC TTCGGCATCG CGGGCGCGCA  10380
TGACCACCTG CGCGAGATTG AGCTCCACGT GCCGGGCGAA GACGGCGTAG TTTCGCAGGC  10440
GCTGAAAGAG GTAGTTGAGG GTGGTGGCGG TGTGTTCTGC CACGAAGAAG TACATAACCC  10500
AGCGTCGCAA CGTGGATTCG TTGATATCCC CCAAGGCCTC AAGGCGCTCC ATGGCCTCGT  10560
```

-continued

```
AGAAGTCCAC GGCGAAGTTG AAAAACTGGG AGTTGCGCGC CGACACGGTT AACTCCTCCT  10620
CCAGAAGACG GATGAGCTCG GCGACAGTGT CGCGCACCTC GCGCTCAAAG GCTACAGGGG  10680
CCTCTTCTTC TTCTTCAATC TCCTCTTCCA TAAGGGCCTC CCCTTCTTCT TCTTCTGGCG  10740
GCGGTGGGGG AGGGGGGACA CGGCGGCGAC GACGGCGCAC CGGGAGGCGG TCGACAAAGC  10800
GCTCGATCAT CTCCCCGCGG CGACGGCGCA TGGTCTCGGT GACGGCGCGG CCGTTCTCGC  10860
GGGGGCGCAG TTGGAAGACG CCGCCCGTCA TGTCCCGGTT ATGGGTTGGC GGGGGGCTGC  10920
CATGCGGCAG GGATACGGCG CTAACGATGC ATCTCAACAA TTGTTGTGTA GGTACTCCGC  10980
CGCCGAGGGA CCTGAGCGAG TCCGCATCGA CCGGATCGGA AAACCTCTCG AGAAAGGCGT  11040
CTAACCAGTC ACAGTCGCAA GGTAGGCTGA GCACCGTGGC GGGCGGCAGC GGGCGGCGGT  11100
CGGGGTTGTT TCTGGCGGAG GTGCTGCTGA TGATGTAATT AAAGTAGGCG GTCTTGAGAC  11160
GGCGGATGGT CGACAGAAGC ACCATGTCCT TGGGTCCGGC CTGCTGAATG CGCAGGCGGT  11220
CGGCCATGCC CCAGGCTTCG TTTTGACATC GGCGCAGGTC TTTGTAGTAG TCTTGCATGA  11280
GCCTTTCTAC CGGCACTTCT TCTTCTCCTT CCTCTTGTCC TGCATCTCTT GCATCTATCG  11340
CTGCGGCGGC GGCGGAGTTT GGCCGTAGGT GGCGCCCTCT TCCTCCCATG CGTGTGACCC  11400
CGAAGCCCCT CATCGGCTGA AGCAGGGCTA GGTCGGCGAC AACGCGCTCG GCTAATATGG  11460
CCTGCTGCAC CTGCGTGAGG GTAGACTGGA AGTCATCCAT GTCCACAAAG CGGTGGTATG  11520
CGCCCGTGTT GATGGTGTAA GTGCAGTTGG CCATAACGGA CCAGTTAACG GTCTGGTGAC  11580
CCGGCTGCGA GAGCTCGGTG TACCTGAGAC GCGAGTAAGC CCTCGAGTCA AATACGTAGT  11640
CGTTGCAAGT CCGCACCAGG TACTGGTATC CCACCAAAAA GTGCGGCGGC GGCTGGCGGT  11700
AGAGGGGCCA GCGTAGGGTG GCCGGGGCTC CGGGGGCGAG ATCTTCCAAC ATAAGGCGAT  11760
GATATCCGTA GATGTACCTG GACATCCAGG TGATGCCGGC GGCGGTGGTG GAGGCGCGCG  11820
GAAAGTCGCG GACGCGGTTC CAGATGTTGC GCAGCGGCAA AAAGTGCTCC ATGGTCGGGA  11880
CGCTCTGGCC GGTCAGGCGC GCGCAATCGT TGACGCTCTA GACCGTGCAA AAGGAGAGCC  11940
TGTAAGCGGG CACTCTTCCG TGGTCTGGTG GATAAATTCG CAAGGGTATC ATGGCGGACG  12000
ACCGGGGTTC GAGCCCCGTA TCCGGCCGTC CGCCGTGATC CATGCGGTTA CCGCCCGCGT  12060
GTCGAACCCA GGTGTGCGAC GTCAGACAAC GGGGGAGTGC TCCTTTTGGC TTCCTTCCAG  12120
GCGCGGCGGC TGCTGCGCTA GCTTTTTTGG CCACTGGCCG CGCGCAGCGT AAGCGGTTAG  12180
GCTGGAAAGC GAAAGCATTA AGTGGCTCGC TCCCTGTAGC CGGAGGGTTA TTTTCCAAGG  12240
GTTGAGTCGC GGGACCCCCG GTTCGAGTCT CGGACCGGCC GGACTGCGGC GAACGGGGGT  12300
TTGCCTCCCC GTCATGCAAG ACCCCGCTTG CAAATTCCTC CGGAAACAGG GACGAGCCCC  12360
TTTTTTGCTT TTCCCAGATG CATCCGGTGC TGCGGCAGAT GCGCCCCCCT CCTCAGCAGC  12420
GGCAAGAGCA AGAGCAGCGG CAGACATGCA GGGCACCCTC CCCTCCTCCT ACCGCGTCAG  12480
GAGGGGCGAC ATCCGCGGTT GACGCGGCAG CAGATGGTGA TTACGAACCC CCGCGGCGCC  12540
GGGCCCGGCA CTACCTGGAC TTGGAGGAGG GCGAGGGCCT GGCGCGGCTA GGAGCGCCCT  12600
CTCCTGAGCG GTACCCAAGG GTGCAGCTGA AGCGTGATAC GCGTGAGGCG TACGTGCCGC  12660
GGCAGAACCT GTTTCGCGAC CGCGAGGGAG AGGAGCCCGA GGAGATGCGG GATCGAAAGT  12720
TCCACGCAGG GCGCGAGCTG CGGCATGGCC TGAATCGCGA GCGGTTGCTG CGCGAGGAGG  12780
ACTTTGAGCC CGACGCGCGA ACCGGGATTA GTCCCGCGCG CGCACACGTG GCGGCCGCCG  12840
ACCTGGTAAC CGCATACGAG CAGACGGTGA ACCAGGAGAT TAACTTTCAA AAAAGCTTTA  12900
ACAACCACGT GCGTACGCTT GTGGCGCGCG AGGAGGTGGC TATAGGACTG ATGCATCTGT  12960
```

-continued

```
GGGACTTTGT AAGCGCGCTG GAGCAAAACC CAAATAGCAA GCCGCTCATG GCGCAGCTGT  13020
TCCTTATAGT GCAGCACAGC AGGGACAACG AGGCATTCAG GGATGCGCTG CTAAACATAG  13080
TAGAGCCCGA GGGCCGCTGG CTGCTCGATT TGATAAACAT CCTGCAGAGC ATAGTGGTGC  13140
AGGAGCGCAG CTTGAGCCTG GCTGACAAGG TGGCCGCCAT CAACTATTCC ATGCTTAGCC  13200
TGGGCAAGTT TTACGCCCGC AAGATATACC ATACCCCTTA CGTTCCCATA GACAAGGAGG  13260
TAAAGATCGA GGGGTTCTAC ATGCGCATGG CGCTGAAGGT GCTTACCTTG AGCGACGACC  13320
TGGGCGTTTA TCGCAACGAG CGCATCCACA AGGCCGTGAG CGTGAGCCGG CGGCGCGAGC  13380
TCAGCGACCG CGAGCTGATG CACAGCCTGC AAAGGGCCCT GGCTGGCACG GGCAGCGGCG  13440
ATAGAGAGGC CGAGTCCTAC TTTGACGCGG GCGCTGACCT GCGCTGGGCC CCAAGCCGAC  13500
GCGCCCTGGA GGCAGCTGGG GCCGGACCTG GGCTGGCGGT GGCACCCGCG CGCGCTGGCA  13560
ACGTCGGCGG CGTGGAGGAA TATGACGAGG ACGATGAGTA CGAGCCAGAG GACGGCGAGT  13620
ACTAAGCGGT GATGTTTCTG ATCAGATGAT GCAAGACGCA ACGGACCCGG CGGTGCGGGC  13680
GGCGCTGCAG AGCCAGCCGT CCGGCCTTAA CTCCACGGAC GACTGGCGCC AGGTCATGGA  13740
CCGCATCATG TCGCTGACTG CGCGCAATCC TGACGCGTTC CGGCAGCAGC CGCAGGCCAA  13800
CCGGCTCTCC GCAATTCTGG AAGCGGTGGT CCCGGCGCGC GCAAACCCCA CGCACGAGAA  13860
GGTGCTGGCG ATCGTAAACG CGCTGGCCGA AAACAGGGCC ATCCGGCCCG ACGAGGCCGG  13920
CCTGGTCTAC GACGCGCTGC TTCAGCGCGT GGCTCGTTAC AACAGCGGCA ACGTGCAGAC  13980
CAACCTGGAC CGGCTGGTGG GGGATGTGCG CGAGGCCGTG GCGCAGCGTG AGCGCGCGCA  14040
GCAGCAGGGC AACCTGGGCT CCATGGTTGC ACTAAACGCC TTCCTGAGTA CACAGCCCGC  14100
CAACGTGCCG CGGGGACAGG AGGACTACAC CAACTTTGTG AGCGCACTGC GGCTAATGGT  14160
GACTGAGACA CCGCAAAGTG AGGTGTACCA GTCTGGGCCA GACTATTTTT TCCAGACCAG  14220
TAGACAAGGC CTGCAGACCG TAAACCTGAG CCAGGCTTTC AAAAACTTGC AGGGGCTGTG  14280
GGGGGTGCGG GCTCCCACAG GCGACCGCGC GACCGTGTCT AGCTTGCTGA CGCCCAACTC  14340
GCGCCTGTTG CTGCTGCTAA TAGCGCCCTT CACGGACAGT GGCAGCGTGT CCCGGGACAC  14400
ATACCTAGGT CACTTGCTGA CACTGTACCG CGAGGCCATA GGTCAGGCGC ATGTGGACGA  14460
GCATACTTTC CAGGAGATTA CAAGTGTCAG CCGCGCGCTG GGGCAGGAGG ACACGGGCAG  14520
CCTGGAGGCA ACCCTAAACT ACCTGCTGAC CAACCGGCGG CAGAAGATCC CCTCGTTGCA  14580
CAGTTTAAAC AGCGAGGAGG AGCGCATTTT GCGCTACGTG CAGCAGAGCG TGAGCCTTAA  14640
CCTGATGCGC GACGGGGTAA CGCCCAGCGT GGCGCTGGAC ATGACCGCGC GCAACATGGA  14700
ACCGGGCATG TATGCCTCAA ACCGGCCGTT TATCAACCGC CTAATGGACT ACTTGCATCG  14760
CGCGGCCGCC GTGAACCCCG AGTATTTCAC CAATGCCATC TTGAACCCGC ACTGGCTACC  14820
GCCCCCTGGT TTCTACACCG GGGGATTCGA GGTGCCCGAG GGTAACGATG GATTCCTCTG  14880
GGACGACATA GACGACAGCG TGTTTTCCCC GCAACCGCAG ACCCTGCTAG AGTTGCAACA  14940
GCGCGAGCAG GCAGAGGCGG CGCTGCGAAA GGAAAGCTTC CGCAGGCCAA GCAGCTTGTC  15000
CGATCTAGGC GCTGCGGCCC CGCGGTCAGA TGCTAGTAGC CCATTTCCAA GCTTGATAGG  15060
GTCTCTTACC AGCACTCGCA CCACCCGCCC GCGCCTGCTG GGCGAGGAGG AGTACCTAAA  15120
CAACTCGCTG CTGCAGCCGC AGCGCGAAAA AAACCTGCCT CCGGCATTTC CCAACAACGG  15180
GATAGAGAGC CTAGTGGACA AGATGAGTAG ATGGAAGACG TACGCGCAGG AGCACAGGGA  15240
CGTGCCAGGC CCGCGCCCGC CCACCCGTCG TCAAAGGCAC GACCGTCAGC GGGGTCTGGT  15300
```

-continued

```
GTGGGAGGAC GATGACTCGG CAGACGACAG CAGCGTCCTG GATTTGGGAG GGAGTGGCAA  15360
CCCGTTTGCG CACCTTCGCC CCAGGCTGGG GAGAATGTTT TAAAAAAAAA AAAGCATGAT  15420
GCAAAATAAA AAACTCACCA AGGCCATGGC ACCGAGCGTT GGTTTTCTTG TATTCCCCTT  15480
AGTATGCGGC GCGCGGCGAT GTATGAGGAA GGTCCTCCTC CCTCCTACGA GAGTGTGGTG  15540
AGCGCGGCGC CAGTGGCGGC GGCGCTGGGT TCTCCCTTCG ATGCTCCCCT GGACCCGCCG  15600
TTTGTGCCTC CGCGGTACCT GCGGCCTACC GGGGGGAGAA ACAGCATCCG TTACTCTGAG  15660
TTGGCACCCC TATTCGACAC CACCCGTGTG TACCTGGTGG ACAACAAGTC AACGGATGTG  15720
GCATCCCTGA ACTACCAGAA CGACCACAGC AACTTTCTGA CCACGGTCAT TCAAAACAAT  15780
GACTACAGCC CGGGGGAGGC AAGCACACAG ACCATCAATC TTGACGACCG GTCGCACTGG  15840
GGCGGCGACC TGAAAACCAT CCTGCATACC AACATGCCAA ATGTGAACGA GTTCATGTTT  15900
ACCAATAAGT TTAAGGCGCG GGTGATGGTG TCGCGCTTGC CTACTAAGGA CAATCAGGTG  15960
GAGCTGAAAT ACGAGTGGGT GGAGTTCACG CTGCCCGAGG GCAACTACTC CGAGACCATG  16020
ACCATAGACC TTATGAACAA CGCGATCGTG GAGCACTACT TGAAAGTGGG CAGACAGAAC  16080
GGGGTTCTGG AAAGCGACAT CGGGGTAAAG TTTGACACCC GCAACTTCAG ACTGGGGTTT  16140
GACCCCGTCA CTGGTCTTGT CATGCCTGGG GTATATACAA ACGAAGCCTT CCATCCAGAC  16200
ATCATTTTGC TGCCAGGATG CGGGGTGGAC TTCACCCACA GCCGCCTGAG CAACTTGTTG  16260
GGCATCCGCA AGCGGCAACC CTTCCAGGAG GGCTTTAGGA TCACCTACGA TGATCTGGAG  16320
GGTGGTAACA TTCCCGCACT GTTGGATGTG GACGCCTACC AGGCGAGCTT GAAAGATGAC  16380
ACCGAACAGG GCGGGGGTGG CGCAGGCGGC AGCAACAGCA GTGGCAGCGG CGCGGAAGAG  16440
AACTCCAACG CGGCAGCCGC GGCAATGCAG CCGGTGGAGG ACATGAACGA TCATGCCATT  16500
CGCGGCGACA CCTTTGCCAC ACGGGCTGAG GAGAAGCGCG CTGAGGCCGA AGCAGCGGCC  16560
GAAGCTGCCG CCCCCGCTGC GCAACCCGAG GTCGAGAAGC CTCAGAAGAA ACCGGTGATC  16620
AAACCCCTGA CAGAGGACAG CAAGAAACGC AGTTACAACC TAATAAGCAA TGACAGCACC  16680
TTCACCCAGT ACCGCAGCTG GTACCTTGCA TACAACTACG GCGACCCTCA GACCGGAATC  16740
CGCTCATGGA CCCTGCTTTG CACTCCTGAC GTAACCTGCG GCTCGGAGCA GGTCTACTGG  16800
TCGTTGCCAG ACATGATGCA AGACCCCGTG ACCTTCCGCT CCACGCGCCA GATCAGCAAC  16860
TTTCCGGTGG TGGGCGCCGA GCTGTTGCCC GTGCACTCCA AGAGCTTCTA CAACGACCAG  16920
GCCGTCTACT CCCAACTCAT CCGCCAGTTT ACCTCTCTGA CCCACGTGTT CAATCGCTTT  16980
CCCGAGAACC AGATTTTGGC GCGCCCGCCA GCCCCCACCA TCACCACCGT CAGTGAAAAC  17040
GTTCCTGCTC TCACAGATCA CGGGACGCTA CCGCTGCGCA ACAGCATCGG AGGAGTCCAG  17100
CGAGTGACCA TTACTGACGC CAGACGCCGC ACCTGCCCCT ACGTTTACAA GGCCCTGGGC  17160
ATAGTCTCGC CGCGCGTCCT ATCGAGCCGC ACTTTTTGAG CAAGCATGTC CATCCTTATA  17220
TCGCCCAGCA ATAACACAGG CTGGGGCCTG CGCTTCCCAA GCAAGATGTT TGGCGGGGCC  17280
AAGAAGCGCT CCGACCAACA CCCAGTGCGC GTGCGCGGGC ACTACCGCGC GCCCTGGGGC  17340
GCGCACAAAC GCGGCCGCAC TGGGCGCACC ACCGTCGATG ACGCCATCGA CGCGGTGGTG  17400
GAGGAGGCGC GCAACTACAC GCCCACGCCG CCACCAGTGT CCACAGTGGA CGCGGCCATT  17460
CAGACCGTGG TGCGCGGAGC CCGGCGCTAT GCTAAAATGA AGAGACGGCG GAGGCGCGTA  17520
GCACGTCGCC ACCGCCGCCG ACCCGGCACT GCCGCCCAAC GCGCGGCGGC GGCCCTGCTT  17580
AACCGCGCAC GTCGCACCGG CCGACGGGCG GCCATGCGGG CCGCTCGAAG GCTGGCCGCG  17640
GGTATTGTCA CTGTGCCCCC CAGGTCCAGG CGACGAGCGG CCGCCGCAGC AGCCGCGGCC  17700
```

-continued

```
ATTAGTGCTA TGACTCAGGG TCGCAGGGGC AACGTGTATT GGGTGCGCGA CTCGGTTAGC  17760
GGCCTGCGCG TGCCCGTGCG CACCCGCCCC CCGCGCAACT AGATTGCAAG AAAAAACTAC  17820
TTAGACTCGT ACTGTTGTAT GTATCCAGCG GCGGCGGCGC GCAACGAAGC TATGTCCAAG  17880
CGCAAAATCA AAGAAGAGAT GCTCCAGGTC ATCGCGCCGG AGATCTATGG CCCCCCGAAG  17940
AAGGAAGAGC AGGATTACAA GCCCCGAAAG CTAAAGCGGG TCAAAAAGAA AAAGAAAGAT  18000
GATGATGATG AACTTGACGA CGAGGTGGAA CTGCTGCACG CTACCGCGCC CAGGCGACGG  18060
GTACAGTGGA AAGGTCGACG CGTAAAACGT GTTTTGCGAC CCGGCACCAC CGTAGTCTTT  18120
ACGCCCGGTG AGCGCTCCAC CCGCACCTAC AAGCGCGTGT ATGATGAGGT GTACGGCGAC  18180
GAGGACCTGC TTGAGCAGGC CAACGAGCGC CTCGGGGAGT TTGCCTACGG AAAGCGGCAT  18240
AAGGACATGC TGGCGTTGCC GCTGGACGAG GGCAACCCAA CACCTAGCCT AAAGCCCGTA  18300
ACACTGCAGC AGGTGCTGCC CGCGCTTGCA CCGTCCGAAG AAAAGCGCGG CCTAAAGCGC  18360
GAGTCTGGTG ACTTGGCACC CACCGTGCAG CTGATGGTAC CCAAGCGCCA GCGACTGGAA  18420
GATGTCTTGG AAAAAATGAC CGTGGAACCT GGGCTGGAGC CCGAGGTCCG CGTGCGGCCA  18480
ATCAAGCAGG TGGCGCCGGG ACTGGGCGTG CAGACCGTGG ACGTTCAGAT ACCCACTACC  18540
AGTAGCACCA GTATTGCCAC CGCCACAGAG GGCATGGAGA CACAAACGTC CCCGGTTGCC  18600
TCAGCGGTGG CGGATGCCGC GGTGCAGGCG GTCGCTGCGG CCGCGTCCAA GACCTCTACG  18660
GAGGTGCAAA CGGACCCGTG GATGTTTCGC GTTTCAGCCC CCCGGCGCCC GCGCGGTTCG  18720
AGGAAGTACG GCGCCGCCAG CGCGCTACTG CCCGAATATG CCCTACATCC TTCCATTGCG  18780
CCTACCCCCG GCTATCGTGG CTACACCTAC CGCCCCAGAA GACGAGCAAC TACCCGACGC  18840
CGAACCACCA CTGGAACCCG CCGCCGCCGT CGCCGTCGCC AGCCCGTGCT GGCCCCGATT  18900
TCCGTGCGCA GGGTGGCTCG CGAAGGAGGC AGGACCCTGG TGCTGCCAAC AGCGCGCTAC  18960
CACCCCAGCA TCGTTTAAAA GCCGGTCTTT GTGGTTCTTG CAGATATGGC CCTCACCTGC  19020
CGCCTCCGTT TCCCGGTGCC GGGATTCCGA GGAAGAATGC ACCGTAGGAG GGGCATGGCC  19080
GGCCACGGCC TGACGGGCGG CATGCGTCGT GCGCACCACC GGCGGCGGCG CGCGTCGCAC  19140
CGTCGCATGC GCGGCGGTAT CCTGCCCCTC CTTATTCCAC TGATCGCCGC GGCGATTGGC  19200
GCCGTGCCCG GAATTGCATC CGTGGCCTTG CAGGCGCAGA GACACTGATT AAAAACAAGT  19260
TGCATGTGGA AAAATCAAAA TAAAAAGTCT GGACTCTCAC GCTCGCTTGG TCCTGTAACT  19320
ATTTTGTAGA ATGGAAGACA TCAACTTTGC GTCTCTGGCC CCGCGACACG GCTCGCGCCC  19380
GTTCATGGGA AACTGGCAAG ATATCGGCAC CAGCAATATG AGCGGTGGCG CCTTCAGCTG  19440
GGGCTCGCTG TGGAGCGGCA TTAAAAATTT CGGTTCCACC GTTAAGAACT ATGGCAGCAA  19500
GGCCTGGAAC AGCAGCACAG GCCAGATGCT GAGGGATAAG TTGAAAGAGC AAAATTTCCA  19560
ACAAAAGGTG GTAGATGGCC TGGCCTCTGG CATTAGCGGG GTGGTGGACC TGGCCAACCA  19620
GGCAGTGCAA AATAAGATTA ACAGTAAGCT TGATCCCCGC CCTCCCGTAG AGGAGCCTCC  19680
ACCGGCCGTG GAGACAGTGT CTCCAGAGGG GCGTGGCGAA AAGCGTCCGC GCCCCGACAG  19740
GGAAGAAACT CTGGTGACGC AAATAGACGA GCCTCCCTCG TACGAGGAGG CACTAAAGCA  19800
AGGCCTGCCC ACCACCCGTC CCATCGCGCC CATGGCTACC GGAGTGCTGG GCCAGCACAC  19860
ACCCGTAACG CTGGACCTGC CTCCCCCCGC CGACACCCAG CAGAAACCTG TGCTGCCAGG  19920
CCCGACCGCC GTTGTTGTAA CCCGTCCTAG CCGCGCGTCC CTGCGCCGCG CCGCCAGCGG  19980
TCCGCGATCG TTGCGGCCCG TAGCCAGTGG CAACTGGCAA AGCACACTGA ACAGCATCGT  20040
```

-continued

```
GGGTCTGGGG GTGCAATCCC TGAAGCGCCG ACGATGCTTC TGAATAGCTA ACGTGTCGTA  20100

TGTGTGTCAT GTATGCGTCC ATGTCGCCGC CAGAGGAGCT GCTGAGCCGC CGCGCGCCCG  20160

CTTTCCAAGA TGGCTACCCC TTCGATGATG CCGCAGTGGT CTTACATGCA CATCTCGGGC  20220

CAGGACGCCT CGGAGTACCT GAGCCCCGGG CTGGTGCAGT TTGCCCGCGC CACCGAGACG  20280

TACTTCAGCC TGAATAACAA GTTTAGAAAC CCCACGGTGG CGCCTACGCA CGACGTGACC  20340

ACAGACCGGT CCCAGCGTTT GACGCTGCGG TTCATCCCTG TGGACCGTGA GGATACTGCG  20400

TACTCGTACA AGGCGCGGTT CACCCTAGCT GTGGGTGATA ACCGTGTGCT GGACATGGCT  20460

TCCACGTACT TTGACATCCG CGGCGTGCTG GACAGGGGCC CTACTTTTAA GCCCTACTCT  20520

GGCACTGCCT ACAACGCCCT GGCTCCCAAG GGTGCCCCAA ATCCTTGCGA ATGGGATGAA  20580

GCTGCTACTG CTCTTGAAAT AAACCTAGAA GAAGAGGACG ATGACAACGA AGACGAAGTA  20640

GACGAGCAAG CTGAGCAGCA AAAAACTCAC GTATTTGGGC AGGCGCCTTA TTCTGGTATA  20700

AATATTACAA AGGAGGGTAT TCAAATAGGT GTCGAAGGTC AAACACCTAA ATATGCCGAT  20760

AAAACATTTC AACCTGAACC TCAAATAGGA GAATCTCAGT GGTACGAAAC TGAAATTAAT  20820

CATGCAGCTG GGAGAGTCCT TAAAAAGACT ACCCCAATGA AACCATGTTA CGGTTCATAT  20880

GCAAAACCCA CAAATGAAAA TGGAGGGCAA GGCATTCTTG TAAAGCAACA AAATGGAAAG  20940

CTAGAAAGTC AAGTGGAAAT GCAATTTTTC TCAACTACTG AGGCGACCGC AGGCAATGGT  21000

GATAACTTGA CTCCTAAAGT GGTATTGTAC AGTGAAGATG TAGATATAGA AACCCCAGAC  21060

ACTCATATTT CTTACATGCC CACTATTAAG GAAGGTAACT CACGAGAACT AATGGGCCAA  21120

CAATCTATGC CCAACAGGCC TAATTACATT GCTTTTAGGG ACAATTTTAT TGGTCTAATG  21180

TATTACAACA GCACGGGTAA TATGGGTGTT CTGGCGGGCC AAGCATCGCA GTTGAATGCT  21240

GTTGTAGATT TGCAAGACAG AAACACAGAG CTTTCATACC AGCTTTTGCT TGATTCCATT  21300

GGTGATAGAA CCAGGTACTT TTCTATGTGG AATCAGGCTG TTGACAGCTA TGATCCAGAT  21360

GTTAGAATTA TTGAAAATCA TGGAACTGAA GATGAACTTC CAAATTACTG CTTTCCACTG  21420

GGAGGTGTGA TTAATACAGA GACTCTTACC AAGGTAAAAC CTAAAACAGG TCAGGAAAAT  21480

GGATGGGAAA AAGATGCTAC AGAATTTTCA GATAAAAATG AAATAAGAGT TGGAAATAAT  21540

TTTGCCATGG AAATCAATCT AAATGCCAAC CTGTGGAGAA ATTTCCTGTA CTCCAACATA  21600

GCGCTGTATT TGCCCGACAA GCTAAAGTAC AGTCCTTCCA ACGTAAAAAT TTCTGATAAC  21660

CCAAACACCT ACGACTACAT GAACAAGCGA GTGGTGGCTC CCGGGTTAGT GGACTGCTAC  21720

ATTAACCTTG GAGCACGCTG GTCCCTTGAC TATATGGACA ACGTCAACCC ATTTAACCAC  21780

CACCGCAATG CTGGCCTGCG CTACCGCTCA ATGTTGCTGG GCAATGGTCG CTATGTGCCC  21840

TTCCACATCC AGGTGCCTCA GAAGTTCTTT GCCATTAAAA ACCTCCTTCT CCTGCCGGGC  21900

TCATACACCT ACGAGTGGAA CTTCAGGAAG GATGTTAACA TGGTTCTGCA GAGCTCCCTA  21960

GGAAATGACC TAAGGGTTGA CGGAGCCAGC ATTAAGTTTG ATAGCATTTG CCTTTACGCC  22020

ACCTTCTTCC CCATGGCCCA CAACACCGCC TCCACGCTTG AGGCCATGCT TAGAAACGAC  22080

ACCAACGACC AGTCCTTTAA CGACTATCTC TCCGCCGCCA ACATGCTCTA CCCTATACCC  22140

GCCAACGCTA CCAACGTGCC CATATCCATC CCCTCCCGCA ACTGGGCGGC TTTCCGCGGC  22200

TGGGCCTTCA CGCGCCTTAA GACTAAGGAA ACCCCATCAC TGGGCTCGGG CTACGACCCT  22260

TATTACACCT ACTCTGGCTC TATACCCTAC CTAGATGGAA CCTTTTACCT CAACCACACC  22320

TTTAAGAAGG TGGCCATTAC CTTTGACTCT TCTGTCAGCT GGCCTGGCAA TGACCGCCTG  22380

CTTACCCCCA ACGAGTTTGA AATTAAGCGC TCAGTTGACG GGGAGGGTTA CAACGTTGCC  22440
```

-continued

```
CAGTGTAACA TGACCAAAGA CTGGTTCCTG GTACAAATGC TAGCTAACTA CAACATTGGC  22500

TACCAGGGCT TCTATATCCC AGAGAGCTAC AAGGACCGCA TGTACTCCTT CTTTAGAAAC  22560

TTCCAGCCCA TGAGCCGTCA GGTGGTGGAT GATACTAAAT ACAAGGACTA CCAACAGGTG  22620

GGCATCCTAC ACCAACACAA CAACTCTGGA TTTGTTGGCT ACCTTGCCCC CACCATGCGC  22680

GAAGGACAGG CCTACCCTGC TAACTTCCCC TATCCGCTTA TAGGCAAGAC CGCAGTTGAC  22740

AGCATTACCC AGAAAAAGTT TCTTTGCGAT CGCACCCTTT GGCGCATCCC ATTCTCCAGT  22800

AACTTTATGT CCATGGGCGC ACTCACAGAC CTGGGCCAAA ACCTTCTCTA CGCCAACTCC  22860

GCCCACGCGC TAGACATGAC TTTTGAGGTG GATCCCATGG ACGAGCCCAC CCTTCTTTAT  22920

GTTTTGTTTG AAGTCTTTGA CGTGGTCCGT GTGCACCGGC CGCACCGCGG CGTCATCGAA  22980

ACCGTGTACC TGCGCACGCC CTTCTCGGCC GGCAACGCCA CAACATAAAG AAGCAAGCAA  23040

CATCAACAAC AGCTGCCGCC ATGGGCTCCA GTGAGCAGGA ACTGAAAGCC ATTGTCAAAG  23100

ATCTTGGTTG TGGGCCATAT TTTTTGGGCA CCTATGACAA GCGCTTTCCA GGCTTTGTTT  23160

CTCCACACAA GCTCGCCTGC GCCATAGTCA ATACGGCCGG TCGCGAGACT GGGGGCGTAC  23220

ACTGGATGGC CTTTGCCTGG AACCCGCACT CAAAAACATG CTACCTCTTT GAGCCCTTTG  23280

GCTTTTCTGA CCAGCGACTC AAGCAGGTTT ACCAGTTTGA GTACGAGTCA CTCCTGCGCC  23340

GTAGCGCCAT TGCTTCTTCC CCCGACCGCT GTATAACGCT GGAAAAGTCC ACCCAAAGCG  23400

TACAGGGGCC CAACTCGGCC GCCTGTGGAC TATTCTGCTG CATGTTTCTC CACGCCTTTG  23460

CCAACTGGCC CCAAACTCCC ATGGATCACA ACCCCACCAT GAACCTTATT ACCGGGGTAC  23520

CCAACTCCAT GCTCAACAGT CCCCAGGTAC AGCCCACCCT GCGTCGCAAC CAGGAACAGC  23580

TCTACAGCTT CCTGGAGCGC CACTCGCCCT ACTTCCGCAG CCACAGTGCG CAGATTAGGA  23640

GCGCCACTTC TTTTTGTCAC TTGAAAAACA TGTAAAAATA ATGTACTAGA GACACTTTCA  23700

ATAAAGGCAA ATGCTTTTAT TTGTACACTC TCGGGTGATT ATTTACCCCC ACCCTTGCCG  23760

TCTGCGCCGT TTAAAAATCA AAGGGGTTCT GCCGCGCATC GCTATGCGCC ACTGGCAGGG  23820

ACACGTTGCG ATACTGGTGT TTAGTGCTCC ACTTAAACTC AGGCACAACC ATCCGCGGCA  23880

GCTCGGTGAA GTTTTCACTC CACAGGCTGC GCACCATCAC CAACGCGTTT AGCAGGTCGG  23940

GCGCCGATAT CTTGAAGTCG CAGTTGGGGC CTCCGCCCTG CGCGCGCGAG TTGCGATACA  24000

CAGGGTTGCA GCACTGGAAC ACTATCAGCG CCGGGTGGTG CACGCTGGCC AGCACGCTCT  24060

TGTCGGAGAT CAGATCCGCG TCCAGGTCCT CCGCGTTGCT CAGGGCGAAC GGAGTCAACT  24120

TTGGTAGCTG CCTTCCCAAA AAGGGCGCGT GCCCAGGCTT TGAGTTGCAC TCGCACCGTA  24180

GTGGCATCAA AAGGTGACCG TGCCCGGTCT GGGCGTTAGG ATACAGCGCC TGCATAAAAG  24240

CCTTGATCTG CTTAAAAGCC ACCTGAGCCT TTGCGCCTTC AGAGAAGAAC ATGCCGCAAG  24300

ACTTGCCGGA AAACTGATTG GCCGGACAGG CCGCGTCGTG CACGCAGCAC CTTGCGTCGG  24360

TGTTGGAGAT CTGCACCACA TTTCGGCCCC ACCGGTTCTT CACGATCTTG GCCTTGCTAG  24420

ACTGCTCCTT CAGCGCGCGC TGCCCGTTTT CGCTCGTCAC ATCCATTTCA ATCACGTGCT  24480

CCTTATTTAT CATAATGCTT CCGTGTAGAC ACTTAAGCTC GCCTTCGATC TCAGCGCAGC  24540

GGTGCAGCCA CAACGCGCAG CCCGTGGGCT CGTGATGCTT GTAGGTCACC TCTGCAAACG  24600

ACTGCAGGTA CGCCTGCAGG AATCGCCCCA TCATCGTCAC AAAGGTCTTG TTGCTGGTGA  24660

AGGTCAGCTG CAACCCGCGG TGCTCCTCGT TCAGCCAGGT CTTGCATACG GCCGCCAGAG  24720

CTTCCACTTG GTCAGGCAGT AGTTTGAAGT TCGCCTTTAG ATCGTTATCC ACGTGGTACT  24780
```

-continued

```
TGTCCATCAG CGCGCGCGCA GCCTCCATGC CCTTCTCCCA CGCAGACACG ATCGGCACAC  24840
TCAGCGGGTT CATCACCGTA ATTTCACTTT CCGCTTCGCT GGGCTCTTCC TCTTCCTCTT  24900
GCGTCCGCAT ACCACGCGCC ACTGGGTCGT CTTCATTCAG CCGCCGCACT GTGCGCTTAC  24960
CTCCTTTGCC ATGCTTGATT AGCACCGGTG GGTTGCTGAA ACCCACCATT TGTAGCGCCA  25020
CATCTTCTCT TTCTTCCTCG CTGTCCACGA TTACCTCTGG TGATGGCGGG CGCTCGGGCT  25080
TGGGAGAAGG GCGCTTCTTT TTCTTCTTGG GCGCAATGGC CAAATCCGCC GCCGAGGTCG  25140
ATGGCCGCGG GCTGGGTGTG CGCGGCACCA GCGCGTCTTG TGATGAGTCT TCCTCGTCCT  25200
CGGACTCGAT ACGCCGCCTC ATCCGCTTTT TTGGGGGCGC CCGGGGAGGC GGCGGCGACG  25260
GGGACGGGGA CGACACGTCC TCCATGGTTG GGGGACGTCG CGCCGCACCG CGTCCGCGCT  25320
CGGGGGTGGT TTCGCGCTGC TCCTCTTCCC GACTGGCCAT TTCCTTCTCC TATAGGCAGA  25380
AAAAGATCAT GGAGTCAGTC GAGAAGAAGG ACAGCCTAAC CGCCCCCTCT GAGTTCGCCA  25440
CCACCGCCTC CACCGATGCC GCCAACGCGC CTACCACCTT CCCCGTCGAG GCACCCCCGC  25500
TTGAGGAGGA GGAAGTGATT ATCGAGCAGG ACCCAGGTTT TGTAAGCGAA GACGACGAGG  25560
ACCGCTCAGT ACCAACAGAG GATAAAAAGC AAGACCAGGA CAACGCAGAG GCAAACGAGG  25620
AACAAGTCGG GCGGGGGGAC GAAAGGCATG GCGACTACCT AGATGTGGGA GACGACGTGC  25680
TGTTGAAGCA TCTGCAGCGC CAGTGCGCCA TTATCTGCGA CGCGTTGCAA GAGCGCAGCG  25740
ATGTGCCCCT CGCCATAGCG GATGTCAGCC TTGCCTACGA ACGCCACCTA TTCTCACCGC  25800
GCGTACCCCC CAAACGCCAA GAAAACGGCA CATGCGAGCC CAACCCGCGC CTCAACTTCT  25860
ACCCCGTATT TGCCGTGCCA GAGGTGCTTG CCACCTATCA CATCTTTTTC CAAAACTGCA  25920
AGATACCCCT ATCCTGCCGT GCCAACCGCA GCCGAGCGGA CAAGCAGCTG GCCTTGCGGC  25980
AGGGCGCTGT CATACCTGAT ATCGCCTCGC TCAACGAAGT GCCAAAAATC TTTGAGGGTC  26040
TTGGACGCGA CGAGAAGCGC GCGGCAAACG CTCTGCAACA GGAAAACAGC GAAAATGAAA  26100
GTCACTCTGG AGTGTTGGTG GAACTCGAGG GTGACAACGC GCGCCTAGCC GTACTAAAAC  26160
GCAGCATCGA GGTCACCCAC TTTGCCTACC CGGCACTTAA CCTACCCCCC AAGGTCATGA  26220
GCACAGTCAT GAGTGAGCTG ATCGTGCGCC GTGCGCAGCC CCTGGAGAGG GATGCAAATT  26280
TGCAAGAACA AACAGAGGAG GGCCTACCCG CAGTTGGCGA CGAGCAGCTA GCGCGCTGGC  26340
TTCAAACGCG CGAGCCTGCC GACTTGGAGG AGCGACGCAA ACTAATGATG GCCGCAGTGC  26400
TCGTTACCGT GGAGCTTGAG TGCATGCAGC GGTTCTTTGC TGACCCGGAG ATGCAGCGCA  26460
AGCTAGAGGA AACATTGCAC TACACCTTTC GACAGGGCTA CGTACGCCAG GCCTGCAAGA  26520
TCTCCAACGT GGAGCTCTGC AACCTGGTCT CCTACCTTGG AATTTTGCAC GAAAACCGCC  26580
TTGGGCAAAA CGTGCTTCAT TCCACGCTCA AGGGCGAGGC GCGCCGCGAC TACGTCCGCG  26640
ACTGCGTTTA CTTATTTCTA TGCTACACCT GGCAGACGGC CATGGGCGTT TGGCAGCAGT  26700
GCTTGGAGGA GTGCAACCTC AAGGAGCTGC AGAAACTGCT AAAGCAAAAC TTGAAGGACC  26760
TATGGACGGC CTTCAACGAG CGCTCCGTGG CCGCGCACCT GGCGGACATC ATTTTCCCCG  26820
AACGCCTGCT TAAAACCCTG CAACAGGGTC TGCCAGACTT CACCAGTCAA AGCATGTTGC  26880
AGAACTTTAG GAACTTTATC CTAGAGCGCT CAGGAATCTT GCCCGCCACC TGCTGTGCAC  26940
TTCCTAGCGA CTTTGTGCCC ATTAAGTACC GCGAATGCCC TCCGCCGCTT TGGGGCCACT  27000
GCTACCTTCT GCAGCTAGCC AACTACCTTG CCTACCACTC TGACATAATG GAAGACGTGA  27060
GCGGTGACGG TCTACTGGAG TGTCACTGTC GCTGCAACCT ATGCACCCCG CACCGCTCCC  27120
TGGTTTGCAA TTCGCAGCTG CTTAACGAAA GTCAAATTAT CGGTACCTTT GAGCTGCAGG  27180
```

-continued

```
GTCCCTCGCC TGACGAAAAG TCCGCGGCTC CGGGGTTGAA ACTCACTCCG GGGCTGTGGA  27240
CGTCGGCTTA CCTTCGCAAA TTTGTACCTG AGGACTACCA CGCCCACGAG ATTAGGTTCT  27300
ACGAAGACCA ATCCCGCCCG CCAAATGCGG AGCTTACCGC CTGCGTCATT ACCCAGGGCC  27360
ACATTCTTGG CCAATTGCAA GCCATCAACA AAGCCCGCCA AGAGTTTCTG CTACGAAAGG  27420
GACGGGGGGT TTACTTGGAC CCCCAGTCCG GCGAGGAGCT CAACCCAATC CCCCCGCCGC  27480
CGCAGCCCTA TCAGCAGCAG CCGCGGGCCC TTGCTTCCCA GGATGGCACC CAAAAAGAAG  27540
CTGCAGCTGC CGCCGCCACC CACGGACGAG GAGGAATACT GGGACAGTCA GGCAGAGGAG  27600
GTTTTGGACG AGGAGGAGGA GGACATGATG GAAGACTGGG AGAGCCTAGA CGAGGAAGCT  27660
TCCGAGGTCG AAGAGGTGTC AGACGAAACA CCGTCACCCT CGGTCGCATT CCCCTCGCCG  27720
GCGCCCCAGA AATCGGCAAC CGGTTCCAGC ATGGCTACAA CCTCCGCTCC TCAGGCGCCG  27780
CCGGCACTGC CCGTTCGCCG ACCCAACCGT AGATGGGACA CCACTGGAAC CAGGGCCGGT  27840
AAGTCCAAGC AGCCGCCGCC GTTAGCCCAA GAGCAACAAC AGCGCCAAGG CTACCGCTCA  27900
TGGCGCGGGC ACAAGAACGC CATAGTTGCT TGCTTGCAAG ACTGTGGGGG CAACATCTCC  27960
TTCGCCCGCC GCTTTCTTCT CTACCATCAC GGCGTGGCCT TCCCCCGTAA CATCCTGCAT  28020
TACTACCGTC ATCTCTACAG CCCATACTGC ACCGGCGGCA GCGGCAGCGG CAGCAACAGC  28080
AGCGGCCACA CAGAAGCAAA GGCGACCGGA TAGCAAGACT CTGACAAAGC CCAAGAAATC  28140
CACAGCGGCG GCAGCAGCAG GAGGAGGAGC GCTGCGTCTG GCGCCCAACG AACCCGTATC  28200
GACCCGCGAG CTTAGAAACA GGATTTTTCC CACTCTGTAT GCTATATTTC AACAGAGCAG  28260
GGGCCAAGAA CAAGAGCTGA AAATAAAAAA CAGGTCTCTG CGATCCCTCA CCCGCAGCTG  28320
CCTGTATCAC AAAAGCGAAG ATCAGCTTCG GCGCACGCTG GAAGACGCGG AGGCTCTCTT  28380
CAGTAAATAC TGCGCGCTGA CTCTTAAGGA CTAGTTTCGC GCCCTTTCTC AAATTTAAGC  28440
GCGAAAACTA CGTCATCTCC AGCGGCCACA CCCGGCGCCA GCACCTGTCG TCAGCGCCAT  28500
TATGAGCAAG GAAATTCCCA CGCCCTACAT GTGGAGTTAC CAGCCACAAA TGGGACTTGC  28560
GGCTGGAGCT GCCCAAGACT ACTCAACCCG AATAAACTAC ATGAGCGCGG GACCCCACAT  28620
GATATCCCGG GTCAACGGAA TCCGCGCCCA CCGAAACCGA ATTCTCTTGG AACAGGCGGC  28680
TATTACCACC ACACCTCGTA ATAACCTTAA TCCCCGTAGT TGGCCCGCTG CCCTGGTGTA  28740
CCAGGAAAGT CCCGCTCCCA CCACTGTGGT ACTTCCCAGA GACGCCCAGG CCGAAGTTCA  28800
GATGACTAAC TCAGGGGCGC AGCTTGCGGG CGGCTTTCGT CACAGGGTGC GGTCGCCCGG  28860
GCAGGGTATA ACTCACCTGA CAATCAGAGG GCGAGGTATT CAGCTCAACG ACGAGTCGGT  28920
GAGCTCCTCG CTTGGTCTCC GTCCGGACGG GACATTTCAG ATCGGCGGCG CCGGCCGTCC  28980
TTCATTCACG CCTCGTCAGG CAATCCTAAC TCTGCAGACC TCGTCCTCTG AGCCGCGCTC  29040
TGGAGGCATT GGAACTCTGC AATTTATTGA GGAGTTTGTG CCATCGGTCT ACTTTAACCC  29100
CTTCTCGGGA CCTCCCGGCC ACTATCCGGA TCAATTTATT CCTAACTTTG ACGCGGTAAA  29160
GGACTCGGCG GACGGCTACG ACTGAATGTT AAGTGGAGAG GCAGAGCAAC TGCGCCTGAA  29220
ACACCTGGTC CACTGTCGCC GCCACAAGTG CTTTGCCCGC GACTCCGGTG AGTTTTGCTA  29280
CTTTGAATTG CCCGAGGATC ATATCGAGGG CCCGGCGCAC GGCGTCCGGC TTACCGCCCA  29340
GGGAGAGCTT GCCCGTAGCC TGATTCGGGA GTTTACCCAG CGCCCCCTGC TAGTTGAGCG  29400
GGACAGGGGA CCCTGTGTTC TCACTGTGAT TTGCAACTGT CCTAACCTTG GATTACATCA  29460
AGATCTTTGT TGCCATCTCT GTGCTGAGTA TAATAAATAC AGAAATTAAA ATATACTGGG  29520
```

-continued

```
GCTCCTATCG CCATCCTGTA AACGCCACCG TCTTCACCCG CCCAAGCAAA CCAAGGCGAA  29580
CCTTACCTGG TACTTTTAAC ATCTCTCCCT CTGTGATTTA CAACAGTTTC AACCCAGACG  29640
GAGTGAGTCT ACGAGAGAAC CTCTCCGAGC TCAGCTACTC CATCAGAAAA AACACCACCC  29700
TCCTTACCTG CCGGGAACGT ACGAGTGCGT CACCGGCCGC TGCACCACAC CTACCGCCTG  29760
ACCGTAAACC AGACTTTTTC CGGACAGACC TCAATAACTC TGTTTACCAG AACAGGAGGT  29820
GAGCTTAGAA AACCCTTAGG GTATTAGGCC AAAGGCGCAG CTACTGTGGG GTTTATGAAC  29880
AATTCAAGCA ACTCTACGGG CTATTCTAAT TCAGGTTTCT CTAGAATCGG GGTTGGGGTT  29940
ATTCTCTGTC TTGTGATTCT CTTTATTCTT ATACTAACGC TTCTCTGCCT AAGGCTCGCC  30000
GCCTGCTGTG TGCACATTTG CATTTATTGT CAGCTTTTTA AACGCTGGGG TCGCCACCCA  30060
AGATGATTAG GTACATAATC CTAGGTTTAC TCACCCTTGC GTCAGCCCAC GGTACCACCC  30120
AAAAGGTGGA TTTTAAGGAG CCAGCCTGTA ATGTTACATT CGCAGCTGAA GCTAATGAGT  30180
GCACCACTCT TATAAAATGC ACCACAGAAC ATGAAAAGCT GCTTATTCGC CACAAAAACA  30240
AAATTGGCAA GTATGCTGTT TATGCTATTT GGCAGCCAGG TGACACTACA GAGTATAATG  30300
TTACAGTTTT CCAGGGTAAA AGTCATAAAA CTTTTATGTA TACTTTTCCA TTTTATGAAA  30360
TGTGCGACAT TACCATGTAC ATGAGCAAAC AGTATAAGTT GTGGCCCCCA CAAAATTGTG  30420
TGGAAAACAC TGGCACTTTC TGCTGCACTG CTATGCTAAT TACAGTGCTC GCTTTGGTCT  30480
GTACCCTACT CTATATTAAA TACAAAAGCA GACGCAGCTT TATTGAGGAA AAGAAAATGC  30540
CTTAATTTAC TAAGTTACAA AGCTAATGTC ACCACTAACT GCTTTACTCG CTGCTTGCAA  30600
AACAAATTCA AAAAGTTAGC ATTATAATTA GAATAGGATT TAAACCCCCC GGTCATTTCC  30660
TGCTCAATAC CATTCCCCTG AACAATTGAC TCTATGTGGG ATATGCTCCA GCGCTACAAC  30720
CTTGAAGTCA GGCTTCCTGG ATGTCAGCAT CTGACTTTGG CCAGCACCTG TCCCGCGGAT  30780
TTGTTCCAGT CCAACTACAG CGACCCACCC TAACAGAGAT GACCAACACA ACCAACGCGG  30840
CCGCCGCTAC CGGACTTACA TCTACCACAA ATACACCCCA AGTTTCTGCC TTTGTCAATA  30900
ACTGGGATAA CTTGGGCATG TGGTGGTTCT CCATAGCGCT TATGTTTGTA TGCCTTATTA  30960
TTATGTGGCT CATCTGCTGC CTAAAGCGCA AACGCGCCCG ACCACCCATC TATAGTCCCA  31020
TCATTGTGCT ACACCCAAAC AATGATGGAA TCCATAGATT GGACGGACTG AAACACATGT  31080
TCTTTTCTCT TACAGTATGA TTAAATGAGA CATGATTCCT CGAGTTTTTA TATTACTGAC  31140
CCTTGTTGCG CTTTTTTGTG CGTGCTCCAC ATTGGCTGCG GTTTCTCACA TCGAAGTAGA  31200
CTGCATTCCA GCCTTCACAG TCTATTTGCT TTACGGATTT GTCACCCTCA CGCTCATCTG  31260
CAGCCTCATC ACTGTGGTCA TCGCCTTTAT CCAGTGCATT GACTGGGTCT GTGTGCGCTT  31320
TGCATATCTC AGACACCATC CCCAGTACAG GGACAGGACT ATAGCTGAGC TTCTTAGAAT  31380
TCTTTAATTA TGAAATTTAC TGTGACTTTT CTGCTGATTA TTTGCACCCT ATCTGCGTTT  31440
TGTTCCCCGA CCTCCAAGCC TCAAAGACAT ATATCATGCA GATTCACTCG TATATGGAAT  31500
ATTCCAAGTT GCTACAATGA AAAAAGCGAT CTTTCCGAAG CCTGGTTATA TGCAATCATC  31560
TCTGTTATGG TGTTCTGCAG TACCATCTTA GCCCTAGCTA TATATCCCTA CCTTGACATT  31620
GGCTGGAAAC GAATAGATGC CATGAACCAC CCAACTTTCC CCGCGCCCGC TATGCTTCCA  31680
CTGCAACAAG TTGTTGCCGG CGGCTTTGTC CCAGCCAATC AGCCTCGCCC CACTTCTCCC  31740
ACCCCCACTG AAATCAGCTA CTTTAATCTA ACAGGAGGAG ATGACTGACA CCCTAGATCT  31800
AGAAATGGAC GGAATTATTA CAGAGCAGCG CCTGCTAGAA AGACGCAGGG CAGCGGCCGA  31860
GCAACAGCGC ATGAATCAAG AGCTCCAAGA CATGGTTAAC TTGCACCAGT GCAAAAGGGG  31920
```

-continued

```
TATCTTTTGT CTGGTAAAGC AGGCCAAAGT CACCTACGAC AGTAATACCA CCGGACACCG  31980
CCTTAGCTAC AAGTTGCCAA CCAAGCGTCA GAAATTGGTG GTCATGGTGG GAGAAAAGCC  32040
CATTACCATA ACTCAGCACT CGGTAGAAAC CGAAGGCTGC ATTCACTCAC CTTGTCAAGG  32100
ACCTGAGGAT CTCTGCACCC TTATTAAGAC CCTGTGCGGT CTCAAAGATC TTATTCCCTT  32160
TAACTAATAA AAAAAAATAA TAAAGCATCA CTTACTTAAA ATCAGTTAGC AAATTTCTGT  32220
CCAGTTTATT CAGCAGCACC TCCTTGCCCT CCTCCCAGCT CTGGTATTGC AGCTTCCTCC  32280
TGGCTGCAAA CTTTCTCCAC AATCTAAATG GAATGTCAGT TTCCTCCTGT TCCTGTCCAT  32340
CCGCACCCAC TATCTTCATG TTGTTGCAGA TGAAGCGCGC AAGACCGTCT GAAGATACCT  32400
TCAACCCCGT GTATCCATAT GACACGGAAA CCGGTCCTCC AACTGTGCCT TTTCTTACTC  32460
CTCCCTTTGT ATCCCCCAAT GGGTTTCAAG AGAGTCCCCC TGGGGTACTC TCTTTGCGCC  32520
TATCCGAACC TCTAGTTACC TCCAATGGCA TGCTTGCGCT CAAAATGGGC AACGGCCTCT  32580
CTCTGGACGA GGCCGGCAAC CTTACCTCCC AAAATGTAAC CACTGTGAGC CCACCTCTCA  32640
AAAAAACCAA GTCAAACATA AACCTGGAAA TATCTGCACC CCTCACAGTT ACCTCAGAAG  32700
CCCTAACTGT GGCTGCCGCC GCACCTCTAA TGGTCGCGGG CAACACACTC ACCATGCAAT  32760
CACAGGCCCC GCTAACCGTG CACGACTCCA AACTTAGCAT TGCCACCCAA GGACCCCTCA  32820
CAGTGTCAGA AGGAAAGCTA GCCCTGCAAA CATCAGGCCC CCTCACCACC ACCGATAGCA  32880
GTACCCTTAC TATCACTGCC TCACCCCCTC TAACTACTGC CACTGGTAGC TTGGGCATTG  32940
ACTTGAAAGA GCCCATTTAT ACACAAAATG GAAAACTAGG ACTAAAGTAC GGGGCTCCTT  33000
TGCATGTAAC AGACGACCTA AACACTTTGA CCGTAGCAAC TGGTCCAGGT GTGACTATTA  33060
ATAATACTTC CTTGCAAACT AAAGTTACTG GAGCCTTGGG TTTTGATTCA CAAGGCAATA  33120
TGCAACTTAA TGTAGCAGGA GGACTAAGGA TTGATTCTCA AAACAGACGC CTTATACTTG  33180
ATGTTAGTTA TCCGTTTGAT GCTCAAAACC AACTAAATCT AAGACTAGGA CAGGGCCCTC  33240
TTTTTATAAA CTCAGCCCAC AACTTGGATA TTAACTACAA CAAAGGCCTT TACTTGTTTA  33300
CAGCTTCAAA CAATTCCAAA AAGCTTGAGG TTAACCTAAG CACTGCCAAG GGGTTGATGT  33360
TTGACGCTAC AGCCATAGCC ATTAATGCAG GAGATGGGCT TGAATTTGGT TCACCTAATG  33420
CACCAAACAC AAATCCCCTC AAAACAAAAA TTGGCCATGG CCTAGAATTT GATTCAAACA  33480
AGGCTATGGT TCCTAAACTA GGAACTGGCC TTAGTTTTGA CAGCACAGGT GCCATTACAG  33540
TAGGAAACAA AAATAATGAT AAGCTAACTT TGTGGACCAC ACCAGCTCCA TCTCCTAACT  33600
GTAGACTAAA TGCAGAGAAA GATGCTAAAC TCACTTTGGT CTTAACAAAA TGTGGCAGTC  33660
AAATACTTGC TACAGTTTCA GTTTTGGCTG TTAAAGGCAG TTTGGCTCCA ATATCTGGAA  33720
CAGTTCAAAG TGCTCATCTT ATTATAAGAT TTGACGAAAA TGGAGTGCTA CTAAACAATT  33780
CCTTCCTGGA CCCAGAATAT TGGAACTTTA GAAATGGAGA TCTTACTGAA GGCACAGCCT  33840
ATACAAACGC TGTTGGATTT ATGCCTAACC TATCAGCTTA TCCAAAATCT CACGGTAAAA  33900
CTGCCAAAAG TAACATTGTC AGTCAAGTTT ACTTAAACGG AGACAAAACT AAACCTGTAA  33960
CACTAACCAT TACACTAAAC GGTACACAGG AAACAGGAGA CACAACTCCA AGTGCATACT  34020
CTATGTCATT TTCATGGGAC TGGTCTGGCC ACAACTACAT TAATGAAATA TTTGCCACAT  34080
CCTCTTACAC TTTTTCATAC ATTGCCCAAG AATAAAGAAT CGTTTGTGTT ATGTTTCAAC  34140
GTGTTTATTT TTCAATTGCA GAAAATTTCA AGTCATTTTT CATTCAGTAG TATAGCCCCA  34200
CCACCACATA GCTTATACAG ATCACCGTAC CTTAATCAAA CTCACAGAAC CCTAGTATTC  34260
```

-continued

```
AACCTGCCAC CTCCCTCCCA ACACACAGAG TACACAGTCC TTTCTCCCCG GCTGGCCTTA  34320

AAAAGCATCA TATCATGGGT AACAGACATA TTCTTAGGTG TTATATTCCA CACGGTTTCC  34380

TGTCGAGCCA AACGCTCATC AGTGATATTA ATAAACTGGC GGCGATATAA AATGCAAGGT  34440

GCTGCTCAAA AAATCAGGCA AAGCCTCGCG CAAAAAAGAA AGCACATCGT AGTCATGCTC  34500

ATGCAGATAA AGGCAGGTAA GCTCCGGAAC CACCACAGAA AAAGACACCA TTTTTCTCTC  34560

AAACATGTCT GCGGGTTTCT GCATAAACAC AAAATAAAAT AACAAAAAAA CATTTAAACA  34620

TTAGAAGCCT GTCTTACAAC AGGAAAAACA ACCCTTATAA GCATAAGACG GACTACGGCC  34680

ATGCCGGCGT GACCGTAAAA AAACTGGTCA CCGTGATTAA AAAGCACCAC CGACAGCTCC  34740

TCGGTCATGT CCGGAGTCAT AATGTAAGAC TCGGTAAACA CATCAGGTTG ATTCATCGGT  34800

CAGTGCTAAA AAGCGACCGA AATAGCCCGG GGGAATACAT ACCCGCAGGC GTAGAGACAA  34860

CATTACAGCC CCCATAGGAG GTATAACAAA ATTAATAGGA GAGAAAAACA CATAAACACC  34920

TGAAAAACCC TCCTGCCTAG GCAAAATAGC ACCCTCCCGC TCCAGAACAA CATACAGCGC  34980

TTCACAGCGG CAGCCTAACA GTCAGCCTTA CCAGTAAAAA AGAAAACCTA TTAAAAAAAC  35040

ACCACTCGAC ACGGCACCAG CTCAATCAGT CACAGTGTAA AAAAGGGCCA AGTGCAGAGC  35100

GAGTATATAT AGGACTAAAA AATGACGTAA CGGTTAAAGT CCACAAAAAA CACCCAGAAA  35160

ACCGCACGCG AACCTACGCC CAGAAACGAA AGCCAAAAAA CCCACAACTT CCTCAAATCG  35220

TCACTTCCGT TTTCCCACGT TACGTAACTT CCCATTTTAA GAAAACTACA ATTCCCAACA  35280

CATACAAGTT ACTCCGCCCT AAAACCTACG TCACCCGCCC CGTTCCCACG CCCCGCGCCA  35340

CGTCACAAAC TCCACCCCCT CATTATCATA TTGGCTTCAA TCCAAAATAA GGTATATTAT  35400

TGATGATG                                                           35408
```

ADENOVIRUS GENE THERAPY VEHICLE AND CELL LINE

CROSS-REFERENCE TO OTHER APPLICATIONS

This is a continuation-in-part application of U.S. patent application Ser. No. 08/462,014, filed Jun. 5, 1995, now issued as U.S. Pat. No. 5,756,283. The disclosure of this parent application is incorporated by reference herein.

This invention was supported by the National Institute of Health Grant Nos. HD32649-01 and DK49136. The United States government has rights in this invention.

FIELD OF THE INVENTION

The present invention relates to the field of somatic gene therapy and the treatment of genetic disorders.

BACKGROUND OF THE INVENTION

Adenoviruses are eukaryotic DNA viruses that can be modified to efficiently deliver a therapeutic or reporter transgene to a variety of cell types. Human adenoviruses are comprised of a linear, approximately 36 kb double-stranded DNA genome, which is divided into 100 map units (m.u.), each of which is 360 bp in length. The DNA contains short inverted terminal repeats (ITR) at each end of the genome that are required for viral DNA replication. The gene products are organized into early (E1 through E4) and late (L1 through L5) regions, based on expression before or after the initiation of viral DNA synthesis [see, e.g., M. S. Horwitz et al, "Adenoviridae and Their Replication", *Virology*, second edition, pp. 1712, ed. B. N. Fields et al, Raven Press Ltd., New York (1990)]. The adenoviruses types 2 and 5 (Ad2 and Ad5, respectively), are not associated with human malignancies.

Recombinant adenoviruses are capable of providing extremely high levels of transgene delivery to virtually all cell types, regardless of the mitotic state. The efficacy of this system in delivering a therapeutic transgene in vivo that complements a genetic imbalance has been demonstrated in animal models of various disorders [K. F. Kozarsky et al, *Somatic Cell Mol. Genet*., 19:449–458 (1993) ("Kozarsky et al I"); K. F. Kozarsky et al, *J. Biol. Chem.*, 269:13695–13702 (1994) ("Kozarsky et al II); Y. Watanabe, *Atherosclerosis*, 36:261–268 (1986); K. Tanzawa et al, *FEBS Letters*, 118(1):81–84 (1980); J. L. Golasten et al, *New Engl. J. Med*., 309(11983):288–296 (1983); S. Ishibashi et al, *J. Clin. Invest*., 92:883–893 (1993); and S. Ishibashi et al, *J. Clin. Invest*., 93:1885–1893 (1994)]. The use of recombinant adenoviruses in the transduction of genes into hepatocytes in vivo has previously been demonstrated in rodents and rabbits [see, e.g., Kozarsky II, cited above, and S. Ishibashi et al, *J. Clin. Invest*., 92:883–893 (1993)].

The first-generation recombinant, replication-deficient adenoviruses which have been developed for gene therapy contain deletions of the entire E1a and part of the E1b regions. This replication-defective virus is grown on an adenovirus-transformed, complementation human embryonic kidney cell line containing a functional adenovirus E1a gene which provides a transacting E1a protein, the 293 cell [ATCC CRL1573]. E1-deleted viruses are capable of replicating and producing infectious virus in the 293 cells, which provide E1a and E1b region gene products in trans. The resulting virus is capable of infecting many cell types and can express the introduced gene (providing it carries its own promoter), but cannot replicate in a cell that does not carry the E1 region DNA unless the cell is infected at a very high multiplicity of infection.

However, in vivo studies revealed transgene expression in these E1 deleted vectors was transient and invariably associated with the development of severe inflammation at the site of vector targeting [S. Ishibashi et al, *J. Clin. Invest*., 93:1885–1893 (1994); J. M. Wilson et al, *Proc. Natl. Acad. Sci., USA*, 85:4421–4424 (1988); J. M. Wilson et al, *Clin. Bio*., 3:21–26 (1991); M. Grossman et al, *Som. Cell. and Mol. Gen*., 17:601–607 (1991)]. Antigenic targets for immune mediated clearance are viral proteins expressed from the recombinant viral genome and/or the product of the transgene [Y. Yang et al, *Proc. Natl. Acad. Sci., USA*, 91:4407–4411 (May 1994); Y. Yang et al, *Immun*., 1:433–442 (August 1994)].

There remains a need in the art for additional recombinant adenoviruses, therapeutic compositions and methods which enable effective treatment of disorders and diseases by gene therapy.

SUMMARY OF THE INVENTION

In one aspect of this invention, a novel packaging cell line is provided which expresses adenovirus genes E1a, E1b and E4, or functional fragments thereof. In one embodiment, the E4 gene fragment is open reading frame (ORF) 6 under the control of an inducible promoter.

In another aspect, the invention provides a recombinant adenovirus comprising the DNA of, or corresponding to, at least a portion of the genome of an adenovirus having functional deletions of the E1 and E4 gene regions; a suitable gene operatively linked to regulatory sequences directing its expression, and an adenovirus capsid, the recombinant virus capable of infecting a mammalian cell and expressing the gene product in the cell in vivo or in vitro. In a preferred embodiment, the cell is a muscle cell.

In another aspect, the invention provides a mammalian cell infected with the recombinant virus described above.

In still another aspect, the invention provides a recombinant adenovirus shuttle vector comprising the DNA of, or corresponding to, at least a portion of the genome of an adenovirus having functional deletions of the E1 and E4 gene regions; a suitable gene operatively linked to regulatory sequences capable of directing its expression; and plasmid sequences.

In still a further aspect, the invention provides a method for delivering and stably integrating a selected gene into a mammalian cell comprising introducing into said cell an effective amount of a recombinant virus described above.

In another aspect, the invention provides a method for producing the above-described recombinant Ad virus by co-transfecting the shuttle vector described above and a helper adenovirus into the packaging cell line described above, wherein the transfected cell generates the recombinant adenovirus. The recombinant adenovirus is subsequently isolated and purified therefrom.

Other aspects and advantages of the present invention are described further in the following detailed description of the preferred embodiments thereof.

BRIEF DESCRIPTION OF THE DRAWINGS

FIGS. 2A through 2F provides the continuous DNA sequence [SEQ ID NO: 1] of the minigene containing the MMTV promoter in operative control of the adenovirus serotype 5 E4 gene open reading frame 6. Nucleotides 1–1506 provide the MMTV promoter. Nucleotides 1523–2408 span E4 ORF6 and the amino acid sequence of ORF 6 [SEQ ID NO: 2] is indicated under the ORF DNA sequence. Nucleotides 2409–3654 span the growth hormone gene (GH) terminator sequences, which provide the polyadenylation site.

FIGS. 4A–4CC provide the DNA sequence [SEQ ID NO: 3] of recombinant adenovirus H5.001CBLacZ in which nucleotides 1–330 span Ad map units 0–1; nucleotides 370–928 span the CMV enhancer/chicken β-actin promoter (CB); nucleotides 945–4429 encode *E. coli* β-galactosidase, nucleotides 4429–4628 span the polyadenylation sequence; and nucleotides 4671–35408 span Ad5 sequences m.u. 9.2 to about m.u. 92.1 and from about m.u. 97.3 to m.u. 100 (containing a substantial deletion of the E4 gene between m.u. 92 through 97.2).

DETAILED DESCRIPTION OF THE INVENTION

Figure 1:
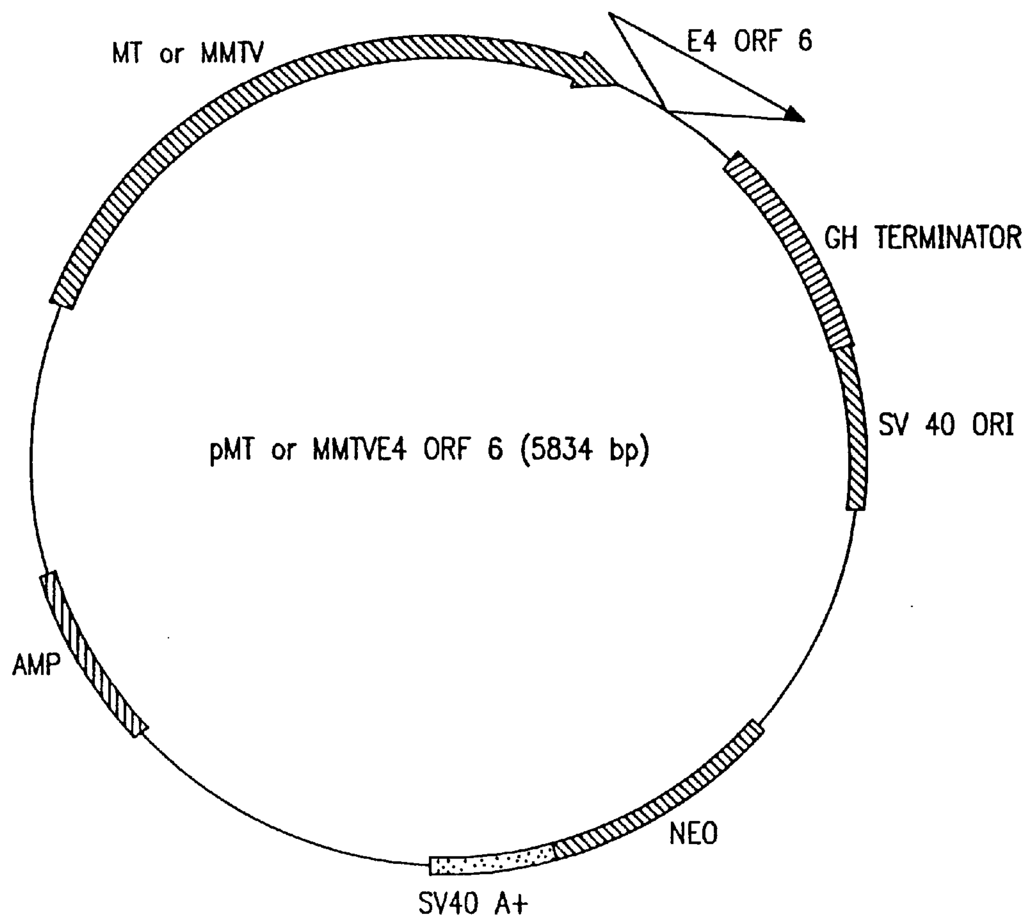
FIG. 1 is a schematic drawing of an exemplary plasmid useful for the construction of a packaging cell line of this invention. Plasmid pMMTVE4ORF6 or pMTE4ORF6, which contains a mouse mammary tumor virus promoter (MMTV promoter) or a sheep metallothionine promoter (MT promoter), respectively, in control of a human E4 ORF 6 gene sequence, a growth hormone gene terminator sequence (GH), an SV40 origin of replication, plasmid sequences from a pBR322-based plasmid including a neomycin resistance gene, an SV40 polyadenylation site and an ampicillin resistance gene.

The present invention provides novel packaging cell lines, which enable the production of recombinant adenoviruses functionally deleted in both the E1 and E4 genes, and methods which enable the therapeutic treatment of disorders with such recombinant adenoviruses.

To increase the transgene capacity and decrease immune response of recombinant adenoviral vectors, as many viral genes as possible should be deleted to inactivate the adenovirus. However, it is crucial to generate complementing cell lines for construction and propagation of such deleted adenoviral vectors. The method and compositions of the present invention overcome several problems previously identified in the gene therapy for first generation E1 deleted adenoviruses and display advantages in administration particularly to muscle tissue.

I. Novel Packaging Cell Lines

Early region 4 (E4) of adenovirus serotype 5 consists of 7 open reading frames (ORFs) believed to be involved in viral DNA replication, host cell shut-off, and late mRNA accumulation. To generate recombinant adenoviruses (Ad) deleted in E4, the function of the E4 region must be supplied to the recombinant virus by a helper virus or packaging cell line. However, useful packaging cell lines have not been available because normally the continuous expression of functioning Ad E1 and functional E4 in a single cell line are toxic to the cell. Such cells are therefore not useful for the growth and replication of recombinant adenoviruses. Further, the DNA encoding the functional Ad E1 and Ad E4 genes, when present in a packaging cell line, can increase the chances of recombination with a recombinant Ad virus to cause the virus to revert to a wildtype Ad virus.

The present invention avoids these problems by providing a packaging cell line which contains the Ad5 E1 gene and only the ORF 6 of the Ad5 E4 gene. ORF6 of E4 alone can provide the requirements for E4 in the viral life cycle. According to this invention, the ORF6 is further preferably under the transcriptional control of an inducible promoter, such as the sheep metallothionine promoter, inducible by zinc, or the mouse mammary tumor virus (MMTV) promoter, inducible by a glucocorticoid, particularly, dexamethasone. This packaging cell line permits one to control the development of toxicity by regulating the expression of the E4 ORF6 gene. After the desired shuttle vector containing the adenoviral sequences is transfected into the cell line, expression of the E4 ORF6 can be induced by the appropriate inducer. The packaging cell is thus able to provide both Ad E1 and Ad E4 ORF6 gene products to the recombinant virus for a sufficient period to allow productive infection and recovery of the recombinant virus, before the cell becomes toxic. At present, the time period before the cell experiences toxicity is about 10 days.

In its most preferred form, the packaging cell line is a human embryonic kidney (HEK) 293 E1 expressing cell line into which is introduced the E4 ORF 6 sequence under the control of an inducible promoter. The MMTV promoter with its glucocorticoid inducer is presently preferred, because the zinc sulfate inducer of the MT promoter can itself be toxic to the cells. However, other inducible promoters, such as those identified in International patent application WO95/13392, published May 18, 1995, and incorporated by reference herein may also be used in the production of packaging cell lines according to this invention. Constitutive promoters in control of the expression of ORF6 may be employed, such as the constitutive Ad5 E4 region promoter, LTR, but are less preferred.

It should be understood by one of skill in the art that another parent cell line may be selected for the generation of a novel cell line expressing the E1a, E1b, and E4 ORF6 genes of a selected adenovirus serotype. Among such parent cell lines may be included HeLa (CCL 2), A549 (CCL 185), KB (CCL 17), Detroit (e.g., Detroit 510, CCL 72) and WI-38 (ATCC CCL 75) cells. These cell lines are all available from the American Type Culture Collection, 10801 University Boulevard, Manassas, Va. 20110-2209, USA. Other suitable parent cell lines may be obtained from other sources. If such parent cell lines were selected for modification, the cell line would need to be further supplied with the E1a and E1b gene functions, e.g., such as by transfection with a plasmid containing these genes or functional fragments thereof under a suitable promoter, as well as with the ORF6 gene as described herein.

Example 1 below provides specific teaching of the construction of packaging cell lines containing only the ORF 6 of Ad5 E4 region or, for functional comparisons, the entire E4 region. Briefly described, the entire E4 region and an ORF6 sequence of Ad 5 E4 gene were obtained by known techniques [see, e.g., Sambrook et al., "Molecular Cloning. A Laboratory Manual.", 2d edit., Cold Spring Harbor Laboratory, New York (1989) and references cited therein]. To isolate the ORF6 region, the anchored polymerase chain reaction technique was used to amplify the ORF6 sequence from its initiation codon to its termination codon. Primers selected from the published sequence of ORF6 were used to amplify the ORF sequence and insert restriction sites onto the end of the sequence. The E4 ORF6 sequence itself is reproduced as nucleotides 1523 through 2408 of SEQ ID NO: 1 in FIG. 2. The entire E4 gene sequence is published in the Genbank sequence of Ad5 [Genbank Accession No. M73260].

A minigene was constructed that placed the ORF6 sequence under the control of a selected promoter. By "minigene" as used here is meant the combination of the ORF6 sequence and the other regulatory elements necessary to transcribe the sequence and express the gene product in a cell containing that minigene. The ORF6 sequence gene is operatively linked to regulatory components in a manner which permits its transcription. Such components include conventional regulatory elements, such as a promoter to drive ORF6 expression. One inducible promoter was an $Zn^{+2}$ inducible sheep metallothionine (MT) promoter [M. G. Peterson et al, *Eur. J. Biochem.*, 174:417–424 (1988)]. The second promoter, i.e, the promoter exemplified in FIG. 2, is the dexamethasone-inducible mouse mammary tumor virus (MMTV) promoter. The DNA sequence of the MMTV promoter spans nucleotides 1–1506 of SEQ ID NO: 1 in FIG. 2.

The minigene also contains nucleic acid sequences heterologous to the ORF6 viral sequence, including sequences providing signals required for efficient polyadenylation of the transcript (poly-A or pA). A common poly-A sequence which is employed in this invention is that derived from the growth hormone (GH) gene terminator sequence. The poly-A sequence generally is inserted in the minigene following the ORF6 sequence. The polyA sequence employed in the MMTV-ORF6 minigene described in Example 1 and FIG. 2 is supplied by the growth hormone gene terminator, which spans nucleotides 2409–3654 of SEQ ID NO: 1 in FIG. 2 and an SV40 origin of replication. A similar minigene differing in promoter sequence, polyA sequence and/or SV40 origin of replication sequence can also be designed by one of skill in the art to transfer the E4 ORF6 sequence to a shuttle plasmid. Selection of these and other common vector elements are conventional [see, e.g., Sambrook et al, "Molecular Cloning. A Laboratory Manual.", 2d edit., Cold Spring Harbor Laboratory, New York (1989) and references cited therein] and many such sequences are available from commercial and industrial sources as well as from Genbank.

The ORF6-containing minigene was subcloned into a pBR322-based shuttle plasmid that contained a neomycin resistance gene, resulting in the shuttle vector depicted in FIG. 1. Any of the many known bacterial shuttle vectors may be employed to carry the minigene, providing that the vector contains a reporter gene or selectable marker of which many, e.g., neo, amp or purimycin, are known in the art. It is expected that one of skill in the art can develop other suitable shuttle vectors using other plasmid components which are similarly capable of transferring the ORF6 minigene into the chromosome of a cell transfected with the plasmid.

As further described in Example 1, other shuttle vectors were designed for comparative purposes, which contain the complete or substantially complete Ad5 E4 region under the control of the constitutive retroviral MLV LTR sequence in the presence or absence of the endogenous E4 promoter. The shuttle plasmid carrying the ORF6 minigene (or the entire E4 region) was introduced into HEK 293 cells which express the Ad E1 gene products. Complementing cell lines were generated that express these Ad E4 or ORF6 genes from either their endogenous promoters or heterologous inducible promoters. These cell lines are further characterized by their genetic constitution, E4 protein synthesis, recombinant AAV helper function, relative plaque efficiency of H5dl1004 virus, and growth kinetics of recombinant E1/E4 deleted adenovirus. These characteristics of exemplary E1/E4 expressing packaging cell lines are discussed in detail in the following examples.

The E1/E4 ORF6 expressing packaging cell lines are useful in the generation of recombinant E1/E4 deleted adenoviruses. These recombinant adenoviruses are useful in transferring a selected transgene to a selected cell. In in vivo experiments with the recombinant virus grown in the packaging cell lines, the E1/E4 deleted recombinant virus demonstrated utility particularly in transferring a transgene to a muscle cell.

II. Recombinant Adenovirus

The novel E1/E4 expressing cell line is useful in further constructing E1/E4 deleted recombinant adenoviruses containing any selected transgene. The recombinant adenoviruses of this invention are capable of delivering a suitable gene to mammalian cells and tissues. These recombinant adenoviruses are functionally deleted in at least the E1a, E1b and E4 Ad gene regions. By the term "functionally deleted" is meant that a sufficient amount of the gene region is removed or otherwise damaged, e.g., by mutation or modification, so that the gene region is no longer capable of producing the products of gene expression. If desired, the entire gene region may be removed.

The adenovirus sequences used in the construction of the shuttle vectors, helper viruses, if needed, and recombinant viruses, and other components and sequences employed in the construction of the vectors and viruses described herein may be readily obtained from commercial or academic sources based on previously published and described sequences. Viral materials may also be obtained from an individual patient. The viral sequences and vector components may be generated by resort to the teachings and references contained herein, coupled with standard recombinant molecular cloning techniques known and practiced by those skilled in the art. Modifications of existing nucleic acid sequences forming the vectors, including sequence deletions, insertions, and other mutations taught by this specification may be generated using standard techniques. Similarly, the methods employed for the selection of viral sequences useful in a vector, the cloning and construction of the "minigene" and its insertion into a desired viral shuttle vector and the production of a recombinant infectious virus are within the skill in the art given the teachings provided herein.

A. Construction of the Transgene Containing "Minigene"

A "minigene" in this context is defined as above, except that the components of this minigene are designed to express the gene product in vivo. Such components include conventional regulatory elements necessary to drive expression of the transgene in a cell transfected with the recombinant virus. For this minigene, a selected promoter is operatively linked to the transgene and located, with other regulatory elements, within the selected viral sequences of the recombinant vector. Selection of the promoter is a routine matter and is not a limitation of this invention. Useful promoters may be constitutive promoters or regulated (inducible) promoters, which will enable control of the amount of the transgene to be expressed. For example, a desirable promoter is that of the cytomegalovirus (CMV) immediate early promoter/enhancer [see, e.g., Boshart et al, *Cell*, 41:521–530 (1985)]. Another desirable promoter includes the Rous sarcoma virus LTR promoter/enhancer. Still another promoter/enhancer sequence is the chicken cytoplasmic β-actin (CB) promoter [T. A. Kost et al, *Nucl. Acids Res*., 11(23):8287 (1983)]. Other suitable promoters may be selected by one of skill in the art.

The minigene may also desirably contain nucleic acid sequences heterologous to the viral vector sequences including poly-A sequences and introns with functional splice donor and acceptor sites, as described above. The poly-A sequence generally is inserted in the minigene following the transgene sequences and before the 3' adenovirus sequences. A minigene of the present invention may also contain an intron, desirably located between the promoter/enhancer sequence and the transgene. Selection of these and other common vector elements are conventional as described above and many such sequences are available from commercial and industrial sources as well as from Genbank.

As above stated, the minigene is located in the site of any selected deletion in the recombinant adenovirus. In the exemplary E1/E4 deleted recombinant adenovirus H5.001CBLacZ, the transgene is located in the deleted E1 gene region. However, the transgene may be located elsewhere in the adenovirus sequence, as desired.

B. Production of Recombinant Adenovirus

Adenovirus sequences useful in this invention may include the DNA sequences of a number of adenovirus types, which are available from Genbank, including type Ad5 [Genbank Accession No. M73260]. The adenovirus sequences may be obtained from any known adenovirus serotype, such as serotypes 2, 3, 4, 7, 12 and 40, and further including any of the presently identified 41 human types [see, e.g., Horwitz, cited above].

Similarly adenoviruses known to infect other animals may also be employed in the vector constructs of this invention. The selection of the adenovirus type is not anticipated to limit the following invention. A variety of adenovirus strains are available from the American Type Culture Collection, Manassas, Va., or available by request from a variety of commercial and institutional sources. In the following exemplary embodiment an adenovirus, type 5 (Ad5) is used for convenience.

However, it is desirable to obtain a variety of adenovirus shuttle vectors based on different human adenovirus serotypes. It is anticipated that a library of such plasmids and the resulting recombinant adenoviruses would be useful in a therapeutic regimen to evade cellular, and possibly humoral, immunity, and lengthen the duration of transgene expression, as well as improve the success of repeat therapeutic treatments. Additionally the use of various serotypes is believed to produce recombinant viruses with different tissue targeting specificities. Additionally, the absence of adenoviral genes E1 and E4 in the recombinant adenovirus of this invention should reduce or eliminate adverse CTL responses which normally cause destruction of recombinant adenoviruses deleted of only the E1 gene.

Recombinant adenoviruses of this invention are recombinant, defective adenoviruses (i.e., E1 deleted) which are also deleted completely or functionally of the E4 gene region. Functional deletions of E4 gene regions may be assessed by assays of Examples 2 and 3, among other assays. Recombinant adenoviruses of useful in this invention may optionally bear other mutations, e.g., temperature sensitive mutations in the E2a gene region, and deletions in the E3 gene regions.

An adenovirus of this invention contains a functional deletion of the adenoviral early immediate early gene E1a (which spans mu 1.3 to 4.5) and delayed early gene E1b (which spans mu 4.6 to 11.2). Similarly the adenovirus has a functional deletion of the E4 region (which spans mu 92 to 97.2), or at least of ORF6 of the E4 region.

Gene regions which may be optionally deleted in the E1/E4 deleted recombinant viruses of this invention include all or a portion of the adenovirus delayed early gene E3 (which spans mu 76.6 to 86.2). The function of E3 is irrelevant to the function and production of the recombinant virus particle.

The recombinant adenovirus of this invention may also have a mutation which results in reduced expression of adenoviral protein and/or reduced viral replication. For example, a temperature-sensitive mutation may be introduced into the adenovirus delayed early gene E2a (which spans mu 67.9 to 61.5). Among such mutations include the incorporation of the missense temperature-sensitive (ts) mutation in the (DBP)E2a region found in the Ad5 H5ts125 strain [P. Vander Vliet et al, *J. Virol*., 15:348–354 (1975)] at 62.5 mu. A single amino acid substitution (62.5 mu) at the carboxy end of the 72 kd protein produced from the E2a gene in this strain produces a protein product which is a single-stranded DNA binding protein and is involved in the replication of adenoviral genomic DNA. At permissive temperatures (approximately 32° C.) the ts strain is capable of full life cycle growth on HeLa cells, while at non-permissive temperatures (approximately 38° C.) no replication of adenoviral DNA is seen. In addition, at non-permissive temperatures, decreased immunoreactive 72 kd protein is seen in HeLa cells. See, e.g., J. F. Engelhardt et al, *Hum. Gene Ther*., 5:1217–1229 (1994); J. F. Engelhardt et al, *Proc. Natl. Acad. Sci., USA*, 91:6196–6200 (1994) and International patent application WO95/13392, published May 18, 1995, incorporated by reference herein.

However, it should be understood that other deletions in the adenovirus genome as previously described in the art or otherwise may also occur in the recombinant viruses of this invention. One minimal type of recombinant adenovirus can contain adenovirus genomic sequences from which all viral genes are deleted. More specifically, the adenovirus sequences may be only the cis-acting 5' and 3' inverted terminal repeat (ITR) sequences of an adenovirus (which function as origins of replication) and the native 5' packaging/enhancer domain, that contains sequences necessary for packaging linear Ad genomes and enhancer elements for the E1 promoter. The adenovirus 5' sequence containing the 5' ITR and packaging/enhancer region (Ad5 mu 0–1 or bp 1–360) can be employed as the 5' adenovirus sequence in recombinant adenoviruses of this invention. The 3' adenovirus sequences including the right terminal (3') ITR sequence of the adenoviral genome spanning about bp 35,353-end of the adenovirus genome, or map units ˜98.4–100 may be desirably employed as the 3' sequence of the recombinant adenovirus. These sequences, which are clearly devoid of the E1 and E4 genes, can flank, or be operatively associated with the minigene in a recombinant virus. Any other necessary Ad gene products will then be supplied by helper viruses and the E1/E4 ORF6 expressing packaging cell of this invention.

Exemplary recombinant adenoviruses for use in this invention, for example, may be obtained by homologous recombination of desired fragments from various recombinant adenoviruses, a technique which has been commonly employed to generate other recombinant adenoviruses for gene therapy use. In the examples below, a representative recombinant adenovirus, H5.001CBLacZ, is constructed by homologous recombination between the adenovirus dl1004 (also H5dl1004) viral backbone and pAdCBLacZ minigene DNA. H5dl1004 is an Ad5 virus deleted of from about map unit 92.1 through map unit 98, i.e, substantially the entire E4 gene. The dl1004 virus is described in Bridge and Ketner, *J. Virol.*, 632(2):631–638 (Feburary 1989), incorporated by reference herein.

The pAdCBLacZ vector is a CDNA plasmid containing Ad m.u. 0–1, an E1 deletion into which is inserted a bacterial β-galactosidase gene under the control of a chicken β-actin promoter, with other regulatory elements as described below, and flanked by Ad m.u. 9–16 and plasmid sequence.

The production of the E1/E4 recombinant adenovirus of this invention in the novel packaging cell line of this invention utilizes conventional techniques. Such techniques include conventional cloning techniques of cDNA such as those described in texts [Sambrook et al, cited above], use of overlapping oligonucleotide sequences of the adenovirus genomes, polymerase chain reaction, and any suitable method which provides the desired nucleotide sequence. Standard transfection and co-transfection techniques are employed, e.g., $CaPO_4$ transfection techniques using the complementation 293 cell line. Other conventional methods employed include homologous recombination of the viral genomes, plaquing of viruses in agar overlay, methods of measuring signal generation, and the like.

For example, following the construction and assembly of the desired minigene-containing plasmid vector pAdCBLacZ, the E1/E4 expressing packaging cell line of this invention is infected with the helper virus H5dl1004. The infected cell line is then subsequently transfected with the an adenovirus plasmid vector by conventional methods. Homologous recombination occurs between the E4-deleted H5dl1004 helper and the pAdCBLacZ vector, which permits the adenovirus-transgene sequences in the vector to be replicated and packaged into virion capsids, resulting in the recombinant virus. About 30 or more hours post-transfection, the cells are harvested, an extract prepared and the recombinant virus containing the LacZ transgene is purified by buoyant density ultracentrifugation in a CsCl gradient.

III. Use of the Recombinant Virus in Gene Therapy

The resulting recombinant adenovirus containing the transgene produced by cooperation of the adenovirus vector and E4 deleted helper virus and packaging cell line, as described above, thus provides an efficient gene transfer vehicle which can deliver the transgene to a patient in vivo or ex vivo and provide for integration of the gene into a mammalian cell.

The above-described recombinant viruses are administered to humans in a conventional manner for gene therapy and serve as an alternative or supplemental gene therapy for the disorder to which the transgene is directed. A recombinant adenovirus of this invention may be administered to a patient, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The recombinant viruses are administered in sufficient amounts to transfect the desired target cells, e.g., muscle, liver, epithelial, etc. and provide sufficient levels of transfer and expression of the transgene to provide a therapeutic benefit without undue adverse or with medically acceptable physiological effects which can be determined by those skilled in the medical arts. Conventional and pharmaceutically acceptable routes of administration include direct delivery to the muscle or other selected cell, intranasal, intravenous, intramuscular, subcutaneous, intradermal, oral and other parental routes of administration. Routes of administration may be combined, if desired.

Dosages of recombinant virus will depend primarily on factors such as the condition being treated, the age, weight and health of the patient, and may thus vary among patients. For example, a therapeutically effective human dose of the recombinant adenovirus is generally in the range of from about 20 to about 100 ml of saline solution containing concentrations of from about $1\times10^9$ to $1\times10^{11}$ pfu/ml virus. A preferred human dose is estimated to be about 50 ml saline solution at $2\times10^{10}$ pfu/ml. The dose will be adjusted to balance the therapeutic benefit against any side effects. The levels of expression of the transgene can be monitored to determine the frequency of administration.

An optional method step involves the co-administration to the patient, either concurrently with, or before or after administration of the recombinant virus of a suitable amount of a short acting immune modulator. The selected immune modulator is defined herein as an agent capable of inhibiting the formation of neutralizing antibodies directed against the recombinant vector of this invention or capable of inhibiting or substantially delaying cytolytic T lymphocyte (CTL) elimination of the vector. Among desirable immune modulators are interleukin-12 [European Patent Application No. 441,900]; gamma interferon [S. C. Morris et al, *J. Immunol.*, 152:1047 (1994)]; interleukin-4 [U.S. Pat. No. 5,017,691]; antibody to the CD4 protein, such as anti-OKT 3+ [see, e.g., U.S. Pat. No. 4,658,019] or antibody GK1.5 (ATCC Accession No. TIB207); a soluble CD40 molecule or an antibody to CD40 ligand (Bristol-Myers Squibb Co) [European patent application 555,880, published Aug. 18, 1993]; a soluble form of B7 or an antibody to CD28 or CTLA4 [CTLA4-Ig (Bristol-Myers Squibb Co), European patent application 606,217, published Jul. 20, 1994], or agents such as cyclosporin A or cyclophosphamide.

Thus, the compositions and methods of this invention provide a desirable gene therapy treatment.

The following examples illustrate the construction and testing of the novel packaging cell lines, the E1/E4 deleted recombinant adenovirus of the present invention and the use thereof. These examples are illustrative only, and do not limit the scope of the present invention.

EXAMPLE 1

Novel E1a/E1b and E4 Expressing Packaging Cell Lines

A. Construction of E4 ORF 6 Expressing Plasmids 1. pMTE4ORF6

One exemplary plasmid useful for the construction of a packaging cell line of this invention is pMTE4ORF6, which contains a sheep metallothionine promoter (MT promoter) [M. G. Peterson et al, cited above] in control of the transcription of a human E4 ORF 6 gene sequence (nucleotides 1521 to 2406 of SEQ ID NO: 1 in FIG. 2), a growth hormone terminator (GH), an SV40 origin of replication, plasmid sequences from pBR322-based plasmid including a neomycin resistance gene, an SV40 polyadenylation site and an ampicillin resistance gene.

The various functional fragments of this plasmid may be readily replaced with other conventionally used sequences and are not critical to the design of the plasmid.

2. pMMTVE4ORF6

Another exemplary plasmid useful for the construction of a packaging cell line of this invention is pMMTVE4ORF6, which contains a mouse mammary tumor virus promoter (MMTV) (nucleotides 1–1506 of SEQ ID NO: 1 in FIG. 2) in transcriptional control of a human E4 ORF 6 gene sequence (nucleotides 1523–2408 of SEQ ID NO: 1 in FIG. 2), a growth hormone terminator (GH) (nucleotides 2409–3654 of SEQ ID NO: 1 in FIG. 2), an SV40 origin of replication, plasmid sequences from plasmid pBR322, including a neomycin resistance gene, and an ampicillin resistance gene. The various functional fragments of this plasmid may be readily replaced with other conventionally used sequences and are not critical to the design of the plasmid.

3. pLTR.E4(−) Endogenous E4 Promoter

A plasmid used as a control for the construction of a packaging cell line of this invention is pLTR.E4(−). This plasmid contains the constitutive retroviral MLV LTR and most of the Ad E4 gene region except that the endogenous E4 promoter and a portion of E4 ORF1 are missing. The other plasmid sequences remain the same as described above.

4. pLTR.E4(+) Endogenous E4 Promoter

Still another plasmid useful for the study of the methods of this invention is pLTR.E4, which contains the constitutive MLV LTR and endogenous E4 promoter and an intact E4 gene. The other plasmid sequences remain the same as described above.

B. Transfections and Selection of Clones

Each of the above-described plasmids was transfected by the calcium phosphate precipitation technique into the human embryonic kidney cell line 293 [ATCC CRL1573] which expresses the product of the adenovirus E1 genes, seeded on 100 mm plates (10 μg plasmid/plate). Twenty four hours post-transfection, cells were harvested and seeded at varying dilutions (1:10–1:100) in 100 mm plates for about 10 days. Seeding media contain G418 (Geneticin, BRL) at 1 mg/ml. Resistant colonies that developed were selected using the following assays and expanded. Preliminary analysis of clones was based on enhanced transduction efficiency of a recombinant adeno-associated virus, AV.CMVLacZ, and immunofluorescence localization of Ad E4 protein as described in the following examples.

EXAMPLE 2

AV.CMVLacZ Transduction Enhancement Assay

E1 and E4 Ad gene products are needed for recombinant adeno-associated virus (AAV) function. This primary assay involves seeding the packaging cell lines of Example 1 in 96 well 35 mm culture plates ($2\times10^6$ cells/well) and infecting the cells with purified, heat-treated AV.CMVLacZ at an MOI of 1000 virus particles/cell.

A. Preparation of AV.CMVLacZ

A recombinant AAV virus was prepared by conventional genetic engineering techniques for the purposes of this experiment. Recombinant AAV was generated by plasmid transfections in the presence of helper adenovirus [Samulski et al, *J. Virol*., 63:3822–3828 (1989)]. A cis-acting plasmid pAV.CMVLacZ was derived from psub2ol [Samulski et al, *J. Virol*., 61: 3096–3101 (1987)] and contains an *E. coli* β galactosidase minigene in place of AAV Rep and Cap genes. The 5' to 3' organization of the recombinant AV.CMVLacZ genome (4.9 kb) includes (a) the 5' AAV ITR (bp 1–173) was obtained by PCR using pAV2 [C. A. Laughlin et al, *Gene*, 23: 65–73 (1983)] as template;

(b) a CMV immediate early enhancer/promoter [Boshart et al, *Cell*, 41:521–530 (1985)];

(c) an SV40 intron;

(d) *E. coli* beta-galactosidase cDNA;

(e) an SV40 polyadenylation signal (a 237 Bam HI-BclI restriction fragment containing the cleavage/poly-A signals from both the early and late transcription units; and (f) 3' AAV ITR, obtained from pAV2 as a SnaBI-BglII fragment.

Rep and Cap genes were provided by a trans-acting plasmid pAAV/Ad [Samulski et al, cited above].

Monolayers of 293 cells grown to 90% confluency in 150 mm culture dishes ($5\times10^7$ cells/plate) were infected with H5.CBALP at an MOI of 10. H5.CBALP (also called H5.010ALP) is a recombinant adenovirus that contains an alkaline phosphatase minigene in place of adenovirus E1a and E1b gene sequences (map units 1–9.2 of the Ad5 sequence of GenBank [Accession No. M73260]). The alkaline phosphatase cDNA is under the transcriptional control of a CMV-enhanced β-actin promoter in this virus. This helper virus is described in Goldman et al, *Hum. Gene Ther*., 6:839–851 (July, 1995); Engelhardt et al, *Hum. Gene Ther*., 5:1217–1229 (October, 1994); and references cited therein.

Infections were done in Dulbecco's Modified Eagles Media (DMEM) supplemented with 2% fetal bovine serum (FBS) at 20 ml media/150 mm plate. Two hours post-infection, 50 μg plasmid DNA (37.5 μg trans-acting and 12.5 μg cis-acting) in 2.5 ml of transfection cocktail was added to each plate and evenly distributed. Transfections were calcium phosphate based as described [B. Cullen, *Meth. Enzymol*., 152:684–704 (1987)]. Cells were left in this condition for 10–14 hours after which the infection/transfection media was replaced with 20 ml fresh DMEM/2% FBS. Forty to fifty hours post-transfection, cells were harvested, suspended in 10 mM Tris-Cl (pH 8.0) buffer (0.5 ml/150 mm plate) and a lysate prepared by sonication. The lysate was brought to 10 mM manganese chloride, after which bovine pancreatic DNase I (20,000 units) and RNase (0.2 mg/ml final concentration) were added, and the reaction incubated at 37° C. for 30 minutes. Sodium deoxycholate was added to a final concentration of 1% and incubated at 37° C. for an additional 10 minutes.

The treated lysate was chilled on ice for 10 minutes and solid CsCl added to a final density of 1.3 g/ml. The lysate was brought to a final volume of 60 ml with 1.3 g/ml CsCl solution in 10 mM Tris-Cl (pH 8.0) and divided into three equal aliquots. Each 20 ml sample was layered onto a CsCl step gradient composed of two 9.0 ml tiers with densities 1.45 g/ml and 1.60 g/ml.

Centrifugation was performed at 25,000 rpm in a Beckman SW-28 rotor for 24 hours at 4° C.

Fractions containing peak titers of functional AV.CMV-LacZ virus were combined and subjected to three sequential rounds of equilibrium sedimentation in CsCl. Rotor selection included a Beckman NVT-90 (80,000 rpm for 4 hours) and SW-41 (35,000 rpm for 20 hours). At equilibrium, AV.CMVLacZ appeared as an opalescent band at 1.40–1.41 g/ml CsCl. Densities were calculated from refractive index measurements. Purified vector was exchanged to 20 mM HEPES buffer (pH7.8) containing 150 mM NaCl (HBS) by dialysis and stored frozen at −80° C. in the presence of 10% glycerol or as a liquid stock at −20° C. in HBS/40% glycerol.

Purified virus was tested for contaminating H5.CBALP helper virus and AV.CMVLacZ titers. Helper virus was monitored by histochemical staining for reporter alkaline phosphatase activity. A sample of purified virus representing 1.0% of the final product was added to a growing monolayer of 293 cells seeded in a 60 mm plate. Forty-eight hours later, cells were fixed in 0.5% glutaraldehyde/phosphate buffered saline (PBS) for 10 minutes at room temperature, washed in PBS (3×10 minutes) and incubated at 65° C. for 40 minutes to inactivate endogenous alkaline phosphatase activity. The monolayer was allowed to cool to room temperature, rinsed once briefly in 100 mM Tris-Cl (pH9.5)/100 mM NaCl/5 mM MgCl, and incubated at 37° C. for 30 minutes in the same buffer containing 0.33 mg/ml nitroblue tetrazolium chloride (NBT) and 0.165 mg/ml 5-bromo-4-chloro-3-indolylphosphate p-toluidine salt (BCIP). Color development was stopped by washing the monolayer in 10 mM Tris-Cl (pH 8.0)/5 mM EDTA. Routinely the purification scheme described above removed all detectable H5.CBALP helper virus by the third round of buoyant density ultracentrifugation.

AV.CMVLacZ titers were measured according to genome copy number (virus particles/ml), absorbance at 260 nm ($A_{260}$ particles/ml) and LacZ Forming Units (LFU/ml). Virus particle concentrations were based on Southern blotting. Briefly, a sample of purified AV.CMVLacZ was treated with capsid digestion buffer (50 mM Tris-Cl, pH 8.0/1.0 mM EDTA, pH 8.0/0.5% SDS/Proteinase K 1.0 mg/ml) at 50° C. for one hour to release virus DNA. The reactions were allowed to cool to room temperature, loading dye was added and electrophoresed through a 1.2% agarose gel. Standard quantities of ds AV.CMVLacZ genome were also resolved on the gel.

DNAs were electroblotted onto a nylon membrane, hybridized with a $^{32}P$ random primer labeled restriction fragment, and the resulting blot scanned on a PhosphorImager 445 SI (Molecular Dynamics). A standard curve was generated from the duplex forms and used to extrapolate the number of virus genomes in the sample. LFU titers were generated by infecting indicator cells with limiting dilutions of virus sample. Indicator cells included HeLa and 293. Twenty-four hours later, cells were fixed in glutaraldehyde and cells were histochemically stained for *E. coli* β-galactosidase (LacZ) activity as described in J. M. Wilson et al, *Proc. Natl. Acad. Sci. USA*, 85:3014–3018 (1988). One LFU is described as the quantity of virus that is sufficient to cause visually detectable β-galactosidase expression in one cell 24 hours post-infection.

B. Induction of ORF6 Expression

Induction of ORF6 expression with 10 μM dexamethasone or 150 μM zinc sulfate (for negative control, no inducer used) was initiated 2 hours before the addition of virus and continued throughout the duration of the experiment. Twenty-four hours after the addition of virus, cells were harvested, lysates were generated by sonication and analyzed for the β-galactosidase expression (i.e., β-galactosidase activity) and virus DNA as described above. Hirt extracts were prepared from low molecular weight DNA from cell extracts. The preparation of the Hirt extracts and subsequent analysis by Southern hybridization were performed by resort to conventional procedures known to one of skill in the art.

In the absence of the inducers, the packaging cell lines generate lower levels of β-galactosidase in rAAV infected cells. Induction of ORF6 expression with the inducer dexamethasone results in a concomitant rise in AV.CMVLacZ cell transduction to a level that was much greater than the parent 293 line. Expression of E1 alone was insufficient to have an effect in the adenovirus mediated augmentation of rAAV transduction.

Results are demonstrated for certain positive clones in the Table I below (see Example 4). However, for 30 cell lines having an MMTV promoter and ORF6 sequence, 4 demonstrated over 90% blue cells illustrative of LacZ production in the presence of dexamethasone, i.e., 293-27-6, 293-27-17, 293-27-18 and 293-27-28.

EXAMPLE 3

Immunofluorescence Localization of Ad5 Late Protein

Positive clones from the assay of Example 2 were infected with the recombinant E4 deleted adenovirus H5dl1004 and screened for E4 complementation using an immunofluorescence assay for late gene expression. The H5dl1004 virus was obtained from Dr. Ketner of Johns Hopkins University and is described in Bridge and Ketner, *J. Virol.*, 632(2):631–638 (Feburary 1989), incorporated by reference herein. Because ORF6 of E4 complements late Ad gene expression, specifically in the formation of the hexon and penton fibers of the adenovirus, cell lines containing ORF6 are able to bind with antibody against these proteins.

Each cell line of Example 1 is infected with E4 deleted virus H5dl1004 virus at an MOI of 0.1. The cells were treated with mouse anti-adenovirus FITC-labeled monoclonal antibody to either the hexon or penton fibers in a 1:10 dilution (Chemicon International Inc., Temecula, Calif.). Positive clones were identified by reaction with the antibody.

EXAMPLE 4

Relative Plaguing Efficiency

The cell lines of Example 1 demonstrating with strong complementation ability in Example 3 were screened for relative plaquing efficiency of H5dl1004 as compared to W162 cells (an E4-complementing Vero cell line which does not express E1) [Weinberg and Ketner, *Proc. Natl. Acad. Sci. USA*, 80(17):5383–5386 (1983)]. In Table II below, RPE %, i.e., relative plaquing efficiency, represents the titer of H5dl1004 on tested cell lines/titer of H5dl1004 on W162 cells. For example, the RPE of 293 cells is 0.

The positive cell lines selected by all criteria are identified in Table I below, with the results of the assays of Examples 2, 3 and 4.

TABLE I

| E1/E4 Double Complementing Cell Lines | | | | | |
|---|---|---|---|---|---|
| Cell | Trans- | Pro- | AV.CMV | | |
| Line | Gene | moter | IF/LP | LacZ | RPE % |
| 293-10-3 | ORF6 | MT | ++++ | ++++ | 246 |
| 293-39-11 | ORF6 | LTR | ++++ | +++ | 52 |
| 293-84-31 | E4- | LTR | ++++ | ++++ | 179 |
| 293-12-31 | whole E4 | LTR + E4 | ++++ | ++++ | 174 |
| 293-27-6 | ORF6 | MMTV | | +++++ | 327 |
| 293-27-17 | ORF6 | MMTV | | ++++ | 313 |
| 293-27-18 | ORF6 | MMTV | | +++++ | 339 |
| 293-27-28 | ORF6 | MMTV | | ++++ | 261 |

Cell line 293-10-3 and cell line 293-27-18 were deposited in the American Type Culture Collection as Accession Nos. PTA-2361 and PTA-2511, respectively, on Aug. 11, 2000 and Sep. 26, 2000, respectively. These deposits were made in accordance with the requirements of the Budapest Treaty. Such deposits will be replaced for at least 30 years from the date of the original deposits, or at least five years from the date of the most recent request for release of a sample, or for the life of any patent issued on this application, whichever period is longer.

EXAMPLE 5

Construction and Purification of H5.001CBLacZ

The plasmid pAd.CBLacZ was constructed as described in detail in K. Kozarsky et al, *Som. Cell Mol. Genet.*, 19(5): 449–458 (1993), incorporated by reference herein. This plasmid contained a minigene comprising a 5' flanking NheI restriction site, followed by Ad5 sequence m.u. 0–1, followed by an E1 deletion into which is inserted a CMV enhancer/chicken β-actin promoter sequence [T. A. Kost et al, *Nucl. Acids Res.*, 11(23):8287 (1983)], which controls the transcription of the following bacterial β-galactosidase, followed by a poly A sequence and flanked 3' by Ad m.u. 9–16, and another NheI site. In the plasmid, the minigene was flanked on both sides by plasmid sequence containing drug resistance markers.

The plasmid pAd.CBLacZ was linearized with NheI and co-transfected by the calcium phosphate co-transfection method into the novel packaging cell line of Example 1 with ClaI digested H5dl1004 (an Ad5 sequence deleted of from about map unit 92.1 through map unit 98, corresponding to substantially the entire E4 gene).

Figure 3:
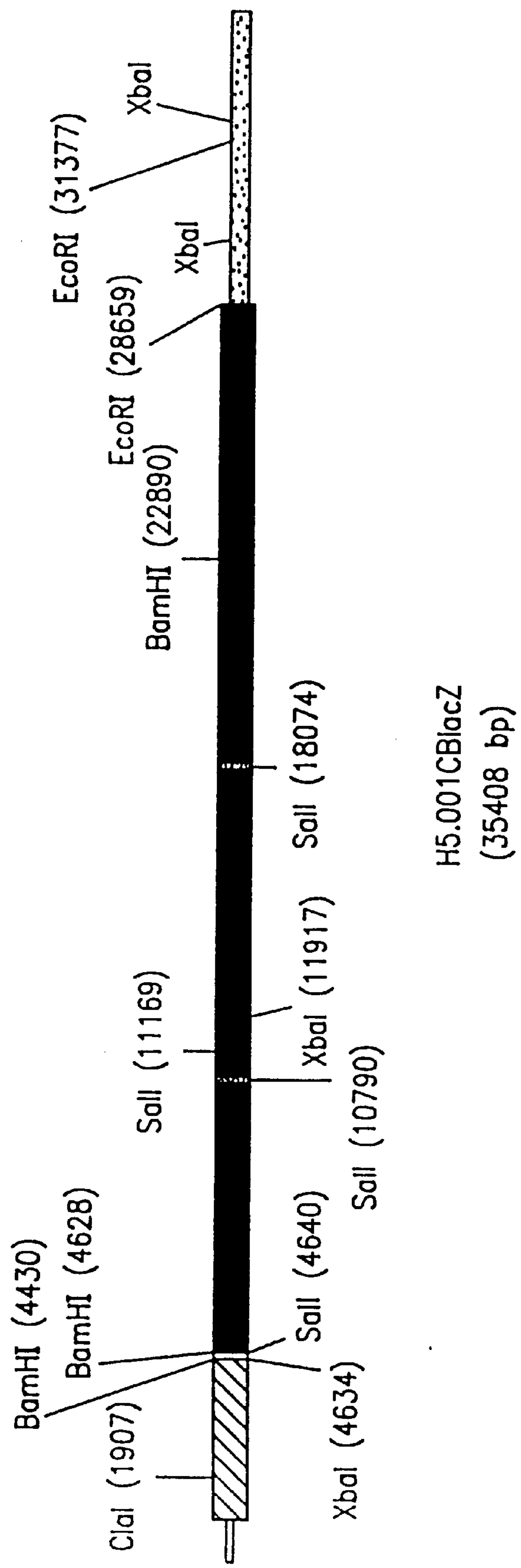
FIG. 3 is a schematic map of recombinant adenovirus H5.001CBLacZ, with indicated restriction endonuclease enzyme sites. The striated bar represents the CBLacZ minigene; the black bar represents Ad5 viral backbone, the crosshatched bar represents Ad E4 deletion.

Homologous recombination occurs in the cell line between these two viral constructs between Ad map units 9–16, resulting in recombinant adenovirus, designated H5.001CBLacZ (FIGS. 3 and 4). This recombinant adenovirus contains the sequence from about nucleotide 1 to about 4628 from pAd.CBLacZ and Ad5 map units 9–92.1 and 97.3 to 100 from H5dl1004. This recombinant adenovirus is thereby functionally deleted, and substantially structurally deleted, of the Ad E1 and E4 genes.

Viral plaques were selected and screened by the β-galactosidase assay [Wilson (1988), cited above] and H5.001CBLacZ was isolated following three rounds of plaque purification. The purified virus was also subjected to cesium chloride density centrifugation and large scale production. For the following mouse experiments, virus was used after column purification and glycerol was added to a final concentration of 10% (v/v). Virus was stored at −70° C. until use.

EXAMPLE 6

Growth Kinetics of H5.001CBLacZ in Packaging Cell Lines

Figure 5:
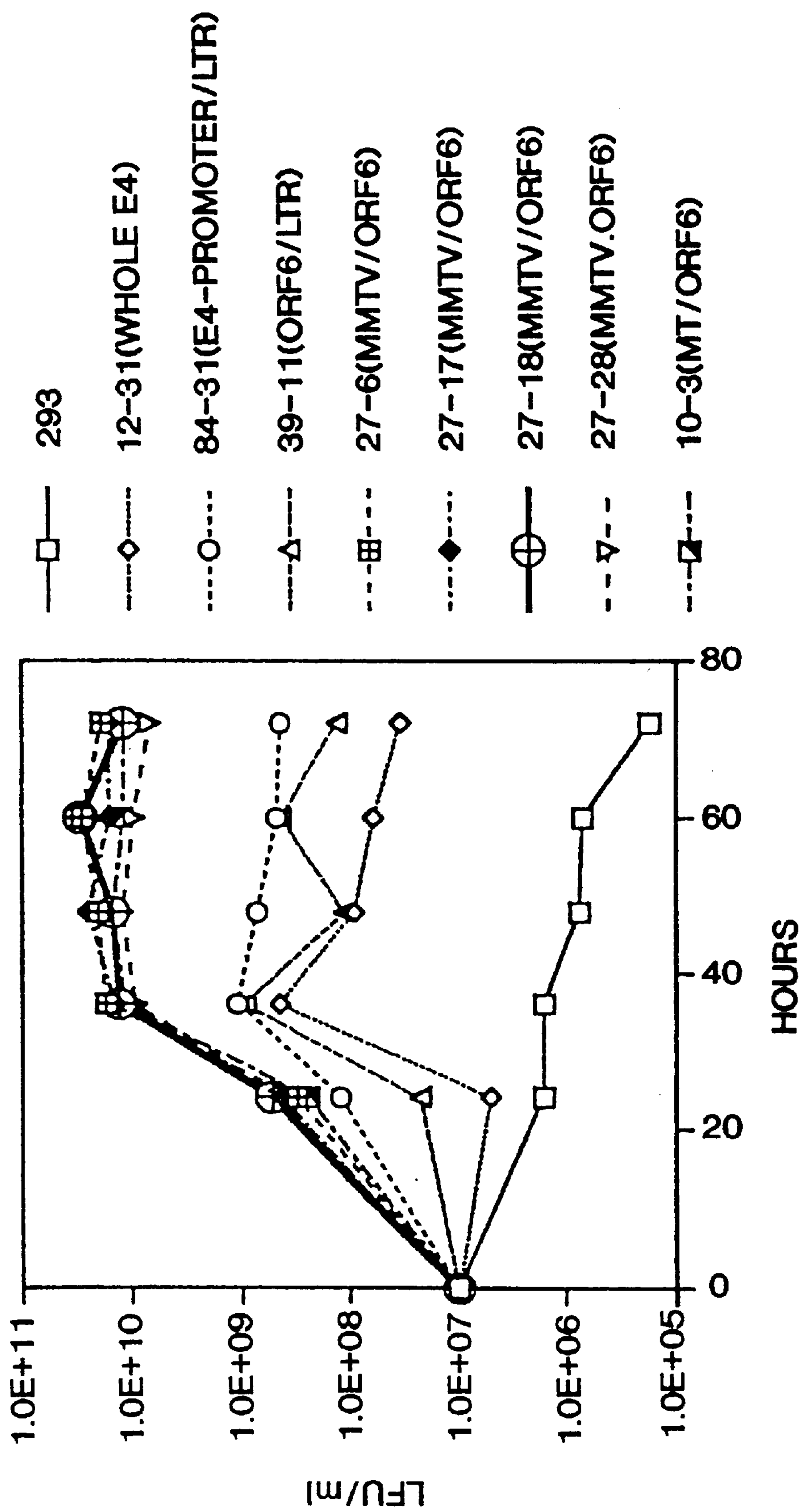
FIG. 5 is a graph plotting LacZ forming units/ml vs time (hours) for E4 complementing cell lines infected with H5.001CBLacZ.
Figure 6A:
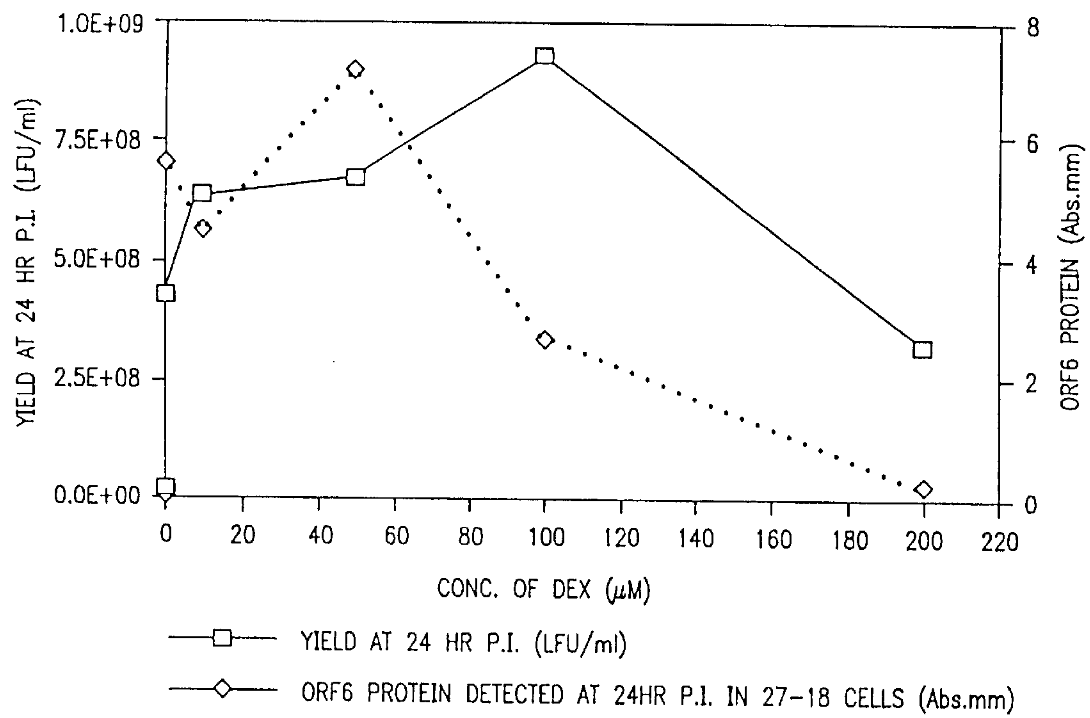
FIG. 6A is a graph of the induction, ORF6 expression and viral production in 293-27-18 packaging cells plotting yield at 24 hours post-infection in LacZ forming units (LFU)/ml and ORF6 protein (abs.mm) vs. concentration of the inducer, dexamethasone ($\mu$M). The unit reference, abs.mm, indicates the intensity of the size of the protein band on a Western blot and reflects absorbence and protein size in $mm^2$. The square represents the yield at 24 hours post infection. The diamond represents ORF6 protein detected at 24 hours post-infection.
Figure 6B:
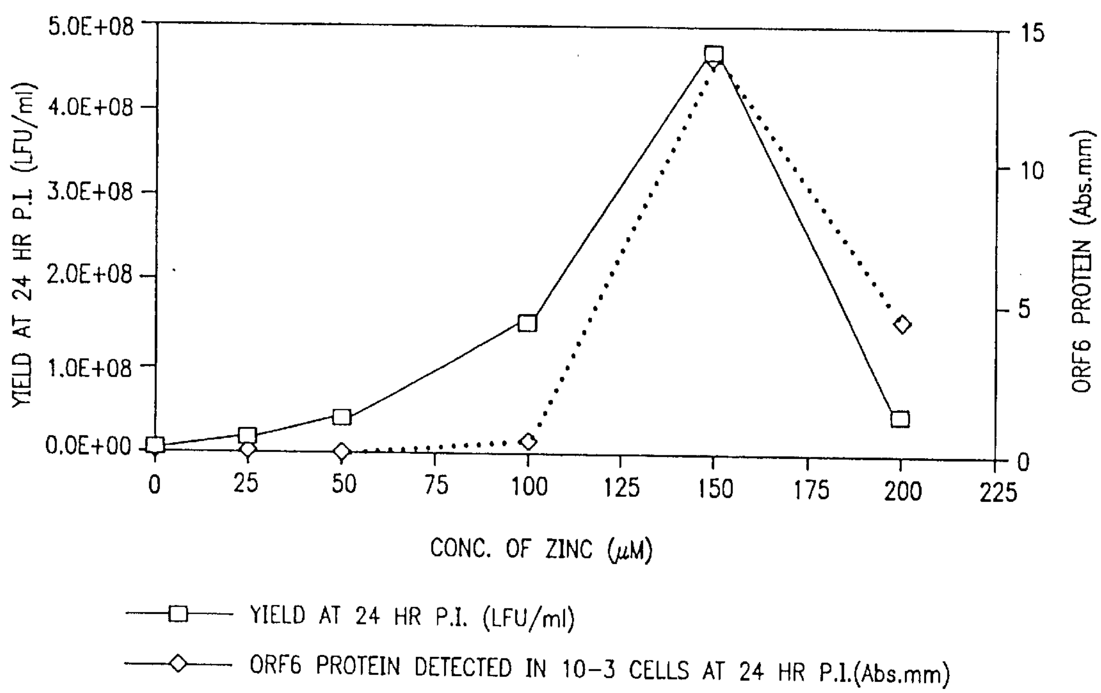
FIG. 6B is a graph of the induction, ORF6 expression and viral production in 293-10-3 packaging cells plotting yield at 24 hours post-infection in LFU/ml and ORF6 protein (abs.mm) vs. concentration of the inducer, zinc ($\mu$M). The symbols are as described for FIG. 6A.

The cell lines reported in Example 1 were infected with recombinant H5.001CBLacZ at an MOI of 0.5. The growth kinetics of this virus in the E4 complementing cell lines are shown in FIG. 5.

Maximum viral yield is reported as LFU/ml in Table II below.

TABLE II

| Cell Line | Maximum Viral Yield |
|---|---|
| 293-10-3 | $2.8 \times 10^{10}$ |
| 293-39-11 | $9.5 \times 10^{8}$ |
| 293-84-31 | $1.1 \times 10^{9}$ |
| 293-12-31 | $4.5 \times 10^{8}$ |
| 293-27-6 | $2.8 \times 10^{10}$ |
| 293-27-17 | $2.5 \times 10^{10}$ |
| 293-27-18 | $2.9 \times 10^{10}$ |
| 293-27-28 | $1.2 \times 10^{10}$ |

When grown in 293-27-18 cells (the E4 ORF6 cell line with MMTV promoter inducible by dexamethasone) the maximum yield of this virus is $2.9\times10^{10}$ LFU/ml. Several of the cell lines were passaged between 5 and 20 times and the viral production of the passages remained stable. However, RPE did fall following repeated passages of cells.

EXAMPLE 7

Other Recombinant Adenoviruses

Other related recombinant adenoviruses were prepared similarly to H5.001CBLacZ by homologous recombination between pAdCBLacZ and other helper viruses.

As one example, H5.000CBLacZ is a recombinant E1 deleted Ad5 which contains the same minigene as H5.001CBLacZ, but has an intact E4 gene. This recombinant virus was prepared as described by homologous recombination between pAdCBLacZ and a wild-type Ad5.

As another example, H5.010CBLacZ contains the adenovirus map units 0–1, followed by a CMV enhanced, chicken cytoplasmic β-actin promoter, the *E. coli* beta-galactosidase gene (lacZ), a polyadenylation signal (pA), and adenovirus type 5 map units 9–100, with a small deletion in the E3 gene (the Ad 5 sub360 backbone). This recombinant virus may be prepared by homologous recombination between the pAdCBLacZ vector and Ad5 virus sub360, which contains a 150 bp deletion within the 14.6 kD protein of the E3 gene. See, e.g., J. F. Engelhardt et al, *Proc. Natl. Acad. Sci., USA*, 91:6196–6200 (June 1994); and Engelhardt et al, *Hum. Gene Ther.*, 5:1217–1229 (October 1994), both incorporated by reference herein.

These recombinant adenoviruses were isolated following transfection [Graham, *Virol.*, 52:456–467 (1974)], and were subjected to two rounds of plaque purification. Lysates were purified by cesium chloride density centrifugation as previously described [Englehardt et al, *Proc. Natl. Acad. Sci. USA*, 88:11192–11196 (1991)]. Cesium chloride was removed by passing the virus over a BioRad DG10 column using phosphate-buffered saline.

EXAMPLE 8

LacZ Gene Transfer into Mouse

A. Transfer into Mouse Muscle

Five to six-week old male C57B/6 mice were anesthetized. Anterior tibialis muscles were exposed and directly injected with either recombinant adenovirus H5.000CBLacZ, H5.010CBLacZ or H5.001CBLacZ as follows: 25 μL of purified viral suspension at a stock concentration of $5\times10^{11}$ virus particles/mL was injected by inserting the tip of the 33 gauge needle of a 100 μL Hamilton syringe into the belly of the muscle.

Animals were sacrificed on day 4, 14, 28 and 60 post injection. The muscles were dissected and frozen in liquid nitrogen cooled isopentane. Six μM sections were cut in a cryostat, fixed and stained for β-galactosidase activity for 6 hours at 37° C.

While the blue stained recombinant virus was found for each virus in the day 4 and day 14 (most abundant) stains, by day 28, the H5.001CBLacZ clearly demonstrated more virus on day 28. By day 60, the only virus which stained positive was the H5001.CBLacZ.

B. Transfer into Mouse Lung and Circulation

Recombinant adenovirus H5.000CBLacZ (control), and H5.001CBLacZ ($1\times10^{11}$ viral particles) were administered to six week old C57BL/6 female mice by tail vein injection and trachea installation. The animals were sacrificed and their liver and lung tissues were harvested at days 4, 9, 21, 28 and 35 post-administration. The transgene and viral late gene expression were compared.

At therapeutic doses of virus, there was diminished expression of late viral proteins at all time points in comparison with transgene.

C. Dose Responses in Liver

Dose responses of E4-deleted and E4 intact recombinant adenoviruses in the liver of C57BL/6 mice were studied by tail vein administration of $1.5\times10^{11}$, $5\times10^{10}$, $1.7\times10^{10}$, $5.6\times10^{9}$, and $1.9\times10^{9}$ viral particles and comparing the transgene and viral late gene expression at day 4, 21, 28, 35, and 42 post administration.

At therapeutic doses of virus, there was diminished expression of late viral proteins at all time points in comparison with transgene.

EXAMPLE 9

Other Gene Transfers

A. Human OTC Gene Transfer

The human OTC gene [A. L. Horwich et al, *Science*, 224:1068–174 (1984)] or the human CFTR gene [Riordan et al, *Science*, 245:1066–1073 (1989)] was used to replace the LacZ as the transgene in the recombinant E1/E4 deleted adenoviruses described above, using the techniques analogous for the construction of the above-described LacZ vectors.

The resulting human OTC-containing recombinant viruses were administered at an MOI of 10 to 30 to human hepatocytes. The E1/E4 deleted recombinant adenovirus demonstrated less replication and less late gene expression than when the E1/E4 deleted recombinant adenoviruses are administered to muscle, as described in the example above. However, the results of this gene transfer are better than comparable transfers with recombinant adenoviruses containing only a deletion in the E1 gene or a deletion in the E1 gene and a point mutation in the E2a gene.

Similar results are demonstrated when the transgene is CFTR and the method of administration is intratracheal into lungs.

All references recited above are incorporated herein by reference. Numerous modifications and variations of the present invention are included in the above-identified specification and are expected to be obvious to one of skill in the art. Such modifications and alterations to the compositions and processes of the present invention, such as selections of different transgenes and plasmids for the construction of the packaging cell lines and recombinant adenoviruses, or selection or dosage of the viruses or immune modulators, are believed to be within the scope of the claims appended hereto.

What is claimed is:

1. The cell line 293-10-3 ATCC Accession No. PTA-2361.

2. A method for producing a recombinant adenovirus deleted in the E1 and E4 genes, comprising the step of:

introducing to cell line 293-10-3 ATCC Accession No. PTA-2361

(i) a recombinant vector comprising adenovirus 5' and 3' cis elements necessary for replication and packaging flanking a transgene under the control of regulatory sequences that direct expression of said transgene in a host cell, and (ii) a helper virus providing any adenovirus genes not present in the cell line or in said vector, that are necessary to permit production of said recombinant adenovirus.

3. The method according to claim 2, further comprising culturing said cells under conditions which permit packaging of said transgene into a recombinant E1, E4-deleted adenovirus.

4. The method according to claim 3, further comprising purifying said recombinant adenovirus from cellular debris.

5. The cell line 293-27-18 ATCC Accession No. PTA-2511.

6. A method for producing a recombinant adenovirus deleted in the E1 and E4 genes, comprising the step of:

introducing to cell line 293-27-18 ATCC Accession No. PTA-2511

(i) a recombinant vector comprising adenovirus 5' and 3' cis elements necessary for replication and packaging flanking a transgene under the control of regulatory sequences that direct expression of said transgene in a host cell, and (ii) a helper virus providing any adenovirus genes not present in the cell line or in said vector, that are necessary to permit production of said recombinant adenovirus.

7. The method according to claim 6, further comprising culturing said cells under conditions which permit packaging of said transgene into a recombinant E1, E4-deleted adenovirus.

8. The method according to claim 6, further comprising purifying said recombinant adenovirus from cellular debris.

* * * * *